(12) United States Patent
Lau et al.

(10) Patent No.: US 6,350,767 B1
(45) Date of Patent: *Feb. 26, 2002

(54) COMPOUNDS WITH GROWTH HORMONE RELEASING PROPERTIES

(75) Inventors: Jesper Lau, Farum; Bernd Peschke, Måløv; Thomas Kruse Hansen, Herlev; Nils Langeland Johansen, Copenhagen; Michael Ankersen, Frederiksberg, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,993

(22) Filed: Nov. 19, 1999

Related U.S. Application Data

(62) Division of application No. 08/897,239, filed on Jul. 17, 1997, now Pat. No. 6,013,658, which is a continuation of application No. PCT/DK96/00045, filed on Jan. 26, 1996.

(30) Foreign Application Priority Data

| Jan. 27, 1995 | (DK) | 0099/95 |
| Jan. 27, 1995 | (DK) | 0100/95 |
| Sep. 28, 1995 | (DK) | 1083/95 |
| Sep. 28, 1995 | (DK) | 1084/95 |
| Dec. 4, 1995 | (DK) | 1372/95 |

(51) Int. Cl.$^7$ .................... C07D 271/06; C07D 233/01; A61K 31/16; A61K 31/42

(52) U.S. Cl. .................. 514/364; 514/326; 514/616; 514/666; 546/209; 548/131; 564/153; 564/155; 564/345; 564/502

(58) Field of Search .................. 546/209; 548/131; 564/562, 153, 155, 345; 514/326, 364, 666, 616

(56) References Cited

U.S. PATENT DOCUMENTS 5,977,178 A  11/1999  Hansen et al. ............. 514/616
6,013,658 A  1/2000  Lau et al. .................. 514/364

FOREIGN PATENT DOCUMENTS

WO  WO 95/17423  6/1995

OTHER PUBLICATIONS

McDowell et al., "Growth Hormone Secretagogues: Characterization, Efficacy, and Minimal Bioactive Conformation" Proc. Natl. Acad. Sci. USA, vol. 92. pp. 11165–11169, Nov. 1995, Biochemistry.

Elias et al., "In Vitro Characterization Of Four Novel Classes Of Growth Hormone–Releasing Peptide", Endocrinology, vol. 136, No. 12. pp. 5694–5699.

*Primary Examiner*—Floyd D. Higel
(74) *Attorney, Agent, or Firm*—Reza Green, Esq.

(57) ABSTRACT

The present invention relates to compounds, compositions containing them, and their use for treating medical disorders resulting from a deficiency in growth hormone.

11 Claims, No Drawings

COMPOUNDS WITH GROWTH HORMONE RELEASING PROPERTIES

CROSS-REFERENCE TO RELATED APPLICATIONS

This application is a division of U.S. application Ser. No. 08/897,239, filed on Jul. 17, 1997 now U.S. Pat. No. 6,013,658, which is a continuation of PCT/DK96/00045 filed Jan. 26, 1996 which claims priority under 35 U.S.C. 119 of Danish applications 0099/95 filed Jan. 27, 1995, 0100/95 filed Jan. 27, 1995, 1083/95 filed Sep. 28, 1995, 1084/95 filed Sep. 28, 1995, and 1372/95 filed Dec. 4, 1995, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration nonviable. Furthermore, other directly acting natural secretagogues, e.g., GHRH and PACAP, are longer polypeptides for which reason oral administration of them is not viable.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 95/17422, WO 95/17423 and WO 95/14666.

The composition of growth hormone releasing compounds is important for their growth hormone releasing potency as well as their bioavailability. It is therefore the object of the present invention to provide compounds with growth hormone releasing properties which have improved properties relative to known peptides of this type.

SUMMARY OF THE INVENTION

Accordingly, the present invention relates to a compound of general formula I

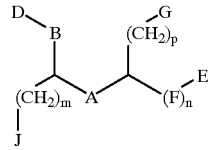

I

Wherein
n is 0 or 1;
m is 1 or 2;
p is 0, 1 or 2;
A is

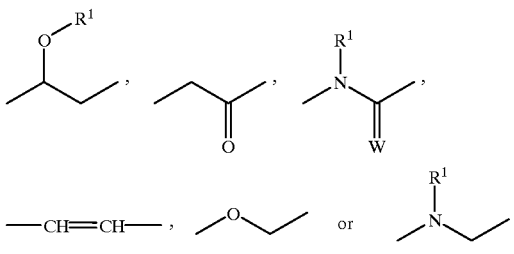

wherein $R^1$ is hydrogen or $C_{1-6}$-alkyl,
W is =O or =S;
B is

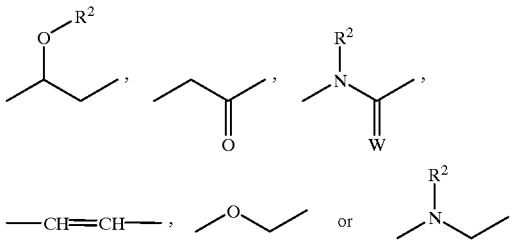

wherein $R^2$ is hydrogen or $C_{1-6}$-alkyl,
W' is =O or =S;
D is

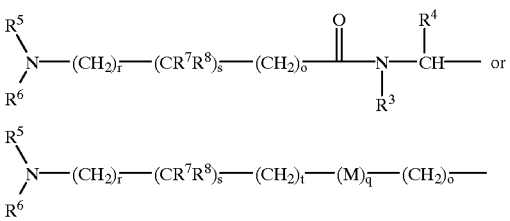

wherein $R^3$, $R^4$, $R^5$, $R^6$, $R^7$ and $R^8$ independently are hydrogen or $C_{1-6}$-alkyl optionally substituted with halogen, amino, hydroxy or aryl;
$R^5$ and $R^6$, $R^6$ and $R^7$, $R^5$ and $R^8$ or $R^7$ and $R^8$ optionally forming —(CH$_2$)$_i$—U—(CH$_2$)$_j$—, wherein i and j independently are 1 or 2, and U is —O—, —S— or a valence bond;
M is —O—, —S—, —CH=CH—,

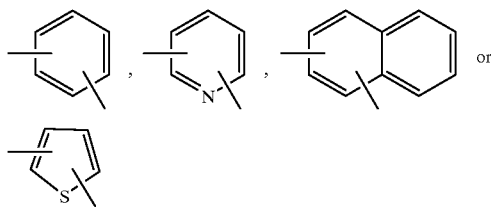 or optionally substituted with halogen, amino, hydroxy, $C_{1-6}$-alkyl or $C_{1-6}$-alkoxy;
o, r and t are independently 0, 1, 2, 3 or 4;
q and s are independently 0 or 1;
and r+s+t is 1, 2, 3 or 4;
E is hydrogen,

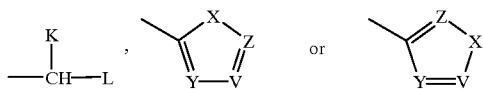

wherein L is hydrogen, —OR$^9$, —CONR$^9$R$^{10}$, $C_{1-6}$-alkyl obtionally substituted with hydroxy or $C_{1-6}$-alkoxy,
or L is

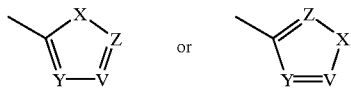

wherein R$^9$ and R$^{10}$ are independently hydrogen, $C_{1-6}$-alkyl or together form —(CH$_2$)$_k$—U'—(CH$_2$)$_l$—,
wherein k and l independently are 1, 2 or 3, and k+l is 3, 4, 5 or 6,
U' is —O—, —S— or a valence bond;
X is —N(R$^{11}$)—, —O— or —S—,
V is —C(R$^{12}$)= or —N=,
Y is —C(R$^{13}$)= or —N=,
Z is —C(R$^{14}$)= or —N=,
R$^{12}$, R$^{13}$ and R$^{14}$ independently are hydrogen, —COOR$^{15}$, —CONR$^{16}$R$^{17}$, —(CH$_2$)$_v$NR$^{16}$R$^{17}$, —(CH$_2$)$_u$OR$^{15}$, halogen, hydroxy, branched or linear $C_{1-6}$-alkyl, phenyl, oxazol-5-yl, 5-methyl-[1,2,4]oxadiazol-3-yl, R$^{11}$, R$^{15}$, R$^{16}$ and R$^{17}$ independently are hydrogen or branched or linear $C_{1-6}$-alkyl obtionally substituted with aryl, and u and v are independently 0 or 1, 2, 3, 4, 5 or 6;
K is hydrogen or

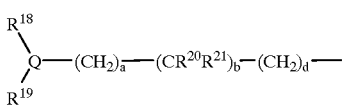

wherein R$^{18}$, R$^{19}$, R$^{20}$ and R$^{21}$ are independently hydrogen, $C_{1-6}$-alkyl optionally substituted with halogen, amino, $C_{1-6}$-alkylamino, hydroxy or aryl; R$^{18}$ and R$^{19}$, R$^{18}$ and R$^{21}$, R$^{19}$ and R$^{20}$ or R$^{20}$ and R$^{21}$ optionally forming —(CH$_2$)$_{k'}$—Z—(CH$_2$)$_{l'}$— where k' and l' independently are 1, 2 or 3, and k'+l' are 3, 4, 5 or 6;

Z is —O—, —S— or avalence bond;
b is 0 or 1;
a and d are independently 0, 1, 2, 3 or 4;
and a+b is 1 to 4;
Q is >CR$^{22}$— or >N—,
wherein R$^{22}$ is hydrogen or $C_{1-6}$-alkyl,
F is

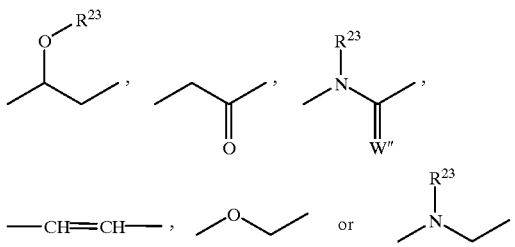

wherein R$^{23}$ is hydrogen or $C_{1-6}$-alkyl,
W" is =O or =S;
G is hydrogen,

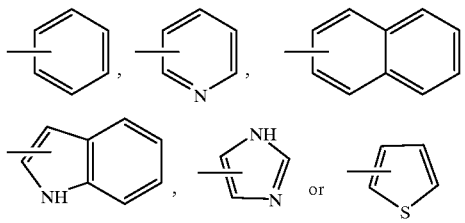

optionally substituted with halogen, amino, hydroxy, $C_{1-6}$-alkyl or $C_{1-6}$-alkoxy;
J is

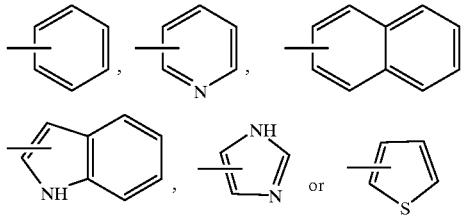

optionally substituted with halogen, amino, hydroxy, $C_{1-6}$-alkyl or $C_{1-6}$-alkoxy;

or a pharmaceutically acceptable salt thereof, and the compounds of formula I comprise any optical isomers thereof, in the form of separated, pure or partially purified optical isomers or racemic mixtures thereof.

Regarding the above compounds of the general formula I preferred substituents are mentioned in the dependent claims. Furthermore, especially preferred substituents are those mentioned below.

Preferred groups of A are

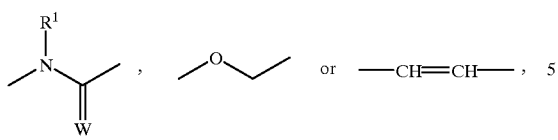

wherein $R^1$ and W are as defined above.

Preferred groups of $R^1$ is $C_{1-6}$-alkyl, and more preferred $C_{1-3}$-alkyl such as methyl, ethyl, cyclopropyl and isopropyl.

Preferably m is 1 and/or p is 1.

Preferred groups of B are

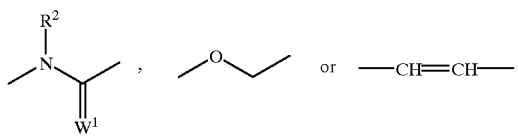

wherein $R^2$ and $W^1$ are as defined above.

Preferably $R^2$ is $C_{1-6}$-alkyl, and more preferred $C_{1-3}$-alkyl such as methyl, ethyl, cyclopropyl and isopropyl.

Preferably D is

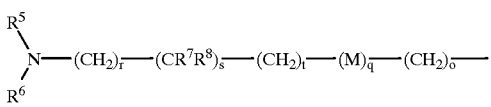

wherein $R^5$, $R^6$, $R^7$, $R^8$, M, s, t, q and o are as defined above.
Preferably $R^5$ and $R^6$, $R^6$ and $R^7$, $R^5$ and $R^8$ or $R^7$ and $R^8$ are optionally forming —$(CH_2)_i$—U—$(CH_2)_j$—, wherein U, i and j are as defined above.

Preferably U is a valence bond.

Preferably M is —O—, —CH=CH— or

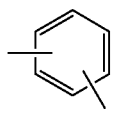

Preferably o, r and t are independently 0, 1, 2 or 3.

Specifically preferred D is 4-piperidinyl, 3-piperidinyl, 3-aminomethylphenyl, 3-amino-3-methyl-butenyl or 4-amino-4-methyl-pentenyl.

Preferably K is hydrogen.

Preferably F is

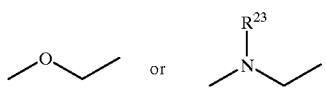

wherein $R^{23}$ is as defined above.

Preferably G is

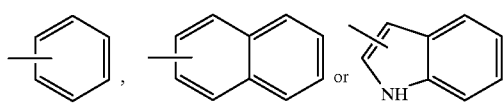

The meanings of the above preferred substituents should in no way be construed as limiting the invention to such substituents Representative compounds of the present invention include the following:

3-Aminomethyl-N-((1R, 2E, 4S)-4-carbamoyl-5-(2-naphthyl)-1-(2-naphthyl)methylpent-2-enyl)benzamide:

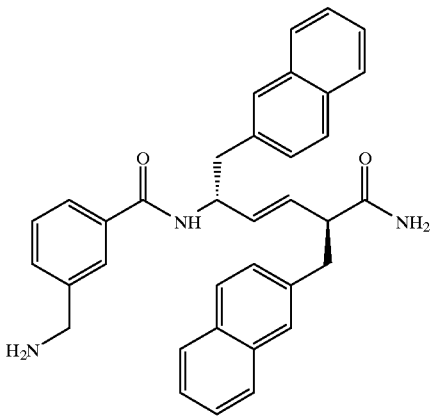

Piperidine-4-carboxylic acid ((1R, 2E, 4S)-4-carbamoyl-5-(2-naphthyl)-1-(2-naphthyl)methylpent-2-enyl) amide:

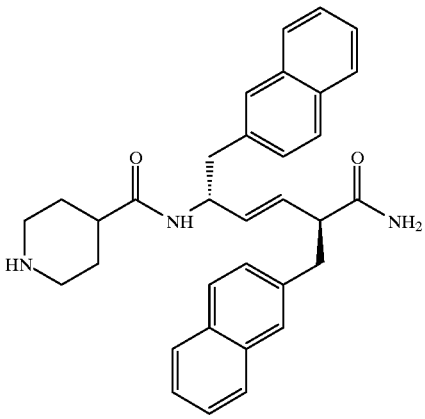

N-((1R)-1-((1R)-1-((1S)-5-Amino-1-(dimethylcarbamoyl) pentylcarbamoyl)-2-phenylethoxy)methyl-2-(2-naphthyl) ethyl)-3-aminomethylbenzamide:

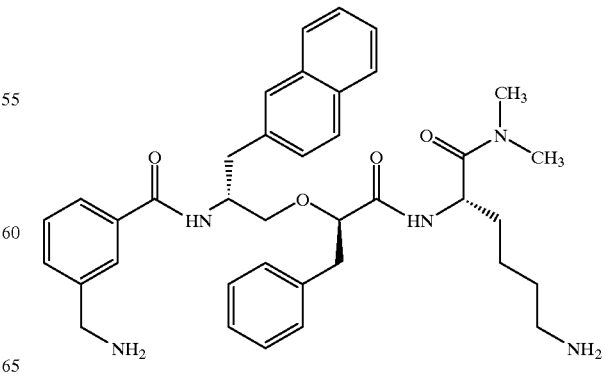

N-((1R, 4S)-4-(((1S)-5-Amino-1-(dimethylcarbamoyl)
  pentyl)carbamoyl)-1-((2-naphthyl)methyl)-2-oxo-5-
  phenylpentyl)-3-aminomethylbenzamide:

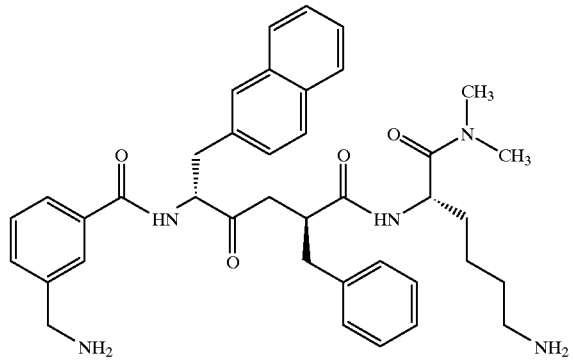

N-((1R, 2R, 4S)-4-(((1S)-5-Amino-1-(dimethylcarbamoyl)
  pentyl)carbamoyl)-2-hydroxy-1-((2-naphthyl)methyl)-5-
  phenylpentyl)-3-aminomethylbenzamide:

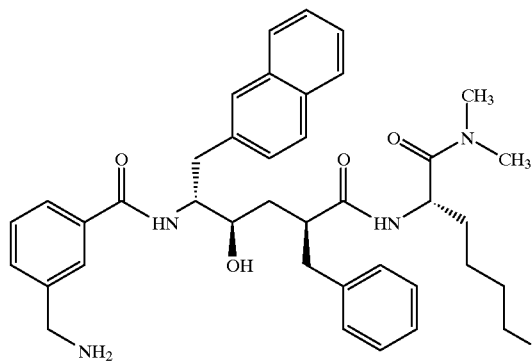

Piperidine-3-carboxylic acid ((1R, 2R, 4S)-4-(((1S)-5-
  amino-1-(dimethylcarbamoyl)pentyl)carbamoyl)-2-
  hydroxy-1-(2-naphthyl)methyl)-5-phenylpentyl)amide:

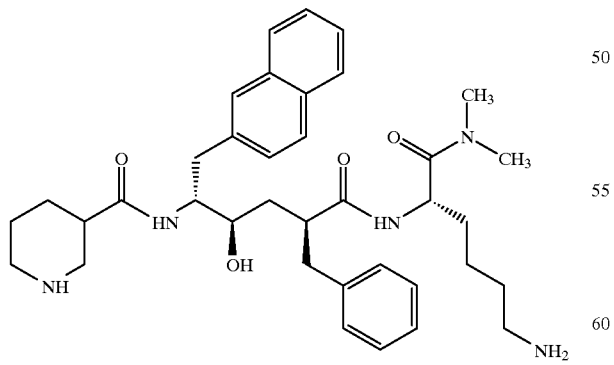

5-((1R)-1-(N-Methyl-N-((2R)-3-(2-naphthyl)-2-
  (piperidine-4-carbonylamino)propionyl)amino)-2-(2-
  naphthyl)ethyl)-[1,2,4]oxadiazole-3-carboxylic acid ethy-
  lester:

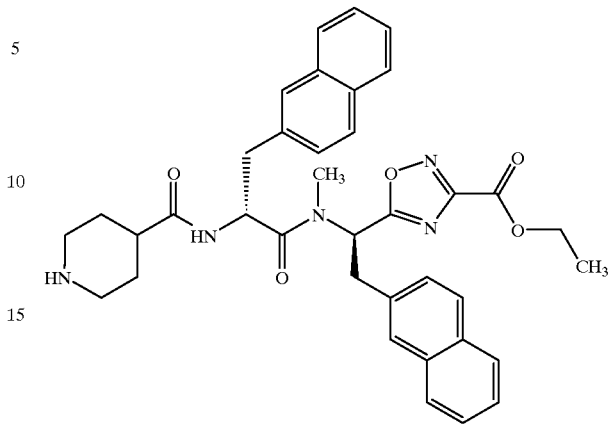

5-((1R)-1-(N-((2R)-2-(3-Aminomethylbenzoylamino)-3-(2-
  naphthyl)propionyl)-N-methylamino)-2-(2-naphthyl)
  ethyl)-[1,2,4]oxadiazole-3-carboxylic acid ethylester:

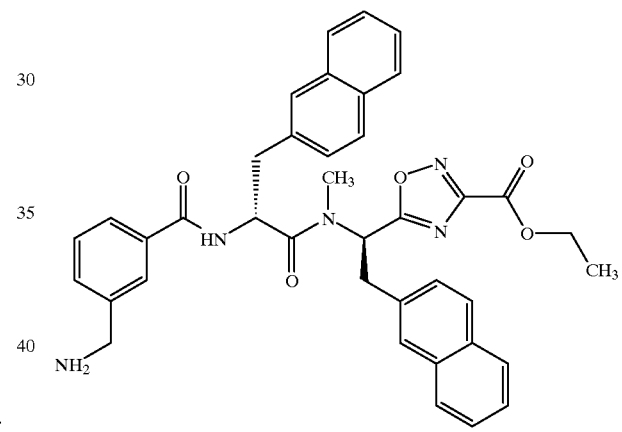

5-((1R)-1-(N-(2R)-2-(3-Aminomethylbenzoylamino)-3-(2-
  naphthyl)propionyl)-N-methylamino)-2-phenylethyl)-[1,
  3,4]oxadiazole-2-carboxylic acid amide:

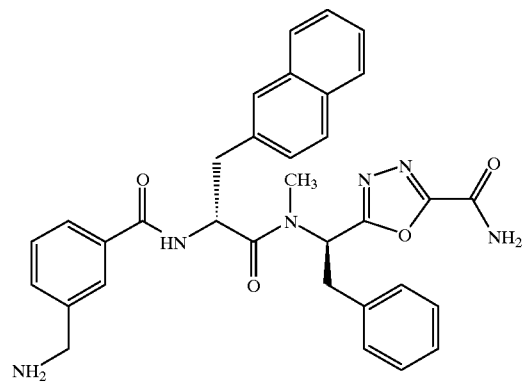

It is believed that compounds of formula I exhibit an improved resistance to proteolytic degradation by enzymes because they are non-natural, in particular because the natural amide bonds are replaced by non-natural amide bond mimetics. The increased resistance to proteolytic degradation combined with the reduced size of the compounds of the invention in comparison with known growth hormone releasing peptides is expected to improve their bioavailability compared to that of the peptides suggested in the prior literature.

In the above structural formulas and throughout the present specification, the following terms have the indicated meanings:

The $C_{1-6}$-alkyl groups specified above are intended to include those alkyl groups of the designated length in either a linear or branched or cyclic configuration. Examples of linear alkyl are methyl, ethyl, propyl, butyl, pentyl and hexyl. Examples of branched alkyl are isopropyl, sec-butyl, tert.-butyl, isopentyl and isohexyl. Examples of cyclic alkyl are cyclopropyl, cyclobutyl, cyclopentyl and cyclohexyl.

Especially preferred $C_{1-6}$-alkyl groups are the $C_{1-3}$-alkyl groups. Preferred $C_{1-3}$-alkyl groups are methyl, ethyl, isopropyl and cyclopropyl.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy and hexoxy. Examples of branched alkoxy are isopropoxy, sec-butoxy, ter.-butoxy, isopentoxy and isohexoxy. Examples of cyclic alkoxy are cyclopropyloxy, cyclobutyloxy, cyclopentyloxy and cyclohexyloxy.

Especially preferred $C_{1-6}$-alkoxy groups are the $C_{1-3}$-alkoxy groups. Preferred $C_{1-3}$-alkoxy groups are methoxy, ethoxy, isopropoxy and cyclopropoxy.

The $C_{1-6}$-alkylamino groups specified above are intended to include those alkylamino groups of the designated length in either a linear or branched or cyclic configuration. Examples of linear alkylamino are methylamino, ethylamino, propylamino, butylamino, pentylamino and hexylamino. Examples of branched alkylamino are isopropylamino, sec-butylamino, tert.-butylamino, isopentylamino and isohexylamino. Examples of cyclic alkylamino are cyclopropylamino, cyclobutylamino, cyclopentylamino and cyclohexylamino.

Especially preferred $C_{1-6}$-alkylamino groups are the $C_{1-3}$-alkylamino groups. Preferred $C_{1-3}$-alkylamino groups are methylamino, ethylamino, isopropylamino and cyclopropylamino.

In the present context, the term "aryl" is intended to include aromatic rings, such as carbocyclic and heterocyclic aromatic rings selected from the group consisting of phenyl, naphthyl, pyridyl, 1-H-tetrazol-5-yl, thiazolyl, imidazolyl, indolyl, quinoline, pyrimidinyl, thiadiazolyl, pyrazolyl, oxazolyl, isoxalyl, thiopheneyl, quinolinyl, pyrazinyl or isothiazolyl, optionally substituted by one or more $C_{1-6}$-alkyl, $C_{1-6}$-alkoxy, aminohalogen or aryl. Aryl is preferably phenyl, thienyl, imidazolyl, pyridyl, indolyl or naphthyl optionally substituted with halogen, amino, hydroxy, $C_{1-6}$-alkyl or $C_{1-6}$-alkoxy. The term "halogen" is intended to include Cl, F, Br and I.

The compounds of the present invention may have one or more asymmetric centres and it is intended that stereoisomers, as separated, pure or partially purified stereoisomers or racemic mixtures thereof are included in the scope of the invention. Compounds of the present invention may be prepared from natural and unnatural amino acid residues as described in the following general methods A to E, and where the starting amino acids can be prepared as known in the art:

General Method A

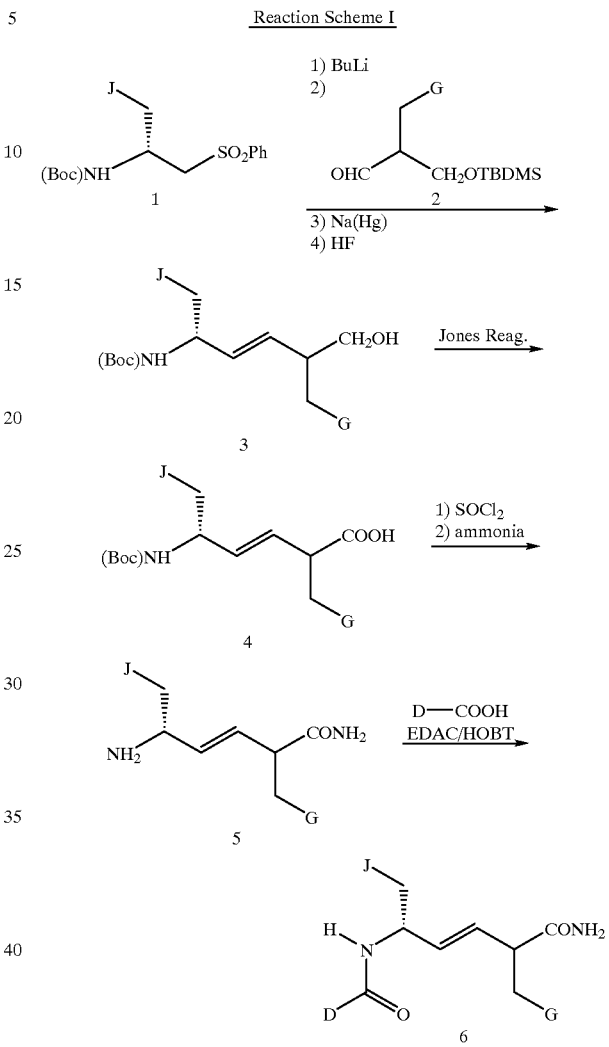

Reaction Scheme I

Compounds of formula I may be prepared as shown in reaction scheme I starting with an appropriate N-protected amino acid which can be converted to sulfone 1 using a known procedure (e.g. Spaltenstein, J. Org. Chem. 1987, 52, 3759). The other starting material 2 may be prepared from dimethyl malonate and an aromatic alkyl halide followed by reduction by LiAlH$_4$, monosilylation with TBDMS and oxidation to aldehyde 2 under Swern conditions according to a known procedure (e.g. Jenmalm, J. Org. Chem 1994, 59, 1139). The reaction between 2 and 1 may be effected by strong base e.g. BuLi in an appropriate solvent e.g. THF followed by reductive conditions (e.g. sodium amalgam) and removal of the silyl protecting group by methods known in the art (e.g. T. W. Greene, Protective Groups in Organic Synthesis, 2nd Ed. John Wiley and Sons 1991) to give alkene 3. These steps can either be carried out one-pot or sequentially. The intermediate 3 may be oxidized by e.g. Jones reagent to a carboxylic acid 4 which may be converted to an amide 5 by treatment with e.g. thionyl chloride and ammonia. Compound 5 may finally be reacted with a protected amino acid using a suitable condensing agent (e.g. DCC) and deprotected by methods which are described by e.g. T. W. Greene (Protective Groups in Organic Chemistry, 2.ed. John Wiley and Sons, 1991) to form compound 6 which is a compound of formula I.

General Method B

Reaction Scheme II

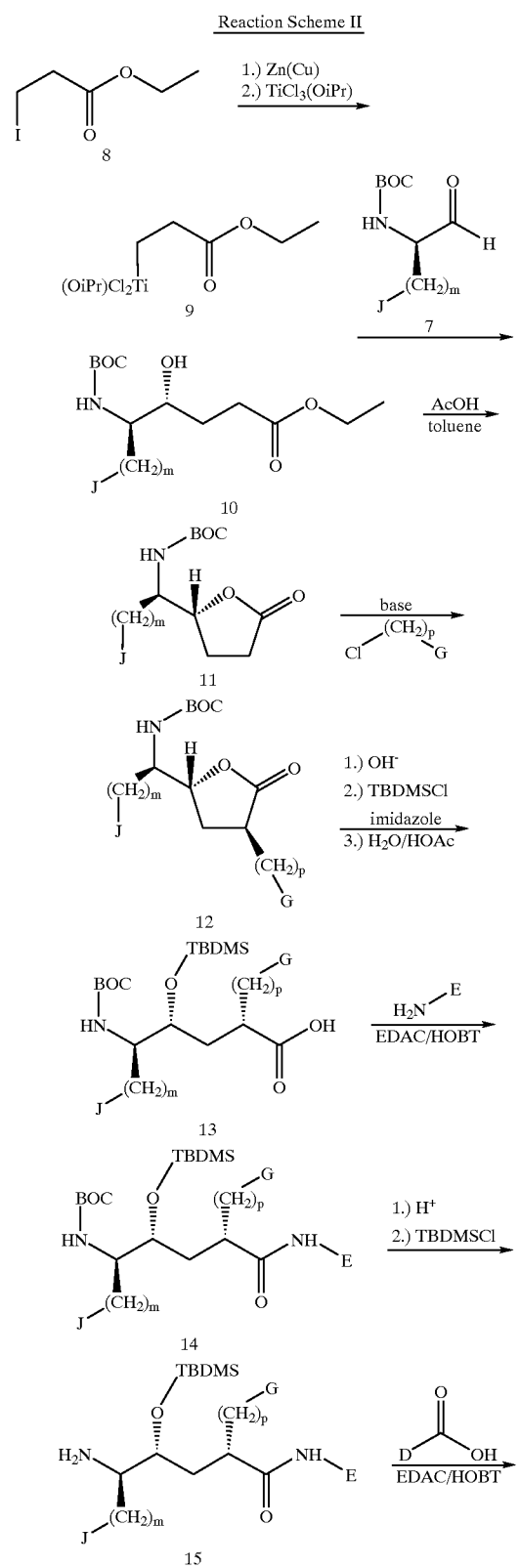

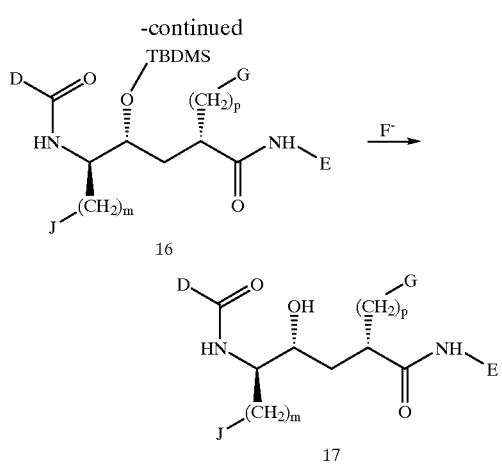

Compound of formula I may be prepared as shown in reaction scheme II starting with the synthesis of intermediate 10 using the procedure of e.g. A. E. DeCamp et al. (Tetrahedron Letters, 1991, 32, 1867–1870.): The titanium-homoenolate 9 may be generated from 3-iodopropionic acid 8 and added onto a suitable aldehyde 7. A cyclization in e.g acetic acid may furnish the lactone 11. Alkylation of the lactone may be done as described by e.g. A. H. Fray et al. (J. Org. Chem., 1986, 51, 4828–4833). The enolate may be generated by treatment with base such as lithium hexamethyldisilazane (LHDS) or Lithium diisopropylamide (LDA) and reacted with a suitable alkylating reagent such as alkylchloride to give a compound of type 12. The lactone may be transferred into a silyl-protected hydroxy acid 13 as described by e.g. A. H. Fray et al (J. Org. Chem., 1986, 51, 4828–4833). Coupling with an amine, which may contain amino protective groups as e.g. phthalimido or FMOC, by reaction with EDAC and HOBT may give an amide of type 14. Deprotection of the amino group using procedures known in the art (e.g. T. W. Greene, Protective Groups in organic Chemistry, 2.ed. John Wiley and Sons 1991) is followed by coupling to a suitable acid, which may include a protection group, by reaction with e.g. EDAC and HOBT to give a compound of type 16. Finally, protection groups on the variable fragments may be removed by methods described in the art (e.g. T. W. Greene, Protective Groups in Organic Synthesis, 2nd. edition, John Wiley and Sons, New York 1991.) to give the final product 17 which is a compound of formula I.

General Method C

Reaction Scheme III

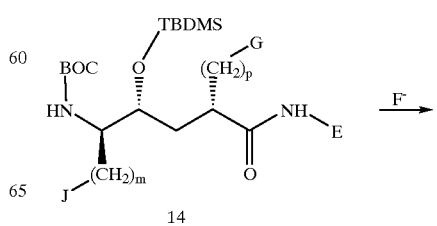

-continued

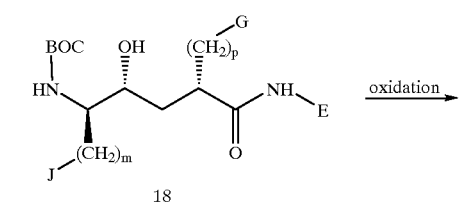
18

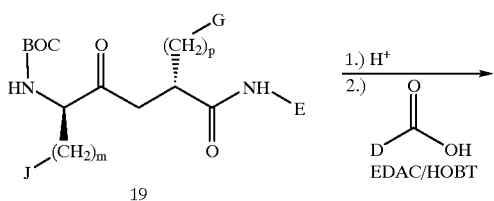
19

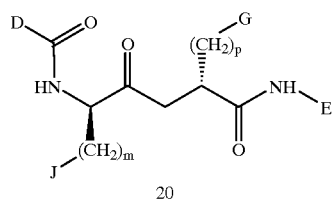
20

Compounds of formula I may be prepared as shown in scheme III starting with deprotection of an amide of type 14 by reaction with e.g. tetrabutylammonium fluoride and subsequent oxidation with a suitable reagent such as PCC or PDC to give a compound 19. The amino group may be deprotected with e.g. hydrochloric acid in ethyl acetate followed by coupling with a suitable acid which may contain a protection group. Finally, protection groups on the variable fragments may be removed by methods described in the art (e.g. T. W. Greene, Protective Groups in Organic Synthesis, 2nd. edition, John Wiley and Sons, New York 1991.) to give the final product 20 which is a compound of formula I.

General Method D

Reaction Scheme IV

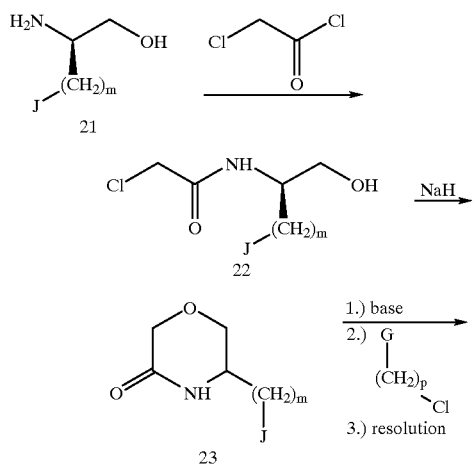

-continued

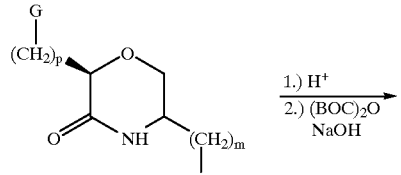
24

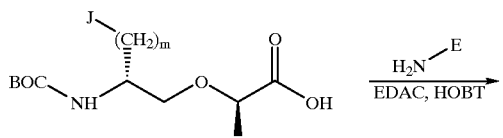
25

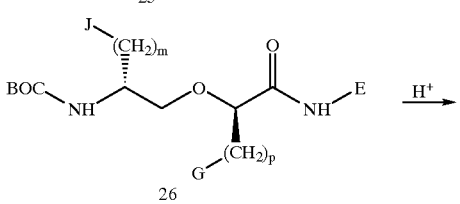
26

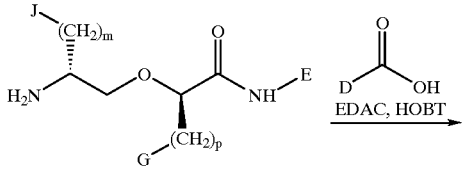
27

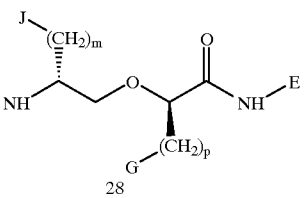
28

Compounds of formula I may be prepared as shown in scheme IV starting with an amino-alcohol of type 21 which may be reacted with chloroacetyl chloride as described in the literature by e.g. E. D. Nicolaides et al. (J. Med. Chem. 1986, 29, 959–971.). Reaction with a base such as sodium hydride in THF may furnish a morpholinone 23 which can be alkylated by using a base such as LDA or LHDS and subsequent addition of a suitable alkylating reagent such as alkyl chloride. After separation of diastereoisomeres, the ring can be opened by reaction with acid as described by e.g. R. E. TenBrink (J. Org. Chem. 1987, 52, 418–422.) and the amino-group can be protected to give a compound 25. The E-fragment, that may contain protected functionalities, can be attached by reaction of a suitable amine using e.g. 1-ethyl-3-(3-dimethylaminopropyl)carbodiimide (EDAC) and 1-hydroxybenzotriazole (HOBT). The amino group in 26 can be deprotected by suitable conditions, such as hydrogene chloride in ethyl acetate, and reacted with a suitable acid, that may contain protection groups, EDAC, and HOBT. Removal of all protection groups by methods described in the art (e.g. T. W. Greene, Protective Groups in Organic Synthesis, 2nd. edition, John Wiley and Sons, New York 1991.), may yield the final product 28 which is a compound of general formula I.

General Method E

Reaction Scheme V

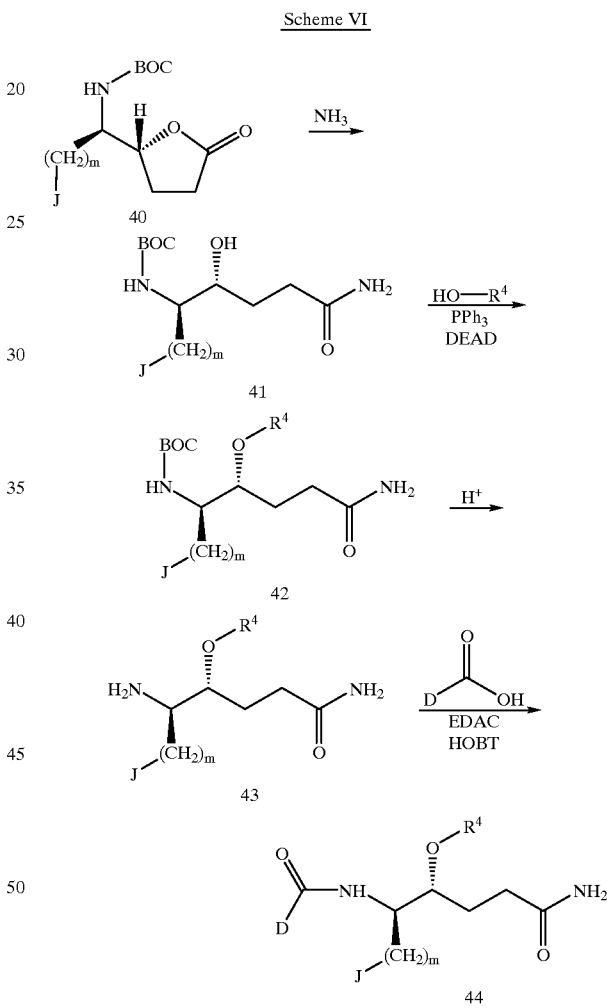

Compounds of formula I may be prepared as shown in reaction scheme V starting with an N-protected amino acid 29 which may be activated with, e.g. EDAC and then reacted with an amido oxime 30 in e.g. pyridine using a known procedure (e.g. J. Heterocyclic Chem. 1989, 26, 125) to give 1,2,4-oxadiazole derivative 31. After deprotection of the amino group using methods known in the art and described by e.g. T. W. Greene (Protective Groups in Organic Synthesis, 2. ed. John Wiley and Sons 1991) the compound can be reductive alkylated using an aldehyde and a mild reducing reagent, such as sodium cyanoborohydride to give the desired intermediate 33. Further reaction of 33 with an N-protected natural or unnatural amino acid 34 using peptide coupling methodologies as described in the art (e.g. DCC coupling in DMF) can give intermediate 35, which after deprotection with e.g. hydrochloric acid in an appropriate solvent, such as ethyl acetate can be coupled with another N-protected aminoacid 37 using a known peptide coupling methodology such as DCC coupling in DMF to give an intermediate which after deprotection of the amino group with e.g. hydrochloric acid in an appropriate solvent, such as ethyl acetate can give the desired product 38 which is a compound of formula I. When $R^{12}$ is a functional group (e.g. an ester) this group may be derivatized at an appropriate step in the reaction sequence.

General method F:

Scheme VI

A compound of formula I may be prepared as shown in scheme V starting with lactone 40 which may be reacted with ammonia to give the amide 41. A reaction under Mitsunobu conditions as described by M. S. Manhas et al. (J. Chem. Soc. Perkin Trans I, 1975, 461–463.) may give an ether 42 which may be deprotected under acidic conditions. Coupling with a suitable acid, that might contain a protected functionality, may give a compound of type 43, which may be deprotected by methods described in the art (e.g. T. W. Greene, Protective Groups in Organic Synthesis, 2nd. edition, John Wiley and Sons, New York 1991.) to give the final product 44 which is a compound of formula I.

General Method G

Scheme VII

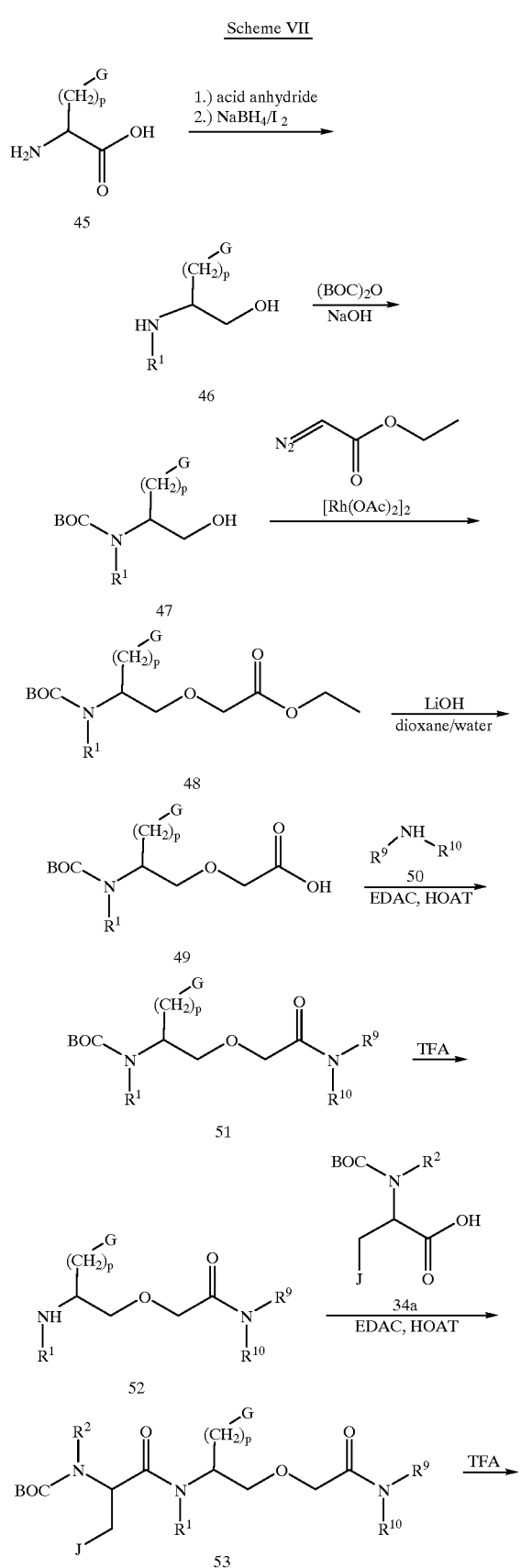
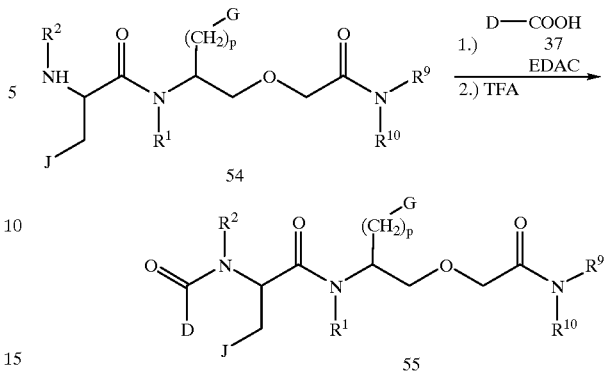

A compound of formula I may be prepared as shown in scheme VII, starting with an amino acid 45, which may be acylated with e.g. an acid anhydride and—after work up—may be subsequently reduced with e.g. diborane, sodium borohydride/iodine or lithium aluminumhydride as described by e.g. M. J. McKennon et. al. (J. Org. Chem, 1993, 58, 3568–3571) in an appropriate solvent such as THF, diethylether, dioxane or hydrocarbons to give an aminoalcohol 46. It may be protected with a method known in the art and described by e.g. T. W. Greene (Protective Groups in Organic Synthesis, 2. ed., John Wiley and Sons, New York 1991), with e.g. di-tert-butoxy dicarbonate or benzoylcarbonyl chloride to give the protected alcohol 47. A reaction with ethyl diazoacetate under rhodium acetate catalysis (preferentially 0.01–15%) as described by e.g. J. Hlaváceck and V. Král (Collect. Czech. Chem. Commun., 1992, 57, 525–530) may furnish the ester 48. The ester may be saponified with a method known in the art and described by e.g. T. W. Greene (Protective Groups in Organic Synthesis, 2. ed., John Wiley and Sons, New York 1991) with bases such as lithium hydroxide or potassium hydroxide to give the acid 49, which may be activated by e.g. 1-ethyl-3-(3-dimethylaminopropyl)carbodiimide hydrogenchloride or a combination of 1-ethyl-3-(3-dimethylaminopropyl) carbodiimide hydrogenchloride and 1-hydroxybenzotriazole or 1-hydroxy-7-azabenzotriazole and reacted with an amine 50 to give an amide 51. The amino group in 51 may be deprotected by a method known in the art and described by e.g. T. W. Greene (Protective Groups in Organic Synthesis, 2. ed., John Wiley and Sons, New York 1991) e.g. hydrogen chloride in ethyl acetate or trifluoroacetic acid. An acid 34a may be activated by e.g. 1-ethyl-3-(3-dimethylaminopropyl)-carbodiimide hydrogenchloride or a combination of 1-ethyl-3-(3-dimethylaminopropyl) carbodiimide hydrogenchloride and 1-hydroxybenzotriazole or 1-hydroxy-7-azabenzotriazole and reacted in an appropriate solvent such as e.g. DMF of dichloromethane with 52 to give the amide 53. The amine-protection group may be removed by a method known in the art and described by e.g. T. W. Greene (Protective Groups in Organic Synthesis, 2. ed., John Wiley and Sons, New York 1991) such as e.g. hydrogenchloride in ethyl acetate or trifluoroacetic acid. A protected acid 37 may be activated by e.g. 1-ethyl-3-(3-dimethylamino-propyl)carbodiimide hydrogenchloride or a combination of 1-ethyl-3-(3-dimethylaminopropyl)carbodiimide hydrogenchloride and 1-hydroxybenzotriazole or 1-hydroxy-7-azabenzotriazole and may be reacted with the amine 54 in an appropriate solvent such -as DMF or dichloromethane to give—after deprotection by a method known in the art and described by e.g. T. W. Greene (Protective Groups in Organic Synthesis, 2. ed., John Wiley and Sons, New York 1991) such as e.g. hydrogen chloride in ethyl acetate or tifluoroacetic acid—55, which is a compound of formula I.

General Method H

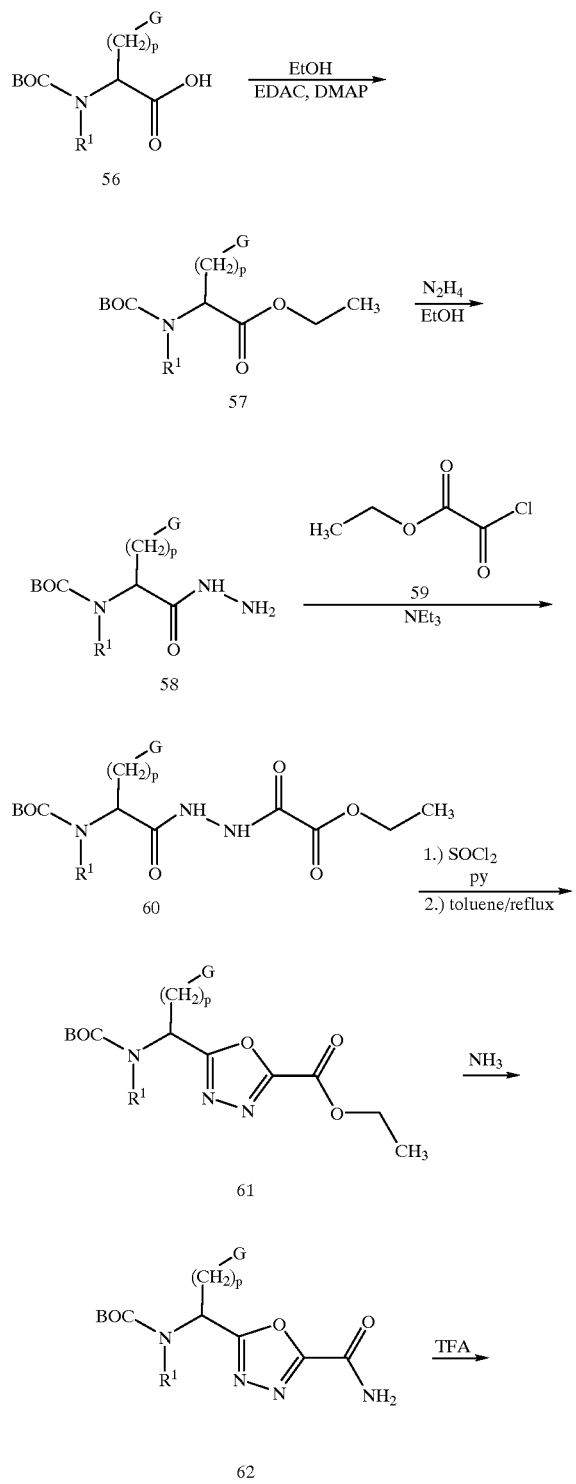

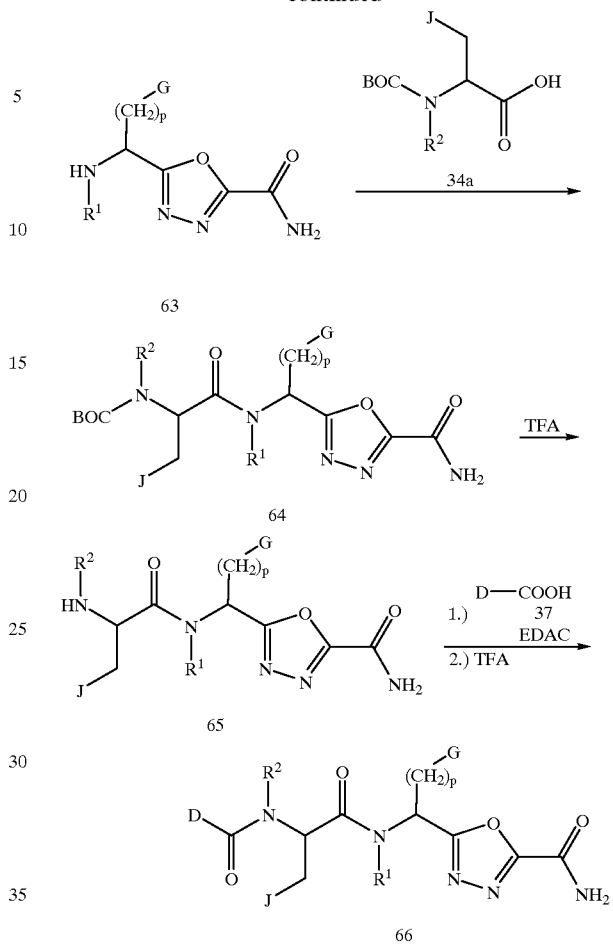

A compound of formula I may be prepared as shown in scheme VIII, starting with an amino acid 56. As described by e.g. S. Borg et al. (J. Org. Chem. 1995, 60, 3112–3120.) 56 may be transformed into an ester 57 by e. g. reaction with ethanol in the presence of N-(3-dimethylaminopropyl)-N'-ethylcarbodiimide hydrochloride and 4-dimethylaminopyridine, which may be subsequently reacted with hydrazine hydrate to give the hydrazide 58. The ester 60 may be obtained from 58 by reaction with ethyl oxalyl cloride (59) in the presence of a base such as e.g. triethylamine. The ring closure may proceed e.g. with thionyl chloride/pyridine and subsequent heat, furnishing and [1,3,4]oxadiazole 61. The amide 62 may be obtained by aminolysis of the ester moiety in e.g. liquid ammonia. Deprotection of the amino group by a method known in the art and described by e.g. T. W. Greene (Protective Groups in Organic Synthesis, 2. ed., John Wiley and Sons, New York 1991.) e. g. hydrogen chloride in ethyl acetate or trifluoroacetic acid may furnish the amine 63. A suitable protected amino acid 34a may be coupled to 63 using a coupling reagent known in the art such as e.g. N-(3-dimethylaminopropyl)-N'-ethylcarbodiimide hydrochloride or a combination of N-(3-dimethylaminopropyl)-N'-ethylcarbodiimide hydrochloride and 1-hydroxybenzotriazole or 1-hydroxy-7-azabenzotriazole to give 64. A deprotection, carried out with a method known in the art and described by e.g. T. W. Green (Protective Groups in Organic Synthesis, 2. ed., John Wiley and Sons, New York 1991.) e. g. hydrogen chloride in ethyl acetate or trifluoracetic acid, may furnish the amine 65. This may be coupled with a coupling reagent known in the art such as e.g. N-(3-dimethylaminopropyl)-N'-ethylcarbodiimide hydrochloride or a combination of N-(3-dimethylaminopropyl)-N'-ethylcarbodiimide hydrochloride and 1-hydroxybenzotriazole or 1-hydroxy-7-azabenzotriazole with a suitable protected amino acid 37 to give—after deprotection with a method known in the art and described by e.g. T. W. Greene (Protective Groups in Organic Synthesis, 2. ed., John Wiley and Sons, New York 1991.) e. g. hydrogen chloride in ethyl acetate or trifluoracetic acid—66, which is a compound of formula I.

General Method J

Scheme IX

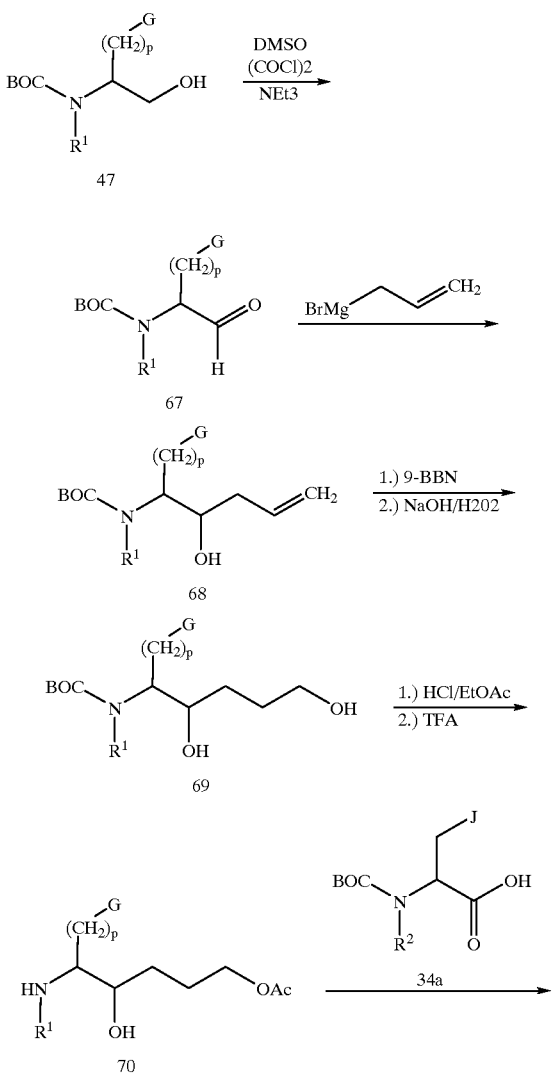

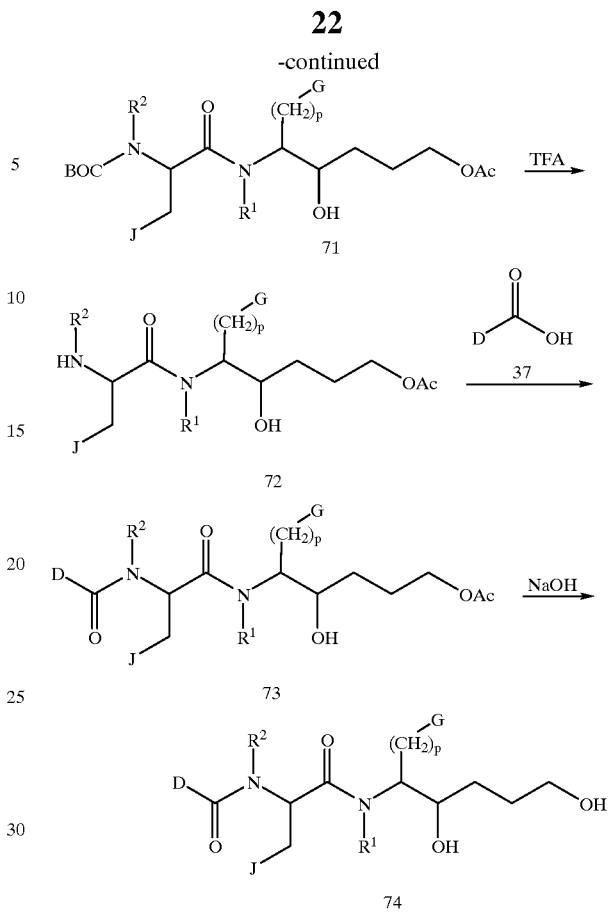

A compound of formula I may be prepared as shown in scheme IX, starting with a suitable protected amino alcohol e.g. 47, which may be oxidized by methods known in the art with reagents such as e.g. DMSO/oxalyl chloride/triethylamine (A. E. DeCamp, A. T. Kawaguchi, R. P. Volante, I. Shinkai, Tetrahedron Letters, 1991, 32, 1867–1870; J. R. Luly, J. F. Dellaria, J. J. Plattner, J. L. Soderquist, N. Yi, J. Org. Chem. 1987, 52, 1487–1492.) or DMSO/sulfur(IV)oxide pyridinium complex/triethylamine (J. S. Ng, C. A. Przybyla, C. Liu, J. C. Yen, F. W. Muellner, C. L. Weyker, Tetrahdron 1995, 51, 6397–6410; P. L. Beaulieu, D. Wernic, J.-S. Duceppe, Y. Guindon, Tetrahedron Letters, 1995, 36, 3317–3320.) to give the aldehyde 67. The aldehyde might be reacted with a Grignard reagent, e.g. allylmagnesium bromide to give an unsaturated compound 68. A hydroboration with e.g. 9-borabicyclo[3.3.1]nonane and subsequent treatment with hydrogen peroxide and sodium hydroxide may furnish the diol 69. The amino group may be deprotected with a method known in the art and described by e.g. T. W. Greene (Protective Groups in Organic Synthesis, 2. ed., John Wiley and Sons, New York 1991) by reaction with e.g. hydrogen chloride in ethyl acetate or trifluoro acetic acid to give 70. A suitable protected amino acid 34a may be coupled to 70 using a coupling reagent known in the art such as e.g. 1-ethyl-3-(3-dimethylaminopropyl)carbodiimid hydrochloride or a combination of 1-ethyl-3-(3-dimethylaminopropyl)carbodiimid hydrochloride and 1-hydroxybenzotriazole or 1-hydroxy-7-azabenzotriazole in an appropriate solvent such as e.g. DMF of dichloromethane to give 71. A deprotection carried out with a method known in the art and described by e.g. T. W. Greene (Protective Groups in organic Synthesis, 2. ed., John Wiley and Sons, New York 1991) e.g. trifluoro acetic acid may furnish the amine 72. A suitable protected amino acid 37 may be coupled to 72 with a coupling reagent known in the art such as e.g. 1-ethyl-3-(3-dimethylaminopropyl) carbodiimid hydrochloride or a combination of 1-ethyl-3-(3-dimethylaminopropyl)carbodiimid hydrochloride and 1-hydroxybenzotriazole or 1-hydroxy-7-azabenzotriazole in an appropriate solvent such as e.g. DMF of dichloromethane to give—after deprotection with a method known in the art and described by e.g. T. W. Greene (Protective Groups in Organic Synthesis, 2. ed., John Wiley and Sons, New York 1991) by reaction with e.g. trifluoro actic acid—73. 73 may be saponified by a method known in the art and described by e.g. T. W. Greene (Protective Groups in Organic Synthesis, 2. ed., John Wiley and Sons, New York 1991) by reaction with e.g. potassium hydroxide or sodium hydroxide to give 74, which is a compound of formula I.

General Method K

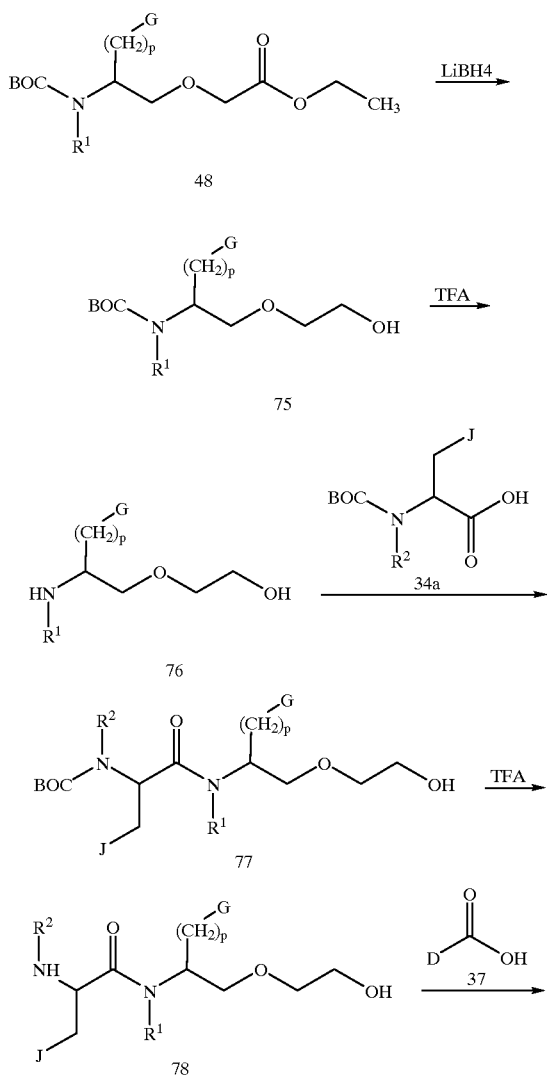

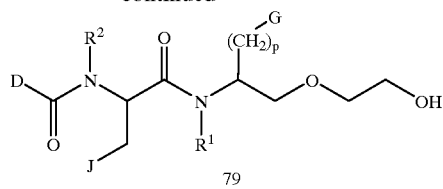

The ether 48 may be reduced with a method known in the art e.g. lithium boronhydride, sodium borohydride, or diisobutylaluminum hydride to give an alcohol 75. The amino group may be deprotected by a method known in the art and described by e.g. T. W. Greene (Protective Groups in Organic Synthesis, 2. ed., John Wiley and Sons, New York 1991)by reaction with e.g. hydrogen chloride in ethyl acetate or trifluoro acetic acid to give the amine 76. A suitable protected amino acid 34a may be coupled to 76 using a coupling reagent known in the art such as e.g. 1-ethyl-3-(3-dimethylaminopropyl)carbodiimid hydrochloride or a combination of 1-ethyl-3-(3-dimethylaminopropyl) carbodiimid hydrochloride and 1-hydroxybenzotriazole or 1-hydroxy-7-azabenzotriazole in an appropriate solvent such as e.g. DMF of dichloromethane to give 77. A deprotection carried out with a method known in the art and described by e.g. T. W. Greene (Protective Groups in Organic Synthesis, 2. ed., John Wiley and Sons, New York 1991) e.g. trifluoro acetic acid or hydrogen chloride in ethyl acetate may furnish the amine 78. A suitable protected amino acid 37 may be coupled to 78 with a coupling reagent known in the art such as e.g. 1-ethyl-3-(3-dimethylaminopropyl)carbodiimid hydrochloride or a combination of 1-ethyl-3-(3-dimethylaminopropyl) carbodiimid hydrochloride and 1-hydroxybenzotriazole or 1-hydroxy-7-azabenzotriazole in an appropriate solvent such as e.g. DMF or dichloromethane to give—after deprotection with a method known in the art and described by e.g. T. W. Greene (Protective Groups in Organic Synthesis, 2. ed., John Wiley and Sons, New York 1991) by reaction with e.g. trifluoro actic acid—79, which is a compound of formula I. To enhance the yield, it may be feasible to subject the crude product to a saponification with reagents known in the art and described by e.g. T. W. Greene (Protective Groups in Organic Synthesis, 2. ed., John Wiley and Sons, New York 1991) such as e.g. potassium hydroxide in methanol to cleave esters, that may have formed during the amide coupling steps.

General Method L

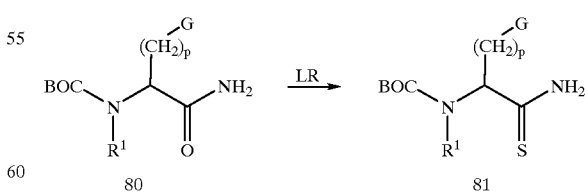

Thioamides 81 can be incorporated by the same methods as in method K. They can be made from the corresponding amides 80 by the action of Lawesson's reagent (LR). This methodology is described in S. Scheiby, B. S. Pedersen, S. O. Lawesson, Bull. Chim. Soc. Belg., 1978, 229–38.

General Method M

Scheme XII

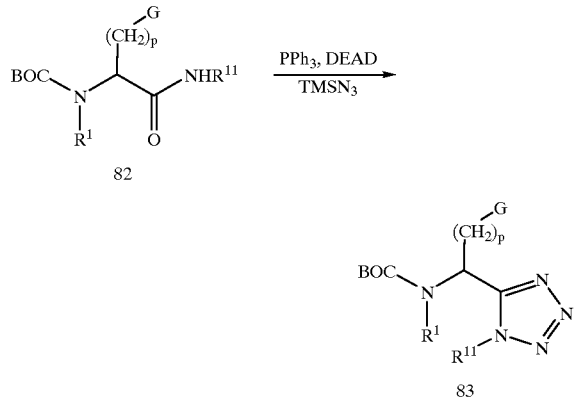

Tetrazole analogs 83 of amides 82 can be incorporated by much the same methods as in method K. They may be prepared by the action of triphenylphosphine, diethylazodicarboxylate and trimethylsilylazide on amides like 82. This methodology is described in J. V. Dunica, M. E. Pierce, J. B. Santella III, J. Org. Chem. 1991, 56, 2395–2400.

General Method N

Scheme XIII

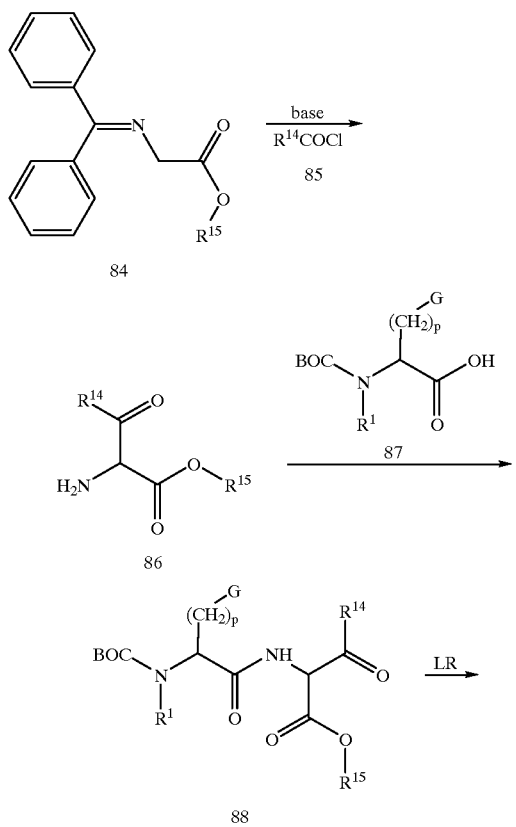

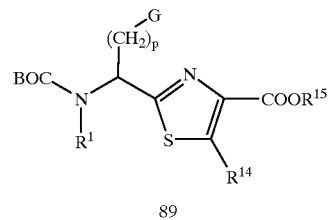

Thiazoles 89 may be incorporated by the same methodology as in method F. 89 may be synthesized by acylation of the imine 84 using a strong base such as potassium tert butoxide or lithium diisopropylamide and an acylating reagent such as an acid chloride 85. The resulting 3-keto-aminoacid 86 could be coupled to the dipeptide 88 by known methods such as the asymmetrical anhydride method using a reagent such as isobutylchloroformate as coupling agent. The dipeptide 88 could be cyclised by a number of methods e.g. with Lawessons reagent (LR) to give the desired thiazoles 89. This methodology has been described in T. D. Gordon, J. Singh, P. H. Hansen, B. A. Morgan, Tett. Lett., 1993, 1901–1904.

Pharmaceutically acceptable acid addition salts of compounds of formula I include those prepared by reacting the compound with an inorganic or organic acid such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoracetic, sulfamic or fumaric acid.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9–40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.1–500 mg/day, e.g. from about 5 to about 50 mg, such as about 10 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, prevention and treatment of osteoporosis, stimulation of the immune system, acceleration of wound healing, accelerating bone fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures.

The isolation of rat pituitary cells is a modification of O. Sartor et al., *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 µg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipet, the tissue was then aspirated into single cells. After dispersion, cells were filtered through a nylon filter (160 µm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 µg/L dexamethasone (Sigma D-4902) pH 7.3, to a density of $2 \times 10^5$ cells/ml. The cells were seeded into microtiter plates (Nunc, Denmark), 200 µl/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 µl stimulation buffer (37° C.). Ten µl test compound solution was added and the plates were incubated for 15 min at 37° C. and 5% $CO_2$. The medium was decanted and analyzed for GH content in an rGH SPA test system.

All compounds were tested in doses ranging from 10 pM to 100 µM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability.

Compounds were dissolved at a concentration of 1 µg/µl in water. 25 µl of this solution is added to 175 µl of the respective enzyme-solution (resulting in an enzyme:substrate ratio (w/w) of approximately 1:5). The solution is left at 37° C. overnight. 10 µl of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4–10, Angiotensin 1–14 and Glucagon) have been included in the stability tests in order to verify the ability of the various solutions to degrade peptides.

Standard peptides (angiotensin 1–14, ACTH 4–10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 µg/µl).

Carboxypeptidase mix: carboxypeptidase Y and B in 50 mM ammoniumacetate pH 4.5 (all concentrations 0.025 µg/µl).

Aminopeptidase M solution: aminopeptidase M (0.025 µg/µl) in 100 mM ammoniumbicarbonate pH 8.0.

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 µl/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. enzyme mix |
| --- | --- | --- | --- |
| Standards | | | |
| ACTH 4–10 | 1124.5/562.8 | + | − |
| Glucagon | 3483/871.8 | − | − |
| Insulin (B23–29) | 859.1/430.6 | | |
| Angiotensin 1–14 | 1760.1/881.0 | − | − |
| GHRP-2 | 817.4/409.6 | − | − |
| GHRP-6 | 872.6/437.4 | − | − |

+ Stable (less than 20% decrease in SIM signal after 24 h in degradation solution)
− Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following exampels, which however, are not to be construed as limiting.

The structures of the. compounds are confirmed by either elemental analysis (MA) nuclear magnetic resonance (NMR) or mass spectrometry (MS). NMR shifts (δ) are given in parts per million (ppm) and only selected peaks are given. mp is melting point and is given in ° C. Column chromatography was carried out using the technique described by W. C. Still at al, J. Org. Chem. 1978, 43, 2923–2925 on Merck silica gel 60 (Art 9385). Compounds used as starting materials are either known compounds or compounds which can readily be prepared by methods known per se.

Abbrevations:
TLC: thin layer chromatography
DMSO: dimethylsulfoxide
min: minutes
h: hours
ESMS=Electro Spray Mass Spectrometry
PDMS=Plasma Desorption Mass Spectrometry
HPLC-Analysis:

Method a

The RP-HPLC analysis was performed using UV detection at 254 nm and a Lichrosorp RP-18 5 μM column, which was eluted at 1 ml/minute. Two solvent systems were used:

Solvent system I: 0.1% Trifluoroacetic acid in acetonitrile.

Solvent system II: 0.1% Trifluoroacetic acid in water.

The column was equilibrated with a mixture composed of 20% of solvent system I and 80% of solvent system II. After injection of the sample a gradient of 20% to 80% of solvent system I in solvent system II was run over 30 min. The gradient was then extended to 100% of solvent system I over 5 min. followed by isocratic elution with 100% of this system for 6 min.

Method b

The RP-analysis was performed using UV detections at 214, 254, 276, and 301 nm on a 218TP54 4.6 mm×250 mm 5μ C-18 silica column (The Seperations Group, Hesperia), which was eluted at 1 mL/min at 42° C. The column was equilibrated with 5% acetonitrile in a buffer consisting of 0.1 M ammonium sulfate, which was adjusted to pH 2.5 with 4M sulfuric acid. After injection the sample was eluted by a gradient of 5% to 60% acetonitrile in the same buffer during 50 min.

Example 1

(3R)-Piperidine 3-carboxylic acid [(1R)-1-((1R)-1-(3-methyl-[1,2,4]oxadiazol-5-yl)-2-phenylethylcarbamoyl)-2-(2-naphthyl)ethyl]amide

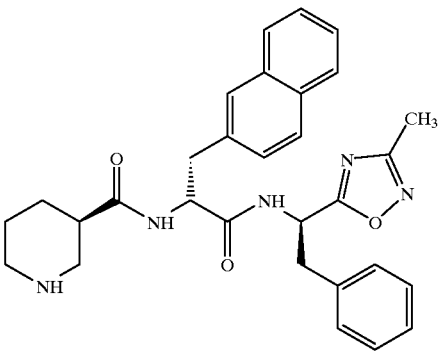

Prepared according to method E.

(R) [1-(3-Methyl-[1,2,4]oxadiazol-5-yl)-2-phenylethyl]carbamic acid tertbutyl ester

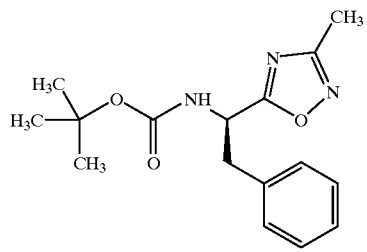

1,3-Dicyclohexylcarbodiimide (10.1 g, 49 mmol) was dissolved in dichloromethane (100 ml) and added to a solution of (R) N-tert-butoxycarbonyl-phenylalanine (10.0 g, 37.7 mmol) in dichloromethane (250 ml) at 0–5° C. The reaction mixture was heated to 20° C. and stirred at this temperature for 1 h. Acetamide oxime (3.63 g, 49 mmol) was suspended in pyridine (200 ml) and N,N-dimethylformamide (40 ml) and added to the reaction mixture. The dichloromethane was evaporated and the reaction mixture was heated at reflux temperature for 18 h. The reaction mixture was cooled to 0° C. and filtered. The filtrate was diluted with ethyl acetate (100 ml) and washed with aqueous citric acid (10%, 3×50 ml) and water (3×50ml). After drying (magnesium sulfate) the solution was concentrated in vacuo and crystallized from ethyl acetate and heptane to give 5.48 g of (R) [1-(3-methyl-[1,2,4]oxadiazol-5-yl)-2-phenylethyl]carbamic acid tertbutyl ester.

mp 94–98° C.

$^1$H-NMR (DMSO-$d_6$) δ1.30(s, 9H); 2.32(s, 3H); 4.90–5.10(m, 1H); 7.15–7.30(m, 5H).

HPLC: $R_t$=26.7 min (Method a)

(R) 1-(3-Methyl-[1,2,4]oxadiazol-5-yl)-2-phenylethylamine hydrochloride

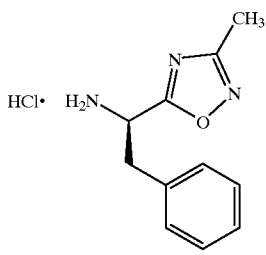

(R) [1-(3-methyl-[1,2,4]oxadiazol-5-yl)-2-phenylethyl]carbamic acid tertbutyl ester (2.4 g, 7.9 mmol) was dissolved in a saturated solution of hydrogen chloride in ethyl acetate (40 ml). After 5 h at 20° C. the reaction mixture was concentrated in vacuo. The residue was crystallized from ethyl acetate to give 2.05 g of (R) 1-(3-methyl-[1,2,4]oxadiazol-5-yl)-2-phenylethylamine hydrochloride.

m.p. 144–148° C.

$^1$H-NMR (DMSO-d$_6$) δ2.35(s, 3H); 3.21(dd, 1H); 3.49 (dd, 1H); 5.05(dd, 1H); 7.13–7.35(m, 5H).

HPLC: R$_t$=9.2 min (Method a)

{(1R)-1-{(1R)-1-(3-Methyl-[1,2,4]oxadiazol-5-yl)-2-phenylethylcarbamoyl}-2-(2-naphthyl)ethyl}carbamic acid tertbutyl ester

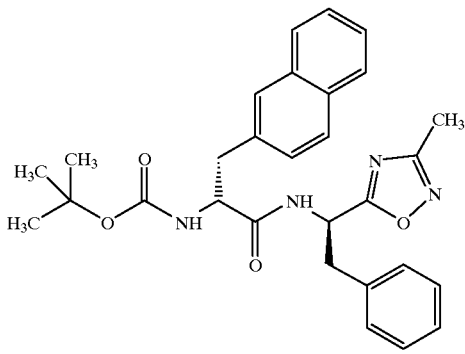

N-(3-Dimethylaminopropyl)-N'-ethylcarbodiimide hydrochloride (6.3 g, 32.9 mmol) and 1-hydroxybenzotriazole monohydrate (5.0 g, 32.9 mmol) were added to a solution of (R) N-tert-butoxycarbonyl-3-(2-naphthyl)-alanine (10.4 g, 32.9 mmol) in N,N-dimethylformamide (140 ml). After 1 h at 20° C. a mixture of 1-(3-methyl-[1,2,4]oxadiazole-5-yl)-2-phenylethylamine hydrochloride (5.6 g, 23.5 mmol) and triethylamine (2.37 g, 23.5 mmol) in N,N-dimethylformamide (100 ml) were added. After 18 h at 20° C. the reaction mixture was poured onto water (1.4 L) and extracted several times with ethyl acetate (total 1.4 L). The combined organic phases were washed with aqueous citric acid (10%, 200 ml), a saturated solution of sodium hydrogencarbonate (200 ml) and water (3×200 ml). After drying (magnesium sulfate) the solution was concentrated in vacuo and crystallized from ethyl acetate and heptane to give 9.45 g of {(1R)-1-{(1R)-1-(3-methyl-[1,2,4]oxadiazol-5-yl)-2-phenylethylcarbamoyl}-2-(2-naphthyl)ethyl}carbamic acid tertbutyl ester.

m.p. 148–150° C.

$^1$H-NMR (DMSO-d$_6$) δ1.25(s, 9H); 2.29(s, 3H); 4.25–4.35(m, 1H); 5.25–5.35 (s, 1H); 7.15–7.85 (m, 12H).

HPLC: R$_t$=29.6 min (Method a)

Calculated for C$_{29}$H$_{32}$N$_4$O$_4$:

C, 69.58; H, 6.44; N, 11.19%; found:

C, 69,40; H, 6.65; N, 10.93%.

(2R)-2-Amino-N-[(1R)-1-(3-methyl-[1,2,4]oxadiazol-5-yl)-2-phenylethyl]-3-(2-naphthyl)propionamide hydrochloride

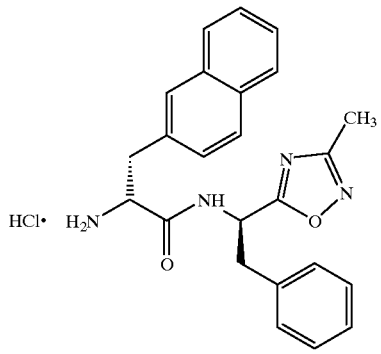

{(1R)-1-{(1R)-1-(3-Methyl-[1,2,4]oxadiazol-5-yl)-2-phenylethylcarbamoyl}-2-(2-naphthyl)ethyl}carbamic acid tertbutyl ester (4.5 g, 8.99 mmol) was suspended in ethyl acetate (50 ml) and a saturated mixture of hydrogen chloride in ethyl acetate (45 ml) was added. After 3 h at 20° C., the reaction mixture was filtered to give 3.17 g of (2R)-2-amino-N-[(1R)-1-(3-methyl-[1,2,4]oxadiazol-5-yl)-2-phenylethyl]-3-(2-naphthyl)propionamide hydrochloride.

mp 197–199° C.

$^1$H-NMR (DMSO-d$_6$) δ2.28(s, 3H); 3.15–3.35(m, 4H); 4.15(t, 1H); 5.35(q, 1H); 7.20–7.90(m, 12H).

HPLC: R$_t$=18.5 min (Method a)

Calculated for C$_{24}$H$_{24}$N$_4$O$_2$,HCl:

C, 65.97; H, 5.77; N, 12.82%; found:

C, 66,20; H, 5.90; N, 12.57%.

(3R)-3-{(1R)-1-[(1R)-1-(3-Methyl-[1,2,4]oxadiazol-5-yl)-2-phenylethylcarbamoyl]-2-(2-naphthyl)ethylcarbamoyl}piperidine-1-carboxylic acid tertbutyl ester

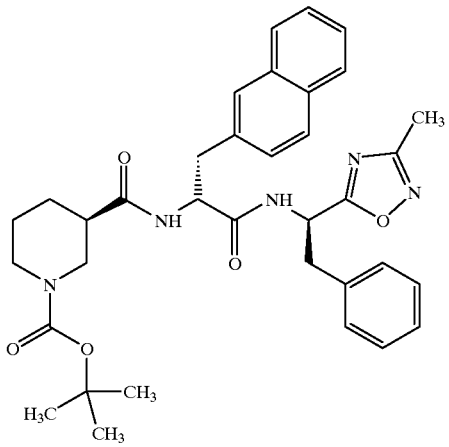

N-(3-Dimethylaminopropyl)-N'-ethylcarbodiimide hydrochloride (0.42 g, 2.18 mmol) and 1-hydroxybenzotriazole monohydrate (0.33 g, 2.18 mmol) were added to a solution of (R)-N-tertbutoxycarbonyl-3-piperidine carboxylic acid (0.50 g, 2.18 mmol) in N,N-dimethylformamide (7 ml). After 30 min at 20° C. a mixture of (2R)-2-amino-N-[(1R)-1-(3-methyl-[1,2,4]oxadiazol-5-yl) -2-phenylethyl]-3-(2-naphthyl)propionamide hydrochloride (0. 68 g, 1.56 mmol) and triethylamine (0. 16 g, 1. 56 mmol) in N,N-dimethylformamide (8 ml) was added. After 18 h at 20° C. the reaction mixture was poured on ice water (90 ml) and extracted several times with ethyl acetate (total 90 ml). The organic phases were collected and washed with aqueous citric acid (10%, 15 ml), a saturated solution of sodium hydrogencarbonate (3×15 ml) and water (3×15 ml). After drying (magnesium sulfate) the solution was concentrated in vacuo and purified by flash chromatography on silica gel (90 g) using ethyl acetate and heptane (3:2) as eluent to give 0. 83 g of (3R)-3-{(1R)-1-[(1R)-1-(3-methyl-[1,2,4]oxadiazol-5-yl)-2-phenylethylcarbamoyl]-2-(2-naphthyl)ethylcarbamoyl}piperidine-1-carboxylic acid tert-butyl ester.

$^1$H-NMR (DMSO-$d_6$) δ1.37(s, 9H); 2.30(s, 3H); 4.60–4.70(m, 1H); 5.25–5.35(m, 1H); 7.15–7.85(m, 12H).

HPLC: $R_t$=31.6 min (Method a)

3-{(1R)-[(1R)-1-(3-Methyl-[1,2,4]oxadiazol-5-yl)-2-phenylethylcarbamoyl]-2-(2-naphthyl)ethylcarbamoyl}piperidine-1-carboxylic acid tertbutyl ester (0.80 g, 1.31 mmol) was dissolved in ethyl acetate (20 ml) and a saturated solution of hydrogen chloride in ethyl acetate (20 ml) was added. After 2 h at 20° C. the reaction mixture was concentrated in vacuo. The compound was crystallized from a mixture of methanol and ethyl acetate to give 0.66 g of the title compound.

m.p. 198–200° C.

$^1$H-NMR (DMSO-$d_6$) δ1.10–1.80(m, 4H); 2.30(s, 3H); 4.60–4.70(m, 1H) 5.25–5.35(m, 1H); 7.20–7.90(m, 12H).

HPLC: $R_t$=20.9 min (Method a)

Calculated for $C_{30}H_{33}N_5O_5$,HCl:

C, 65.74; H, 6.25; N, 12.78%; found:

C, 65,57; H, 6.35; N, 12.46%.

Example 2

4-Amino-4-methyl-pent-2-enoic acid [(1R)-1-{(1R)-1-(3-methyl-[1,2,4]oxadiazol-5-yl)-2-phenylethylcarbamoyl}-2-(2-naphthyl)ethyl]amide

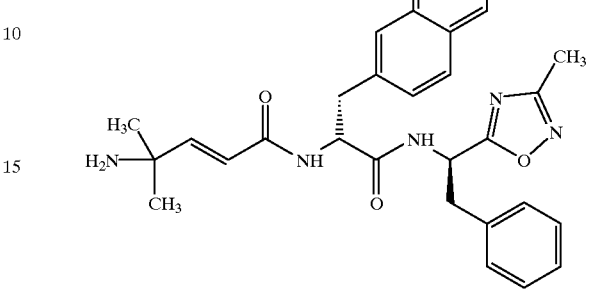

Prepared according to method E.

N-2-Hydroxy-1,1-dimethylethyl carbamic acid tert-butyl ester

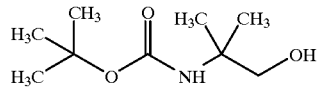

2-Amino-2-methylpropan-1-ol (10.0 g, 112 mmol) was dissolved in tetrahydrofuran (100 ml). A 1N solution of sodium hydroxide in water (112 ml, 112 mmol) was added. A solution of di-tert-butyl dicarbonate (29.3 g, 134 mmol) in tetrahydrofuran (100 ml) was added over a period of 15 min. The solution was stirred at 20° C. for 16 h. Water (100 ml) was added. The phases were separated. The aqueous phase was extracted with ethyl acetate (3×150 ml) and the combined organic phases were dried (magnesium sulfate). The solvent was removed in vacuo and the crude product was chromatographed on silica gel (180 g) with ethyl acetate/heptane 1:1 as eluent to give 19.6 g of N-2-hydroxy-1,1-dimethylethyl carbamic acid tert-butyl ester.

mp 53° C.

$^1$H-NMR (CDCl$_3$): δ1.22 (s, 6 H); 1.45 (s, 9 H); 3.58 (d, 2 H),; 4.05 (br, 1 H); 4.65 (br, 1 H).

2-tert-Butoxycarbonylamino-2-methylpropanal

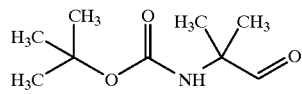

DMSO (12.4 ml, 174.4 mmol) was dissolved in dichloromethane (240 ml) and the solution was cooled to −78° C. Oxalyl chloride (7.6 ml, 87 mmol) was added dropwise. The solution was stirred at −78° C. for 15 min. A solution of N-2-hydroxy-1,1-dimethylethyl carbamic acid tert-butyl ester in dichloromethane (30 ml) was added dropwise. The solution was stirred for 30 min at −78° C. Triethylamine (55.23 ml, 396.3 mmol) was added slowly. After 5 min at −78° C. the solution was allowed to warm to 20° C., diluted with dichloromethane (300 ml) and washed with 1N hydrochloric acid (3×200 ml). The combined aqueous phases were extracted with dichloromethane (2×200 ml). The combined organic layers were washed with a saturated solution of sodium hydrogencarbonate (2×200 ml) and dried (magnesium sulfate). The solvent was removed in vacuo and the crude product was chromatographed on silica gel (180 g) with ethyl acetate/heptane 1:4 as eluent to give 13.4 g of 2-tert-butoxycarbonylamino-2-methylpropanal.

mp 84–85° C.

$^1$H-NMR (CDCl$_3$) δ1.35 (s, 6 H); 1.45 (s, 9 H); 5.00 (br, 1H) 9.45 (s, 1 H).

(2E)-4-tert-Butoxycarbonylamino-4-methylpent-2-enoic acid ethyl ester

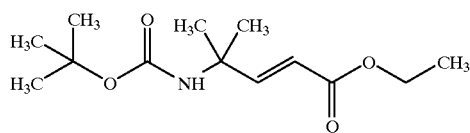

Triethyl phosphonoacetate (9.6 ml, 48 mmol) was added slowly to a suspension of potassium tert-butoxide (5.39 g, 48 mmol) in tetrahydrofuran (140 ml). After 30 min at 20° C. 2-tert-butoxycarbonylamino-2-methylpropanal (5.0 g, 26 mmol) was added. After 2.5 h at 20° C. 1N hydrochloric acid (80 ml) was added slowly. The mixture was extracted with ethyl acetate (120 ml, 2×50 ml) and the combined organic layers were washed with a saturated solution of sodium hydrogencarbonate (100 ml) and dried (magnesium sulfate). The solvent was removed in vacuo and the crude product was chromatographed on silica gel (100 g) with ethyl acetate/heptane 1:4 as eluent to give 5.7 g of (2E)-4-tert-butoxycarbonylamino-4-methylpent-2-enoic acid ethyl ester.

mp 40–41° C. (Heptane)

$^1$H-NMR (CDCl$_3$): δ1.29 (t, 3 H); 1.41 (s, 6 H); 1.43 (s, 9H); 4.19 (q, 2 H); 4.65 (br, 1H); 5.84 (d, J=15.9 Hz, 1 H); 6.99 (d, J=16.0 Hz, 1 H).

(2E)-4-tert-Butoxycarbonylamino-4-methylpent-2-enoic acid

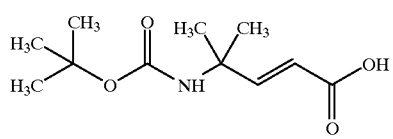

(2E)-4-tert-Butoxycarbonylamino-4-methylpent-2-enoic acid ethyl ester (5.0 g, 19.4 mmol) was dissolved in dioxane (50 ml). A solution of lithium hydroxide (0.61 g, 25.3 mmol) in water (25 ml) was added. The solution was stirred for 16 h at 20° C. Ethyl acetate (75 ml) and water (20 ml) were added. The phases were seperated, and the aqueous phase was extracted with ethyl acetate (20 ml). The combined organic phases were extracted with 1N sodium hydroxide solution (30 ml). The combined aqueous phases were acidified with iN sodium hydrogensulfate solution until pH=2. The aqueous phase was extracted with ethyl acetate (2×50 ml). The combined organic phases were dried (magnesium sulfate) and the solvent removed in vacuo. The crude (2E)-4-tert-butoxycarbonylamino-4-methylpent-2-enoic acid was used for further syntheses.

$^1$H-NMR (CDCl$_3$): δ1.39 (s, 6 H); 1.43 (s, 9 H); 4.79 (br, 1 H); 5.75 (d, 1 H); 7.12 (d, 1 H); 9.50–11.50 (br, 1 H).

{1,1-Dimethyl-3-[(1R)-1-((1R)-1-(3-methyl-[1,2,4] oxadiazol-5-yl)-2-phenylethylcarbamoyl)-2-(2-naphthyl)ethylcarbamoyl]-allyl}carbamic acid tertbutyl ester

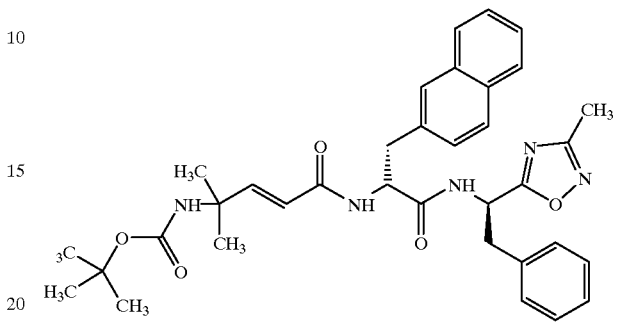

N-(3-Dimethylaminopropyl)-N'-ethylcarbodiimide hydrochloride (0.42 g, 2.18 mmol) and 1-hydroxybenzotriazole monohydrate (0.33 g, 2.18 mmol) were added to a solution of 4-tertbutoxycarbonylamino-4-methylpent-2-enoic acid (0.50 g, 2.18 mmol) in N,N-dimethylformamide (7 ml). After 30 min at 20° C. a mixture of (2R)-2-amino-N-[(1R)-1-(3-methyl-[1,2,4]oxadiazol-5-yl)-2-phenylethyl]-3-(2-naphthyl)propionamide hydrochloride (0.68 g, 1.56 mmol) and triethylamine (0.16 g, 1.56 mmol) in N,N-dimethylformamide (8 ml) were added. After 18 h at 20° C. the reaction mixture was poured on ice water (90 ml) and extracted several times with ethyl acetate (total 90 ml). The organic phases were collected and washed with aqueous citric acid (10%, 15 ml), a saturated solution of sodium hydrogencarbonate (3×15 ml) and water (3×15 ml). After drying (magnesium sulfate) the solution was concentrated in vacuo and purified by flash chromatography on silica gel (95 g) using ethyl acetate and heptane (1:1) as eluent to give 0.90 g of {1,1-dimethyl-3-[(1R)-1-((1R)-1-(3-methyl-[1,2,4]oxadiazol-5-yl)-2-phenylethylcarbamoyl)-2-(2-naphthyl)ethylcarbamoyl]allyl}carbamic acid tertbutyl ester.

$^1$H-NMR (DMSO-d$_6$) δ1.22(s, 3H); 2.28(s, 3H); 4.70–4.80(m, 1H); 5.72–5.82(m, 1H); 5.89(d, 1H); 6.72(d, 1H); 7.15–7.85(m, 12H).

HPLC: R$_t$=30.3 min (Method a)

{1,1-Dimethyl-3-[(1R)-1-((1R)-1-(3-methyl-[1,2,4] oxadiazol-5-yl) -2-phenylethylcarbamoyl)-2-(2-naphthyl) ethylcarbamoyl]-allyl}carbamic acid tertbutyl ester (0.90 g, 1.47 mmol) was dissolved in ethyl acetate (10 ml) and a saturated solution of hydrogen chloride in ethyl acetate (20 ml) was added. After 3 h at 20° C. the reaction mixture was concentrated in vacuo to give 0.70 g of the title compound.

mp 161–167° C.

$^1$H-NMR (DMSO-d$_6$) δ1.32(s, 3H); 1.34(s, 3H); 2.28(s, 3H); 4.75–4.83(m, 1H); 5.23–5.33(m, 1H); 6.12(d, 1H); 6.61(d, 1H); 7.15–7.88(m, 12H).

HPLC: R$_t$=20.6 min (Method a)

Calculated for C$_{30}$H$_{33}$N$_5$O$_5$,HCl,0.75 H$_2$O:

C, 64.16; H, 6.45; N, 12.47%; found:

C, 64,42; H, 6.43; N, 12.03%.

Example 3

3-Aminomethyl-N-[(1R)-1-{(1R)-1-(3-methyl-[1,2,4]oxadiazol-5-yl)-2-phenylethylcarbamoyl}-2-(2-naphthyl)ethyl]benzamide

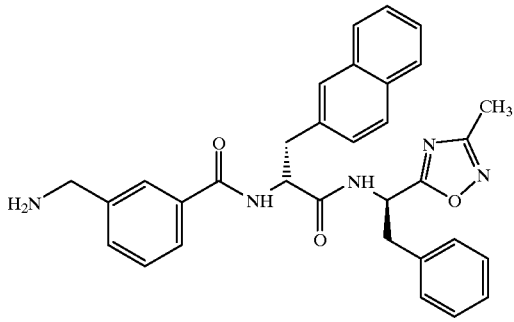

Prepared according to method E.

(3-{(1R)-1-[(1R)-1-(3-Methyl-[1,2,4]oxadiazol-5-yl)-2-phenylethylcarbamoyl]-2-(2-naphthyl)ethylcarbamoyl}-benzyl)carbamic acid tertbutyl ester

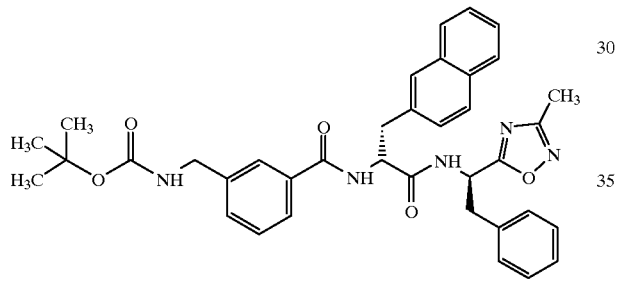

N-(3-Dimethylaminopropyl)-N'-ethylcarbodiimide hydrochloride (0.92 g, 4.82 mmol) and 1-hydroxybenzotriazole monohydrate (0.74 g, 4.83 mmol) were added to a solution of N-tertbutoxycarbonyl-3-aminobenzoic acid (1.21 g, 4.82 mmol) in N,N-dimethylformamide (15 ml). After 1 h at 20° C. a mixture of (2R)-2-amino-N-[(1R)-1-(3-methyl-[1,2,4]oxadiazol-5-yl)-2-phenylethyl]-3-(2-naphthyl)propionamide hydrochloride (1.50 g, 3.43 mmol) and triethylamine (0.35 g, 3.46 mmol) in N,N-dimethylformamide (15 ml) were added. After 18 h at 20° C. the reaction mixture was poured on ice water (180 ml) and extracted several times with dichloromethane (total 180 ml). The organic phases were collected and washed with aqueous citric acid (10%, 25 ml), a saturated solution of sodium hydrogencarbonate (3×25 ml) and water (3×25 ml). After drying (magnesium sulfate) the solution was concentrated in vacuo and 1.80 g of (3-{(1R)-1-[(1R)-1-(3-methyl-[1,2,4]oxadiazol-5-yl)-2-phenylethylcarbamoyl]-2-(2-naphthyl)ethylcarbamoyl}-benzyl)carbamic acid tertbutyl ester was isolated from ethyl acetate.

mp=176–178° C.

$^1$H-NMR (DMSO-$d_6$) δ1.39(s, 9H); 2.30(s, 3H); 4.70–4.80(m, 1H); 5.29–5.39(m, 1H); 7.15–7.85(m, 17H).

HPLC: $R_t$=31.4 min (Method a)

Calculated for $C_{37}H_{39}N_5O_5$:
C, 70.12; H, 6.20; N, 11.05%; found:
C, 70.20; H, 6.34; N, 10.86%.

(3-{(1R)-1-[(1R)-1-(3-Methyl-[1,2,4]oxadiazol-5-yl)-2-phenylethylcarbamoyl]-2-(2-naphthyl)ethylcarbamoyl}-benzyl)carbamic acid tertbutyl ester (5.51 g, 2.38 mmol) was suspended in ethyl acetate (20 ml) and a saturated solution of hydrogen chloride in ethyl acetate (30 ml) was added. After 4 h at 20° C. the reaction mixture was concentrated in vacuo and crystallized from ethyl acetate to give 1.26 g of the title compound.

mp 240–241° C.

$^1$H-NMR (DMSO-$d_6$) δ2.31(s, 3H); 4.03(s, 2H); 4.75–4.85(m, 1H); 5.38–5.48(m, 1H); 7.15–7.90(m, 16H).

HPLC: $R_t$=24.6 min (Method a)

Calculated for $C_{32}H_{31}N_5O_3$,HCl:
C, 67.42; H, 5.66; N, 12.28%; found:
C, 67.26; H, 5.76; N, 12.00%.

Example 4

Piperidine 4-carboxylic acid N-[(1R)-1-{(1R)-1-(3-methyl-[1,2,4]oxadiazol-5-yl)-2-phenylethylcarbamoyl}-2-(2-naphthyl)ethyl]amide

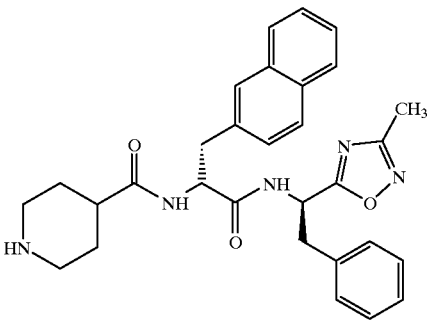

Prepared according to method E.

4-{(1R)-1-[(1R)-1-(3-Methyl-[1,2,4]oxadiazol-5-yl)-2-phenylethylcarbamoyl]-2-(2-naphthyl)ethylcarbamoyl}piperidine-1-carboxylic acid tertbutyl ester

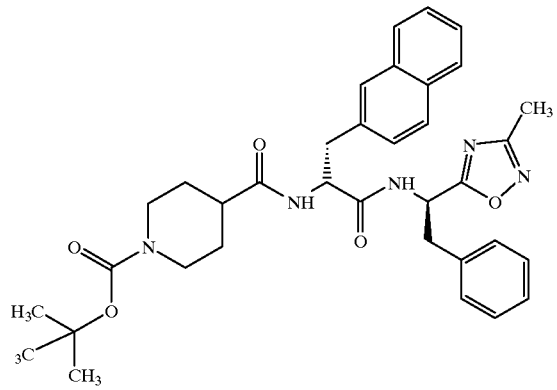

N-(3-Dimethylaminopropyl)-N'-ethylcarbodiimide hydrochloride (0.92 g, 4.82 mmol) and 1-hydroxybenzotriazole monohydrate (0.74 g, 4.83 mmol) were added to a solution of N-tertbutoxycarbonyl-4-piperidine carboxylic acid (1.10 g, 4.80 mmol) in N,N- dimethylformamide (15 ml). After 30 min at 20° C. a mixture of (2R)-2-amino-N-[(1R)-1-(3-methyl-[1,2,4] oxadiazol-5-yl)-2-phenylethyl]-3-(2-naphthyl) propionamide hydrochloride (1.50 g, 3.43 mmol) and triethylamine (0.35 g, 3.46 mmol) in N,N-dimethylformamide (15 ml) were added. After 18 h at 20° C. the reaction mixture was poured on ice water (180 ml) and extracted several times with ethyl acetate (total 180 ml). The organic phases were collected and washed with aqueous citric acid (10%, 25 ml), a saturated solution of sodium hydrogencarbonate (3×25 ml) and water (3×25 ml). After drying (magnesium sulfate) the solution was concentrated in vacuo and crystallized from ethyl acetate to give 1.84 g of 4-{(1R)-1-[(1R)-1-(3-methyl-[1,2,4]oxadiazol-5-yl)-2-phenylethylcarbamoyl]-2-(2-naphthyl) ethylcarbamoyl}piperidine-1-carboxylic acid tertbutyl ester.

mp 152–155° C.

$^1$H-NMR (DMSO-$d_6$) δ1.35(s, 9H); 2.29(s, 3H); 4.60–4.70(m, 1H); 5.25–5.35(m, 1H); 7.15–7.85(m, 12H).

HPLC: $R_t$=31.3 min (Method a)

Calculated for $C_{35}H_{41}N_5O_5$:

C, 68.72; H, 6.76; N, 11.45%; found:

C, 68.65; H, 6.95; N, 11.34%.

4-{(1R)-1-[(1R)-1-(3-Methyl-[1,2,4]oxadiazol-5-yl)-2-phenylethylcarbamoyl]-2-(2-naphthyl) ethylcarbamoyl}piperidine-1-carboxylic acid tertbutyl ester (1.57 g, 2.57 mmol) was dissolved in ethyl acetate (20 ml) and a saturated solution of hydrogen chloride in ethyl acetate (30 ml) was added. After 4 h at 20° C. the reaction mixture was filtered affording 1.34 g of the title compound.

mp 238–241° C.

$^1$H-NMR (DMSO-$d_6$) δ2.30(s, 3H); 4.60–4.70(m, 1H); 5.25–5.35(m, 1H); 7.20–7.85(m, 12H).

HPLC: $R_t$=23.7 min (Method a)

Calculated for $C_{30}H_{33}N_5O_5$,HCl:

C, 64.74; H, 6.25; N, 12.78%; found:

C, 65,91; H, 6.39; N, 12.42%.

Example 5

5-{(1R)-1-[(2R)-2-(3-Aminomethylbenzoylamino)-3-(2-naphthyl)propionylamino]-2-phenylethyl}-[1,2,4]oxadiazole-3-carboxylic acid ethyl ester, triflouroacetic acid

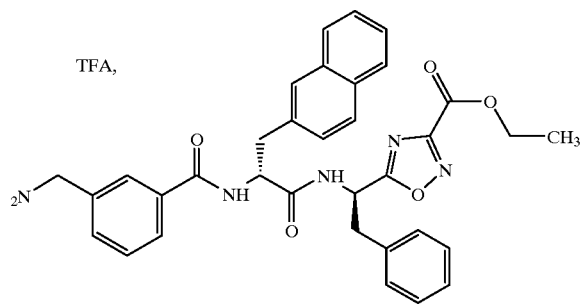

Prepared according to method E.

(R) 5-(1-tert-Butoxycarbonylamino-2-phenylethyl)-[1,2,4]oxadiazole-3-carboxylic acid ethyl ester

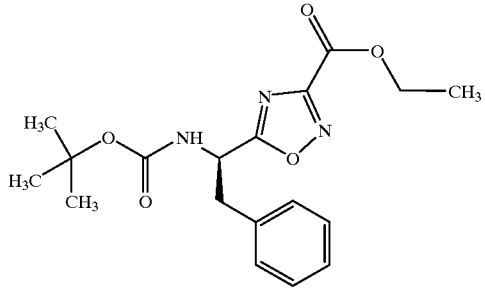

1,3-Dicyclohexylcarbodiimide (2.1 g, 10 mmol) was dissolved in dichloromethane (25 ml) and added to a solution of (R) N-tert-butoxycarbonylphenylalanine (2.2 g, 10 mmol) in dichloromethane (50 ml) at 0–5° C. The reaction mixture was heated to 20° C. and stirred at this temperature for 30 min. Ethyl 2-amino-2-(hydroxyimino)acetate (1.3 g, 10 mmol) was dissolved in pyridine (50 ml) and added to the reaction mixture. The dichloromethane was evaporated and the reaction mixture was heated at reflux temperature for 18 h. The reaction mixture was cooled to 0° C. and filtered. The filtrate was diluted with ethyl acetate (25 ml) and washed with aqueous citric acid (10%, 3×15 ml) and water (3×15 ml). After drying (magnesium sulfate) the solution was concentrated in vacuo and purified by flash chromatography on silica gel (90 g) using ethyl acetate and heptane (1:1) to give 1.68 g of (R) 5-(1-tert-butoxycarbonylamino-2-phenylethyl)-[1,2,4]oxadiazole-3-carboxylic acid ethyl ester.

mp 72–76° C.

$^1$H-NMR (DMSO-$d_6$) δ1.30(s, 9H); 1.32(t, 3H); 3.10–3.30(m, 2H); 4.41(q, 2H); 5.10(q, 1H); 7.20–7.50(m, 5H).

(R) 5-(1-Amino-2-phenylethyl)-[1,2,4]oxadiazole-3-carboxylic acid ethyl ester hydrochloride

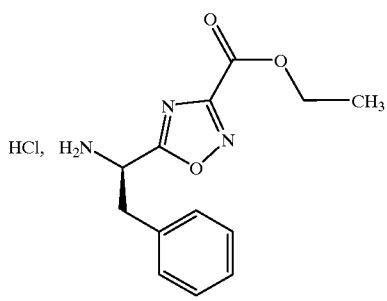

(R) 5-(1-tert-Butoxycarbonylamino-2-phenylethyl)-[1,2,4]oxadiazole-3-carboxylic acid ethyl ester (1.5 g, 4.2 mmol) was dissolved in a saturated solution of hydrogen chloride in ethyl acetate (40 ml). After 5 h at 20° C. the reaction mixture was concentrated in vacuo to give 1.2 g of (R) 5-(1-amino-2-phenylethyl)-[1,2,4]oxadiazole-3-carboxylic acid ethyl ester hydrochloride.

$^1$H-NMR (DMSO-$d_6$) δ1.32(t, 3H); 4.41(q, 2H), 5.20(dd, 1H); 7.10–7.30(m, 5H).

5-[(1R)-1-{(2R)-2-tert-Butoxycarbonylamino-3-(2-naphthyl)propionylamino}-2-phenylethyl]-[1,2,4]oxadiazole-3-carboxylic acid ethyl ester

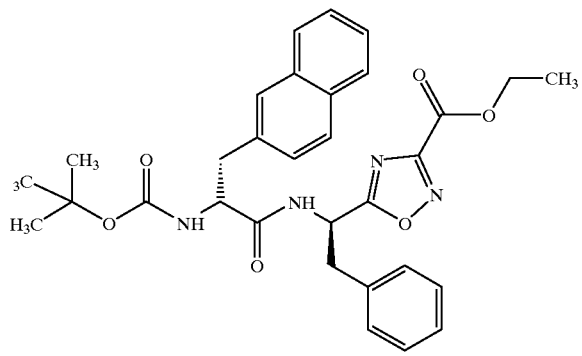

N-(3-Dimethylaminopropyl)-N'-ethylcarbodiimide hydrochloride (0.77 g, 4.03 mmol) and 1-hydroxybenzotriazole monohydrate (0.62 g, 32.9 mmol) were added to a solution of (R) N-tert-butoxycarbonyl-3-(2-naphthyl)alanine (1.27 g, 4.03 mmol) in N,N-dimethylformamide (20 ml). After 30min at 20° C. a solution of (R) ethyl 5-(1-amino-2-phenylethyl)-[1,2,4]oxadiazole-3-carboxylate hydrochloride (1.20 g, 4.03 mmol) in N,N-dimethylformamide (15 ml) was added. The reaction mixture was heated to 50° C. for 3 h, poured on water (400 ml) and extracted several times with dichloromethane (total 350 ml). The combined organic phases were washed with a saturated solution of sodium hydrogencarbonate (2×50 ml)and dried (magnesium sulfate). The solution was concentrated in vacuo and purified by flash chromatography on silica gel (40 g) using ethyl acetate and heptane (3:7) to give 0.41 g of 5-[(1R)-1-{(2R)-2-tert-butoxycarbonylamino-3-(2-naphthyl)propionylamino}-2-phenylethyl]-[1,2,4]oxadiazole-3-carboxylic acid ethyl ester.

$^1$H-NMR (DMSO-d$_6$) δ1.23(s, 9H); 1.32(t, 3H); 4.25–4.35(m, 1H), 4.38–4.45(q, 2H); 5.38–5.48(m, 1H); 7.20–7.85(m, 12H).

5-[(1R)-1-{(2R)-2-Amino-3-(2-naphthyl)propionyl}amino-2-phenylethyl]-[1,2,4]oxadiazole-3-carboxylic acid ethyl ester hydrochloride

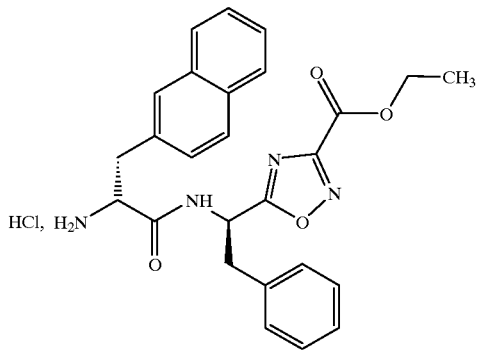

5-[(1R)-1-{(2R)-2-tert-Butoxycarbonylamino-3-(2-naphthyl)propionylamino}-2-phenylethyl]-[1,2,4]oxadiazole-3-carboxylic acid ethyl ester (0.41 g, 0.7 mmol) was suspended in a saturated mixture of hydrogen chloride in ethyl acetate (10 ml). After 18 h at 20° C., the reaction mixture was filtered to give 0.39 g of 5-[(1R)-1-{(2R)-2-amino-3-(2-naphthyl)propionylamino}-2-phenylethyl]-[1,2,4]oxadiazole-3-carboxylic acid ethyl ester hydrochloride.

$^1$H-NMR (DMSO-d$_6$) δ1.32(t, 3H); 4.10–4.20((m, 1H); 4.40–4.45(m, 2H); 5.40–5.50(m, 1H).

5-[(1R)-1-{(2R)-2-((3-tert-Butoxycarbonylaminomethyl)benzoylamino)-3-(2-naphthyl)propionylamino}-2-phenylethyl]-[1,2,4]oxadiazole-3-carboxylic acid ethyl ester

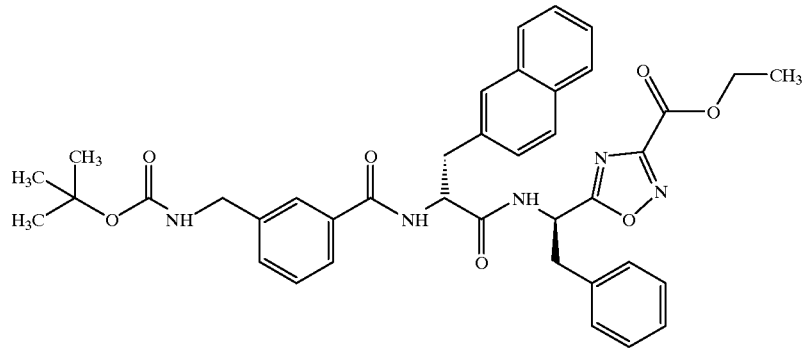

N-(3-Dimethylaminopropyl)-N'-ethylcarbodiimide hydrochloride (0.23 g, 1.20 mmol) and 1-hydroxybenzotriazole monohydrate (0.18 g, 1.2 mmol) were added to a solution of 3-(tert-butoxycarbonylaminomethyl)benzoic acid (0.30 g, 1.2 mmol) in N,N-dimethylformamide (8 ml). After 1 h at 20° C. a mixture of 5-[(1R)-1-{(2R)-2-amino-3-(2-naphthyl) propionylamino}-2-phenylethyl]-[1,2,4]oxadiazole-3-carboxylic acid ethyl ester hydrochloride (0.39 g, 0.79 mmol) and triethylamine (0.08 g, 0.79 mmol) in N,N-dimethylformamide (2 ml) were added. After 18 h at 20° C. the reaction mixture was poured on water (70 ml) and extracted several times with ethyl acetate (total 80 ml). The organic phases were collected and washed with aqueous citric acid (10%, 15 ml), a saturated solution of sodium hydrogencarbonate (10 ml) and water (3×10 ml). After drying (magnesium sulfate) the solution was concentrated in vacuo and crystallized from a mixture of ethyl acetate and heptane to give 0.44 g of 5-[(1R)-1-{(2R)-2-((3-tert-butoxycarbonylaminomethyl)benzoylamino)-3-(2-naphthyl)propionylamino}-2-phenylethyl]-[1,2,4] oxadiazole-3-carboxylic acid ethyl ester.

mp=170–176° C.

$^1$H-NMR (DMSO-d$_6$) δ1.30–1.40 (m, 12H); 4.42(q, 2H), 4.80–4.90(m, 1H); 5.40–5.50(m, 1H).

5-[(1R)-1-{(2R)-2-((3-tert-Butoxycarbonylaminomethyl) benzoylamino)-3-(2-naphthyl)propionylamino}-2phenylethyl]-[1,2,4]oxadiazole-3-carboxylic acid ethyl ester (o.40 g, 0.58 mmol) was suspended in a saturated solution of hydrogen chloride in ethyl acetate (10 ml). After 5 h at 20° C. the reaction mixture was concentrated in vacuo. The compound was purified by flash chromatography with silica gel (40 g) using a mixture of dichloromethane and 10% ammonia in ethanol (9:1) as eluent to give 0.14 g of the title compound. The compound was further purified by semipreparative HPLC in three runs on a 25 mm×250 mm column packed with 7μ C-18 silica which was preequilibrated with 30% acetonitrile in a 0.5M solution of ammonium sulfate, which was adjusted to pH 2.5 with sulfuric acid (4M). The column was eluted with a gradient of 24% to 50% acetonitrile in 0.5M ammonium sufate, pH 2.5 at 10 ml/min during 47 min at 40° C. and the fractions corresponding to the major peak were collected, diluted with three volumes of water and applied to a Sep-Pak C-18 cartrigde (Waters part # WAT036915). After preequilibration with 0.1% TFA, the compound was eluted from the Sep-Pak cartridge with 70% TFA and isolated from the eluate by lyophilisation.

$^1$H-NMR (DMSO-d$_6$) δ1.35(t, 3H); 4.40(q, 2H); 4.85–4.95(m, 1H); 5.35–5.45(m, 1H); 7.10–7.85(m, 16H).

HPLC: R$_t$=28.4 min (method: 0–90% 0.1% TFA in acetonitrile over 50 min)

Calculated for C$_{34}$H$_{33}$N$_5$O$_5$,TFA,1.5H$_2$O:

C, 59.01; H, 5.09; N, 9.56%; found:

C, 68,89; H, 5.10; N, 9.74%.

Example 6

5-{1-[2-(3-Aminomethylbenzoyl)-3-(2-naphthyl) propionyl-N-methylamino]-2-(2-naphthyl)ethyl}-[1, 2,4]oxadiazol-3-carboxylic acid ethyl ester

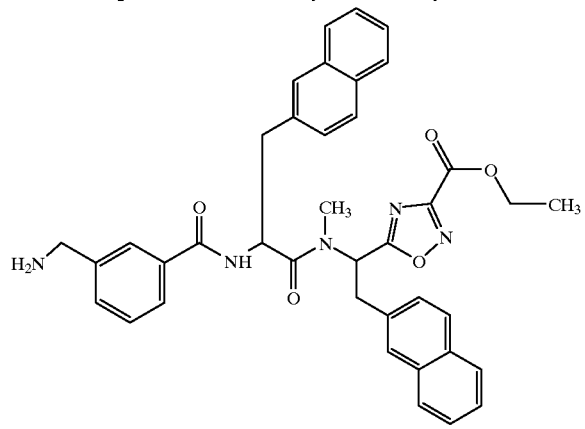

Prepared according to method E.

(R)-3-(2-Naphthyl)alanine methyl ester

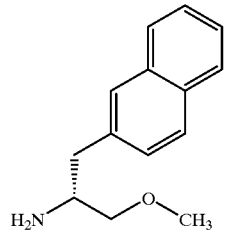

Thionyl chloride (5 ml) was added dropwise over 15 min. to a suspension of (R)-3-(2-naphthyl)alanine (5.0 g) in methanol (50 ml) at 35° C. After addition the mixture was heated at 60° C. for 1 h, cooled and the solvent removed in vacuo. Water (75 ml) and ethyl acetate (125 ml) were added and pH was adjusted to 8.5 with sodium carbonate. The organic phase was separated and dried (magnesium sulfate) to afford 4.86 g of (R)-3-(2-naphthyl)alanine methyl ester.

$^1$H-NMR (CDCl$_3$) d 1.50 (s(br), 2H); 3.03 (dd, 1H); 3.27 (dd, 1H); 3.71 (s, 3H); 3.84 (dd, 1H); 7.30–7.82 (m, 7H).

(R)-2-(3-(tert-Butoxycarbonylaminomethyl) benzoylamino)-3-(2-naphthyl)-propionic acid methyl ester

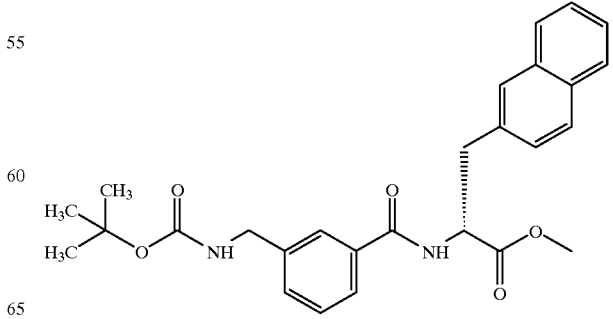

3-(tert-Butoxycarbonylaminomethyl)benzoic acid (5.32 g; 21.2 mmol) was dissolved in N,N-dimethylformamide (20 ml). 1-Ethyl-3-(3-dimethylaminopropyl)-carbodiimide hydrochloride (4.06 g, 21.2 mmol) was added and the mixture was stirred for 20 min. A solution of (R)-3-(2-naphthyl)alanine methyl ester (4.85 g, 21.2 mmol) in N,N-dimethylformamide (20 ml) and triethylamine (4.4 ml) was added and stirring was continued for 18 h. The mixture was diluted with ethyl acetate (400 ml) and the organic phase was washed with water (200 ml), 10% aqueous sodium hydrogensulfate (50 ml), 5% aqueous sodium hydrogencarbonate (100 ml) and water (100 ml). The phases were separated and the organic phase was dried (magnesium sulfate) and the solvent removed in vacuo to afford 8.9 g of (R)-2-(3-(tert-butoxycarbonylaminomethyl)benzoylamino)-3-(2-naphthyl)propionic acid methyl ester.

$^1$H-NMR (CDCl$_3$) δ1.44 (s, 9H); 3.40 (t, 2H); 3.76 (s, 3H) 4.28 (d, 2H); 5.00 (s(br), 1H); 5.18 (q, 1H); 6.75 (d, 1H); 7.20–7.80 (m, 11H)

(R)-2-(3-(tert-Butoxycarbonylaminomethyl) benzoylamino)-3-(2-naphthyl)propionic acid

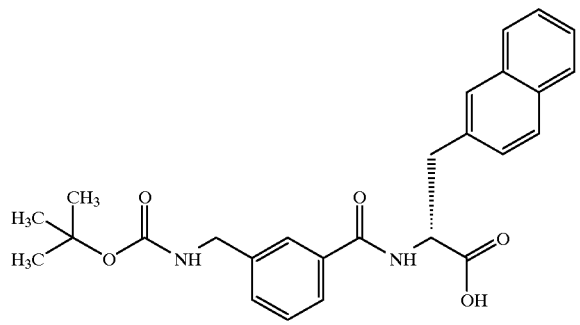

(R)-2-(3-(tert-Butoxycarbonylaminomethyl) benzoylamino)-3-(2-naphthyl)propionic acid methyl ester (8.8 g, 19.1 mmol) was dissolved in methanol (100 ml) and lithium hydroxide (0.55 g, 22.2 mmol) was added. After 2 h dichloromethane (200 ml), water (200 ml) and 3 M sodium hydrogen sulfate (50 ml) were added. The organic phase was separated and washed with water (100 ml). The organic phase was dried (magnesium sulfate) and the solvent removed in vacuo to yield 7.9 g of (R)-2-(3-(tert-butoxycarbonylaminomethyl)benzoylamino)-3-(2-naphthyl)propionic acid.

$^1$H-NMR (DMSO) δ1.38, 1.39 (two s, 9H); 3.30 (m, 2H); 4.12 (d, 2H); 4.71 (m, 1H); 6.10 (s(br), 1H); 7.30–7.90 (m, 11 H); 8.75 (d, 1H); 12.80 (s(br), 1H).

(R)-5-(1-(N-Methyl-tert-butoxycarbonylamino)-2-(2-naphthyl)ethyl)-[1,2,4]oxadiazole-3-carboxylic acid ethyl ester

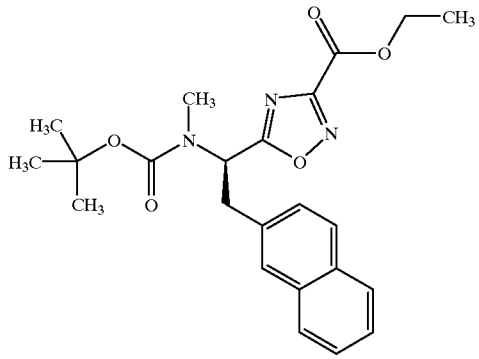

1,3-Dicyclohexylcarbodiimide (1.88 g, 9.1 mmol) was dissolved in dichloromethane (25 ml) and added to a solution of (R) N-tert-butoxycarbonyl-(2-naphthyl)alanine (3.0 g, 9.1 mmol) in dichloromethane (50 ml) at 0–5° C. The reaction mixture was heated to 20° C. and stirred at this temperature for 30 min. Ethyl 2-amino-2-(hydroxyimino) acetate (1.2 g, 9.1 mmol) was dissolved in pyridine (50 ml) and added to the reaction mixture. The dichloromethane was evaporated and the reaction mixture was heated at reflux temperature for 18 h. The reaction mixture was cooled to 0° C. and filtered. The eluent was concentrated in vacuo, redissolved in ethyl acetate (25 ml) and washed with aqueous citric acid (10%, 3×15 ml) and water (3×15 ml). After drying (magnesium sulfate) the solution was concentrated in vacuo and purified by flash chromatography on silica gel (90 g) using ethyl acetate and heptane (1:4) to give 1.59 g of (R) 5-(1-(N-methyl-tert-butoxycarbonylamino)-2-(2-naphthyl) ethyl)-[1,2,4]oxadiazole-3-carboxylic acid ethyl ester.

mp 99–102° C.

$^1$H-NMR (DMSO-d$_6$) δ1.30–1.40(m, 3H); 4.40–4.50(m, 2H); 5.70–5.90(m, 1H); 7.45–7.90(m, 7H).

(R) 5-(1-Methylamino-2-(2-naphthyl)ethyl)-[1,2,4]oxadiazole-3-carboxylic acid ethyl ester hydrochloride

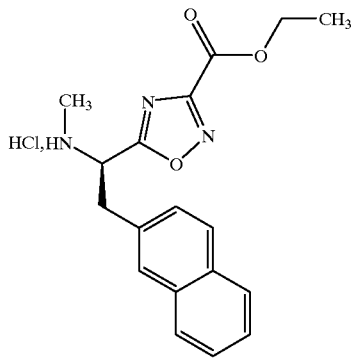

(R) 5-(1-(N-Methyl-tert-butoxycarbonylamino)-2-(2-naphthyl)ethyl)-[1,2,4]oxadiazole-3-carboxylic acid ethyl ester (0.77 g, 1.8 mmol) was dissolved in a saturated solution of hydrogen chloride in ethyl acetate (15 ml). After 5 h at 20° C. the reaction mixture was concentrated in vacuo to give 0.72 g of (R) 5-(1-methylamino-2-(2-naphthyl)ethyl)-[1,2,4]oxadiazole-3-carboxylic acid ethyl ester hydrochloride.

$^1$H-NMR (DMSO-$d_6$) δ1.32(t, 3H); 2.71(s, 3H); 4.40(q, 2H1); 5.45(q, 1H); 7.30–7.90(m, 7H).

HPLC: $R_t$=19.7 min (Method a)

5-{1-[2-(3-(tert-Butoxycarbonylaminomethyl)benzoylamino)-3-(2-naphthyl)propionyl-N-methylamino]-2-(2-naphthyl)ethyl}-[1,2,4]oxadiazole-3-carboxylic acid ethyl ester

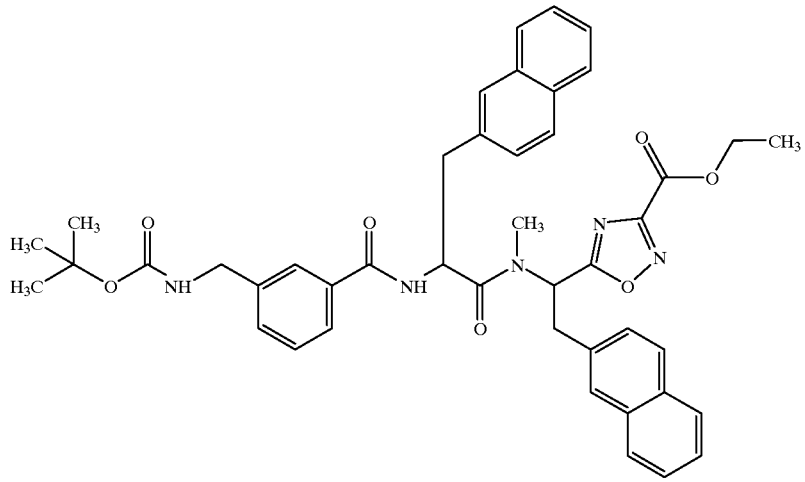

N-(3-Dimethylaminopropyl)-N'-ethylcarbodiimide hydrochloride (0.51 g, 2.6 mmol) and 1-hydroxy-7-azabenzotriazole (0.36 g, 2.6 mmol) were added to a solution of 2-(3-(tert-butoxycarbonylaminomethyl)benzoylamino)-3-(2-naphthyl)propionic acid (1.18 g, 2.6 mmol) in N,N-dimethylformamide (15 ml). After 30 min at 20° C. a mixture of (R) 5-(1-methylamino-2-(2-naphthyl)ethyl)-[1,2,4]oxadiazole-3-carboxylic acid ethyl ester hydrochloride (0.69 g, 1.9 mmol) and triethylamine (0.19 g, 1.9 mmol) in N,N-dimethylformamide (10 ml) were added. After 18 h at 20° C. the reaction mixture was poured onto water (175 ml) and extracted several times with ethyl acetate (total 175 ml). The combined organic phases were washed with aqueous citric acid (10%, 20 ml), a saturated solution of sodium hydrogencarbonate (25 ml), water (3×25 ml) and dried (magnesium sulfate). The solution was concentrated in vacuo and purified by flash chromatography on silica gel (80 g) using ethyl acetate and heptane (2:3) to give 0.8 g of a 1:1 mixture of two diastereoisomers of 5-{1-[2-(3-(tert-butoxycarbonylaminomethyl)benzoylamino)-3-(2-naphthyl)propionyl-N-methylamino]-2-(2naphthyl)ethyl}-[1,2,4]oxadiazole-3-carboxylic acid ethyl ester.

$^1$H-NMR (DMSO-$d_6$) δ1.30–1.42(m, 12H), 4.40–4.48(m, 2H); 4.90–5.20(m, 1H); 6.00–6.10(m, 1H).

HPLC:
diastereoisomer I; $R_t$=25.6 min (Method a)
diastereoisomer II; $R_t$=30.81 min (Method a)

5-{1-[2-(3-(tert-Butoxycarbonylaminomethyl)benzoylamino)-3-(2-naphthyl)propionyl-N-methylamino]-2-(2-naphthyl)ethyl}-[1,2,4]oxadiazole-3-carboxylic acid ethyl ester (0.34 g, 0.5 mmol) was suspended in a mixture of trifluoroacetic acid and dichloromethane (1:1, 20 ml). After 10 min at 20° C., the reaction mixture was concentrated in vacuo and purified by flash chromatography on silica gel (40 g) using dichloromethane and a 10% mixture of ammonia in ethanol (85:15) to give 0.14 g of two diastereoismers of the title compound.

$^1$H-NMR (DMSO-$d_6$) δ1.35–1.50(m, 3H); 4.40–4.50(m, 2H); 5.00–5.20(m, 1H); 5.98–6.13(m, 1H).

HPLC:
diasteroisomer I; $R_t$=26.9 min (Method a)
diastereoisomer II; $R_t$=37.7 min (Method a)
Calculated for $C_{39}H_{37}N_5O_5$:
C, 71.43; H, 5.69; N, 10.68%; found:
C, 71.05; H, 5.54; N, 10.41%.

Example 7

5-{(1R)-1-[(2R)-2-(piperidine-4-carbonylamino)-3-(2-naphthyl)propionyl-N-methylamino]-2-(2-naphthyl)ethyl)-[1,2,4]oxadiazole-3-carboxylic acid ethyl ester

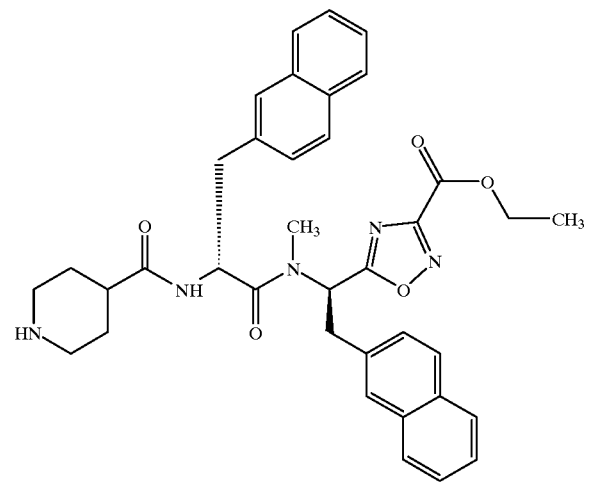

Prepared according to method E.

5-{(1R)-1-[(2R)-2-tert-Butoxycarbonylamino-3-(2-naphthyl)propionyl-N-methylamino]-2-(2-naphthyl)ethyl}-[1,2,4]oxadiazole-3-carboxylic acid ethyl ester

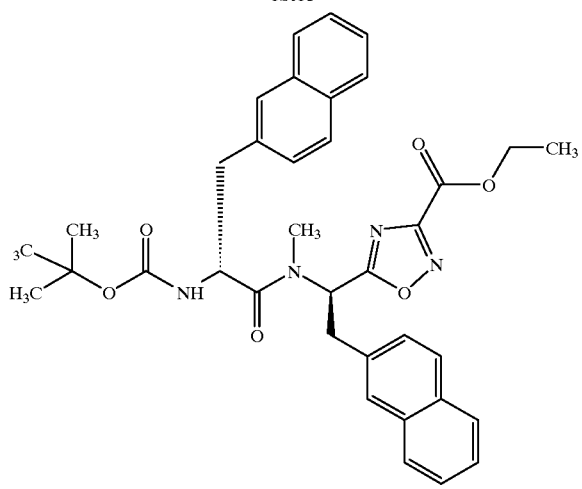

N-(3-Dimethylaminopropyl)-N'-ethylcarbodiimide hydrochloride (0.54 g, 2.8 mmol) and 1-hydroxy-7-azabenzotriazole (0.38 g, 2.8 mmol) were added to a solution of (R) N-tert-butoxycarbonyl-3-(2-naphthyl)alanine (0.88 g, 2.8 mmol) in N,N-dimethylformamide (15 ml). After 30 min at 20° C. a solution of (R) 5-(1-methylamino-2-(2-naphthyl)ethyl)-[1,2,4]oxadiazole-3-carboxylic acid ethyl ester hydrochloride (0.7 g, 2.0 mmol) in N,N-dimethylformamide (15 ml) was added. The reaction mixture was heated to 50° C. for 3 h, poured on water (180 ml) and extracted several times with ethyl acetate (total 200 ml). The combined organic phases were washed with aqueous citric acid (10%, 25 ml), a saturated solution of sodium hydrogencarbonate (30 ml), water (3×30 ml) and dried (magnesium sulfate). The solution was concentrated in vacuo to give 1.3 g of 5-{(1R)-1-[(2R)-2-tert-butoxycarbonylamino-3-(2-naphthyl)propionyl-N-methylamino]-2-(2-naphthyl)ethyl}-[1,2,4]oxadiazole-3-carboxylic acid ethyl ester.

$^1$H-NMR (DMSO-d$_6$) δ1.00–1.40(m, 12H); 4.45(q, 2H); 5.90–6.20(m, 1H).

5-{(1R)-1-[(2R)-2-Amino-3-(2-naphthyl)propionyl-N-methylamino]-2-(2-naphthyl)ethyl}-[1,2,4]oxadiazole-3-carboxylic acid ethyl ester

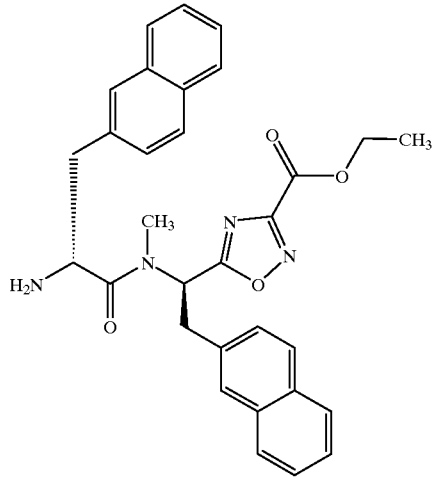

5-{(1R)-1-[(2R)-2-tert-butoxycarbonylamino-3-(2-naphthyl)propionyl-N-methylamino]-2-(2-naphthyl)ethyl}-[1,2,4]oaxdiazole-3-carboxylic acid ethyl ester (1.3 g, 2.0 mmol) was suspended in a saturated mixture of trifluoroacetic acid and dichloromethane (1:1, 50 ml). After 10 min at 20° C., the reaction mixture was concentrated in vacuo and purified by flash chromatography on silica gel (100 g) using dichloromethane and a mixture of 10% ammonia in ethanol (95:5) as eluent to give 0.9 g of 5-{(1R)-1-[(2R)-2-amino-3-(2-naphthyl)propionyl-N-methylamino]-2-(2-naphthyl)ethyl}-[1,2,4]oxadiazole-3-carboxylic acid ethyl ester.

$^1$H-NMR (DMSO-d$_6$) δ1.35(i, 3H); 4.45(q, 2H); 5.88–6.20(m, 1H).

4-((1R)-1-{[(1R)-1-(3-Ethoxycarbonyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tert-butyl ester

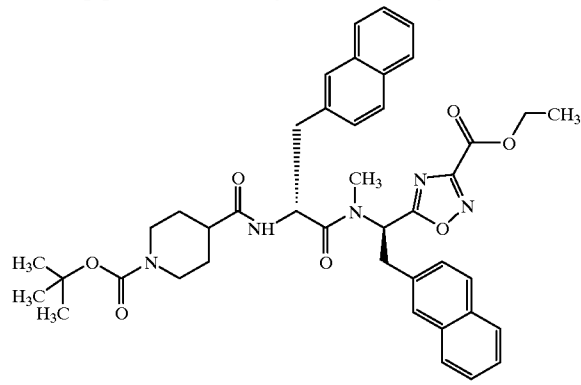

N-(3-Dimethylaminopropyl)-N'-ethylcarbodiimide hydrochloride (0.40 g, 2.1 mmol) and 1-hydroxybenzotriazole monohydrate (0.32 g, 2.mmol) were added to a solution of N-tert-butoxycarbonyl-4-piperidinecarboxylic acid (0.48 g, 2.1 mmol) in N,N-dimethylformamide (10 ml). After 1 h at 20° C. a solution of 5-{(1R)-1-[(2R)-2-amino-3-(2-naphthyl)propionyl)-N-methylamino]-2-(2-naphthyl)ethyl}-[1,2,4]oxadiazole-3-carboxylic acid ethyl ester (0.73 g, 1.4 mmol) in N,N-dimethylformamide (2 ml) was added. After 18 h at 20° C. the reaction mixture was poured on water (120 ml) and extracted several times with ethyl acetate (total 140 ml). The organic phases were combined and washed with aqueous citric acid (10%, 15 ml), a saturated solution of sodium hydrogencarbonate (15 ml) and water (3×20 ml). After drying (magnesium sulfate) the solution was concentrated in vacuo and purified by flash chromatography on silica gel (40 g) using ethyl acetate and heptane (1:1) to give 0.9 g of 4-((1R)-1-{[(1R)-1-(3-ethoxycarbonyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tert-butyl ester.

$^1$H-NMR (DMSO-d$_6$) δ1.30–1.45(m, 9H); 6.00–6.15(m, 1H).

HPLC: R$_t$=33.9 min (Method a)

4-((1R)-1-{[(1R)-1-(3-Ethoxycarbonyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tert-butyl ester (0.21 g, 0.29 mmol) was dissolved in a mixture trifluoroacetic acid and dichloromethane (1:1, 12 ml). After 10 min at 20° C. the reaction mixture was concentrated in vacuo. The compound was purified by flash chromatography with silica gel (40 g) using a mixture of dichloromethane and 10% ammonia in ethanol (4:1) as eluent to give 0.12 g of the title compound.

¹H-NMR (DMSO-d₆) δ1.30–1.40(m, 3H); 2.80–2.90(2s, 3H), 4.40–4.50(m, 2H); 5.98–6.20(m, 1H).

HPLC: R$_t$=25.0 min (Method a)

Calculated for C$_{37}$H$_{39}$N$_5$O$_5$, H$_2$O:
C, 68.19; H, 6.34; N, 10.75%; found:
C, 68,23; H, 6.25; N, 10.60%.

Example 8

Piperidine-4-carboxylic acid (1-{[1-(3-carbamoyl-[1,2,4]oxadiazol-5-yl)-2-(2-naphthyl)ethyl]-N-methylcarbamoyl}-2-(2-naphthyl)ethyl)amide

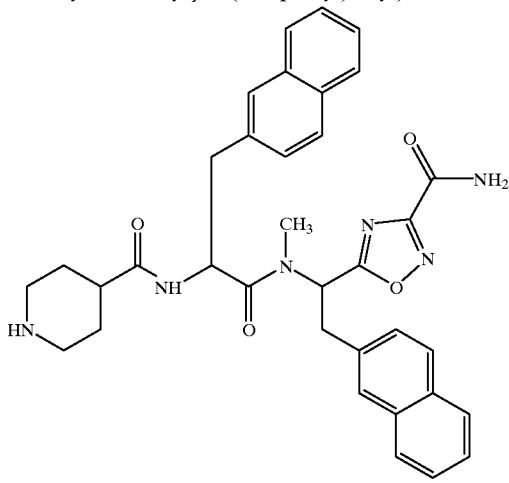

Prepared according to method E.

4-(1-{[1-(3-Carbamoyl-[1,2,4]oxadiazol-5-yl)-2-(2-naphthyl)ethyl]methylcarbamoyl}-2-(2-naphthyl)ethylcarbamoyl)piperidine-1-carboxylic acid tert butyl ester

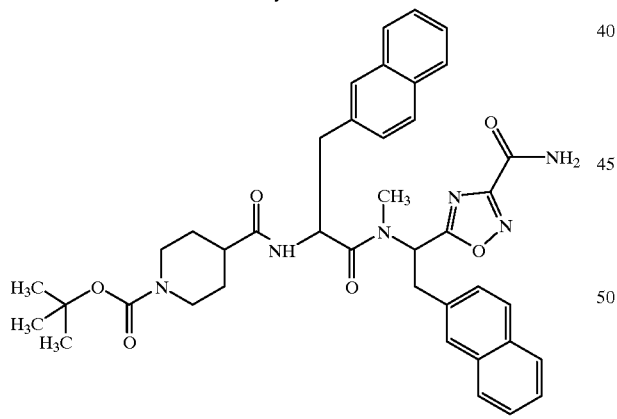

4-((1R)-1-{[[(1R)-1-(3-Ethoxycarbonyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tert-butyl ester (0.67 g, 0.91 mmol) was suspended in refluxing liquid ammonia at 1 atm. After 18 h the reaction mixture was concentrated in vacuo to give 0.58 g of two diastereoisomers of 4-(1-{[1-(3-carbamoyl-[1,2,4]oxadiazol-5-yl)-2-(2-naphthyl)-ethyl]methylcarbamoyl}-2-(2-naphthyl)ethylcarbamoyl)piperidine-1-carboxylic acid tert butyl ester.

¹H-NMR (DMSO-d₆) δ1.30–1.40(m, 9H); 4.80–4.95(m, 1H); 6.00–6.13(m, 1H).

HPLC:

diastereoisomer I: R$_t$=28.9 min (Method a)

diastereoisomer II: R$_t$=29.4 min (Method a)

The diastereomer mixture of 4-(1-{1-(3-carbamoyl-[1,2,4]oxadiazol-5-yl)-2-(2-naphthyl)ethyl)methylcarbamoyl}-2-(2naphthyl)ethylcarbamoyl)-piperidine-1-carboxylic acid tert butyl ester (0.58 g, 0.29 mmol) was dissolved in a mixture trifluoroacetic acid and dichloromethane (1:1, 12 ml). After 5 min at 20° C. the reaction mixture was concentrated in vacuo. The compound was purified by flash chromatography with silica gel (80 g) using a mixture of dichloromethane and 10% ammonia in ethanol (7:3) as eluent to give 0.44 g of two diastereoisomers of the title compound.

¹H-NMR (DMSO-d₆) δ2.88–2.92(2s, 3H); 4.79–5.00(m, 1H); 6.00–6.13(m, 1H).

HPLC:

diastereoisomer I: R$_t$=21.2 min (Method a)

diastereoisomer II: R$_t$=22.1 min (Method a)

Example 9

3-Aminomethyl-N-((1R,2E)-4-(hydroxymethyl)-1-((2-naphthyl)-methyl-5-phenylpent-2-enyl)benzamide

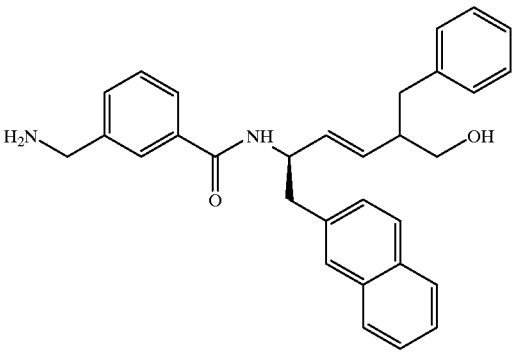

Prepared according to method A.

((1R,2E)-4-(tert-Butyldimethylsilanyloxymethyl)-1-(2-naphthyl)methyl-5-phenylpent-2-enyl)carbamic acid tert-butyl ester

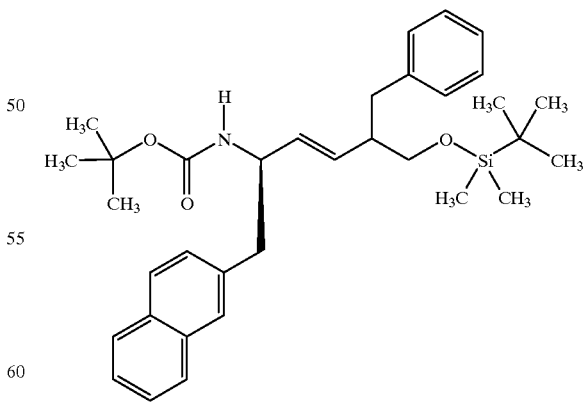

A solution of diisopropylaluminium methoxide was prepared by placing diisobutylaluminium hydride (17.9 ml of a 25% solution in toluene; 26.6 mmol) under nitrogen, cooling in an icebath and slowly treating with dry methanol (1.1 ml, 26.6 mmol). ((1R)-1-Benzenesulfonylmethyl-2-(2-naphthyl)ethyl)carbamic acid tert-butyl ester (2.14 g; 5.0 mmol) (prepared by the method of Spaltenstein et al., J. Org. Chem., 52, 3759–66, 1987) was refluxed in dry tetrahydrofuran (250 ml). The reaction mixture was cooled to −70 °C. n-Butyllithium (3.92 ml; 2.5M solution in hexane, 9.8 mmol) was added over 10 min and the solution was left with stirring for 30 min. A solution of racemic 2-(tert-butyldimethylsilanyloxymethyl)-3-phenylpropionaldehyde (2.1 g; 7.6 mmol) (prepared as in Jenmalm et al. J. Org. Chem., 59, 1139–48, 1994) in dry tetrahydrofuran (10 ml) under nitrogen was cooled to −70° C. and treated with the previously prepared solution of diisopropylaluminium methoxide (5.4 ml; 7.6 mmol). Immediately after the addition, the aluminium complex was added via cannula to the sulfone-anion solution.

Cooling was maintained for 30 min. Then aqueous ammonium chloride (40 ml; 10%), water (200 ml) and dichloromethane (200 ml) were added. The phases were separated, the organic phase was dried (magnesium sulfate) and the solvent removed in vacuo to give 5.50 g of an oil. On suspension of this oil in methanol (150 ml) a solid precipitated, was filtered off and discarded. Disodium hydrogenphosphate (1.7 g) was added to the methanol solution, cooled to 5° C. and treated with sodium amalgam (150 g; 2%). After 4 h at 20° C. the solvent was removed in vacuo and the residue was chromatographed on silica (80 g) using diethylether/heptane (1:6) as eluent. This afforded 0.85 g of a mixture of isomers of ((1R,2E)-4-(tert-butyldimethylsilanyloxymethyl)-1-(2-naphthyl)methyl-5-phenylpent-2-enyl)carbamic acid tert-butyl ester which was used in the next step without further purification.

$^1$H-NMR (CDCl$_3$) δ −0.02–0.08 (four s, 6H); 0.85–0.90 (four s, 9H); 1.40–1.45 (four s, 9H); 2.40–3.60 (m, 7H); 4.45 (s(br), 2H) 5.20–5.46 (m, 2H); 7.02–7.82 (m, 12H).

R$_f$: 0.2 diethylether/heptane (1:6)

((1R, 2E)-4-Hydroxymethyl-1-(2-naphthyl)methyl-5-phenylpent-2-enyl)carbamic acid tert butyl ester

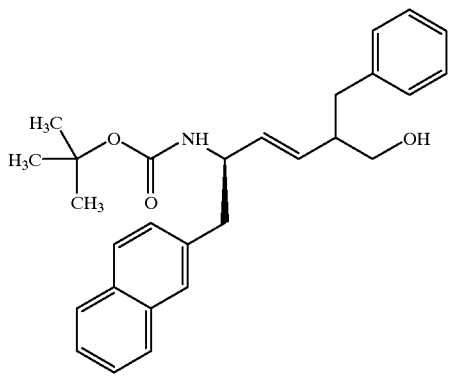

((1R,2E)-4-(tert-Butyldimethylsilanyloxymethyl)-1-(2-naphthyl)methyl-5-phenylpent-2-enyl)carbamic acid tert-butyl ester (0.75 g, 1.38 mmol) was dissolved in 2% hydrogen fluoride in acetonitrile (50 ml) and stirred at room temperature for 3 h. The solvent was removed in vacuo and the residue was chromatographed on silica (80 g) using dichloromethane/heptane/methanol (4/10/1) as eluent. Three fractions were isolated containing compounds with R$_f$ 0.1–0.2. The major fraction (eluting second) was concentrated in vacuo to give 0.35 g of ((1R,2E)-4-hydroxymethyl-1-(2-naphthyl)methyl-5-phenylpent-2-enyl) carbamic acid tert butyl ester as a mixture of diastereomers.

$^1$H-NMR (CDCl$_3$) d 1.38,1.40 (two s, 9H); 2.46–3.55 (m, 7H); 4.35 (m, 1H); 4.55 (s(br), 1H); 5.28–5.43 (m, 2H); 7.01–7.82 (m, 12H).

(3E,5R)-5-Amino-2-benzyl-6-(2-naphthyl)hex-3-en-1-ol

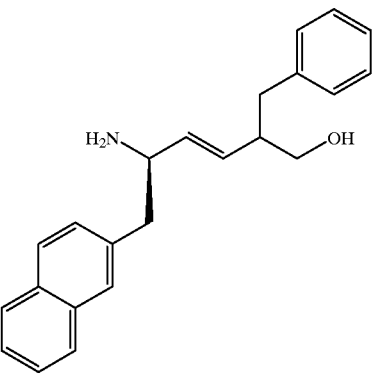

((1R,2E)4-Hydroxymethyl-1-(2-naphthyl)methyl-5-phenylpent-2-enyl)carbamic acid tert butyl ester (350 mg, 0.81 mmol) was dissolved in dichloromethane and trifluoroacetic acid (5 ml) was added. After 90 min the solvent was removed in vacuo and the residue was dissolved in dichloromethane (5 ml) and reevaporated. Finally the mixture was lyophilized in water acidified with 4 M HCl (2 ml) to afford 0.3 g of two diastereoisomers of (3E,5R)-5-amino-2-benzyl-6-(2-naphthyl)hex-3-en-1-ol as a hydrochloride which were taken to the next step without further purification.

$^1$H-NMR (CDCl$_3$) d 1.8 (s(br), 2H); 2.45–3.70 (m, 7H); 4.35 (m, 1H); 5.32–5.60 (m, 2H); 7.03–7.72 (m,12 H).

3-(tert-Butoxycarbonylaminomethyl)benzoic acid (407 mg) was dissolved in dichloromethane (6 ml) and then converted to the symmetrical anhydride by stirring with N-ethyl-N'-(3-dimethylaminopropyl)-carbodiimide hydrochloride (155 mg) for 10 min. A solution of (3E,5R)-5-amino-2-benzyl-6-(2-naphthyl)hex-3-en-1-ol hydrochloride (149 mg) and N,N-diisopropylethylamine (70 μl) in dichloromethane (3 ml) was added to the mixture and then reacted for 20 h at 20° C. The reaction mixture was then concentrated to an oil and redissolved in ethyl acetate (50 ml). The solution was extracted successively with 5% aqueous sodium hydrogen carbonate (100 ml) and with water (2×100 ml). The combined organic phases were dried (sodium sulfate) and concentrated in vacuo to an oil. The oil was dissolved in dichloromethane/trifluoroacetic acid 1:1 (6 ml) and stirred. After 10 min the mixture was concentrated by a stream of nitrogen and the resulting oil was redissolved in acetic acid (1 ml). Then water (40 ml) and acetonitrile (12 ml) were added. The solution of crude product of the title compound was then purified by semipreparative HPLC in five runs on a 25 mm×250 mm column packed with 7μ C-18 silica. The column was preequilibrated with 30% acetonitrile in 0.05M ammonium sulfate, and was adjusted to pH 2.5 with 4M sulfuric acid. The column was eluted with a gradient of 30%–45% acetonitrile in 0.05M ammonium sulfate, pH 2.5 (using 4M sulfuric acid) at 10 ml/min during 47 min at 40° C. and the fractions corresponding to the two major components were each collected, diluted with 3 volumes of water and applied to two Sep-Pak® C18 cartridges connected in series (Waters part. #:51910 ) which were preequilibrated with 0.1% trifluoroacetic acid. The compounds were eluted from the Sep-Pak® cartridges with 70% acetonitrile 0.1% trifluoroacetic acid and isolated from the eluate by lyophilisation after dilution with water. The final products obtained were characterised by analytical RP-HPLC (retention time) and by plasma desorption mass spectrometry (molecular mass). The molecular masses for isomer I and isomer II were found to 464.1 and 464.5 respectively which is in agreement with the expected structure within the experimental error of the method (±0.9 amu). The RP-HPLC analysis was performed using UV detection at 214 nm and a Vydac 218TP54 4.6 mm×250 mm 5μ C-18 silica column (The Separations Group, Hesperia) which was eluted at 1 ml/min at 42° C. Two different elution conditions were used:

A1: The column was equilibrated with 5% acetonitrile in a buffer consisting of 0.1M ammonium sulphate, which was adjusted to pH 2.5 with 4M sulfuric acid and eluted by a gradient of 5% to 60% acetonitrile in the same buffer during 50 min.

B1: The column was equilibrated with 5% acetonitrile/0.1% trifluoroacetic acid/water and eluted by a gradient of 5% acetonitrile/0.1% trifluoroacetic acid/water to 60% acetonitrile/0.1% trifluoroacetic acid/water during 50 min.

The retention time using elution conditions A1 and B1 was found to be 32.97 min and 34.52 min, respectively for isomer I and 33.67 min and 33.67 min. respectively for isomer II.

Example 10

(3R) Piperidine-3-carboxylic acid ((1R, 2E)-4-hydroxymethyl-1-(2-naphthyl)methyl-5-phenylpent-2-enyl)amide

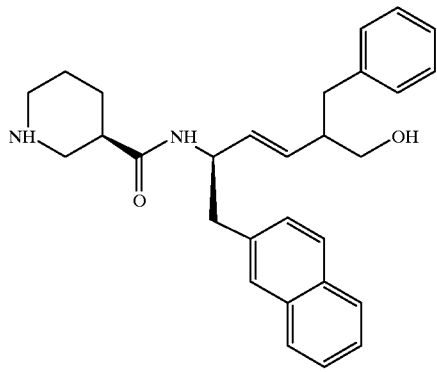

Prepared according to method A.

(3R) Piperidine-3-carboxylic acid ((1R,2E)-4-hydroxyethyl-1-(2-naphthyl) methyl-5-phenylpent-2-enyl) amide was prepared and characterized using similar procedures as in example 10. The molecular masses for isomer I and isomer II were found to 442.6 and 442.5 respectively which is in agreement with the expected structure within the experimental error of the method (±0.9 amu).

The RP-HPLC retention time using elution conditions A1 and B1 were found to be 30.02 min and 31.30 min, respectively for isomer I and 30.56 min and 31.95 min, respectively for isomer II.

Example 11

(2E)-5-Amino-5-methylhex-2-enoic acid {(1R)-1-[N-methyl-N-((1R)-1-(3-methyl-[1,2,4]oxadiazol-5-yl)-2-(2-naphthyl)-ethyl)carbamoyl]-2-(2-naphthyl)ethyl}amide

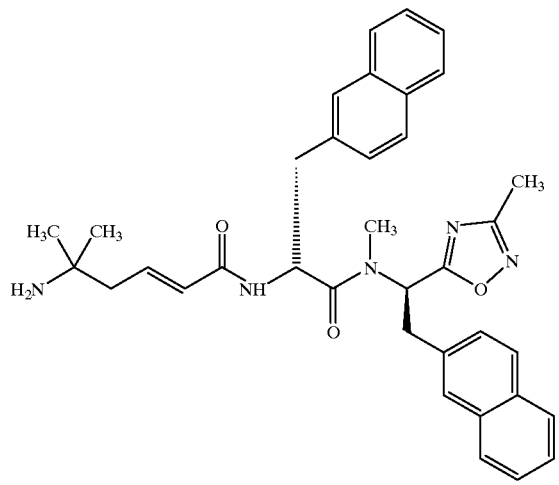

Prepared according to method E.

3-Hydroxy-1,1-dimethylpropylcarbamic acid tert-butyl ester

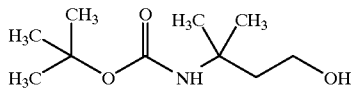

At 0° C., ethyl chloroformate (1.10 ml, 11.5 mmol) was given dropwise to a solution of 3-tert-butoxycarbonylamino-3-methylbutanoic acid (2.50 g, 11.5 mmol) and triethylamine (1.92 ml, 13.8 mmol) in THF (10 ml). The solution was stirred for 40 min at 0° C. The obtained precipitate was filtered off and washed with THF (20 ml). The liquid was immediately cooled to 0° C. A 2M solution of lithium boronhydride in THF (14.4 ml, 28.8 mmol) was added dropwise. The solution was stirred at 0° C. for 2 h, and then warmed to room temp. over a period of 4 h. It was cooled to 0° C. Methanol (5 ml) was added carefully. 1N Hydrochloric acid (100 ml) was added. The solution was extracted with ethyl acetate (2×100 ml, 3×50 ml). The combined organic layers were washed with saturated solution of sodium hydrogencarbonate (100 ml) and dried over magnesium sulfate. The solvent was removed in vacuo. The crude product was chromatographed on silica (110 g) with ethyl acetate/heptane 1:2 to give 1.84 g of 3-hydroxy-1,1-dimethylpropylcarbamic acid tert-butyl ester.

400 MHz-1H-NMR (CDCl$_3$): 1.33 (s, 6 H); 1.44 (s, 9 H); 1.88 (t, 2 H); 1.94 (br, 1 H); 3.75 (q, 2 H); 4.98 (br, 1 H).

3-(tert-Butoxycarbonylamino)-3-methylbutanal

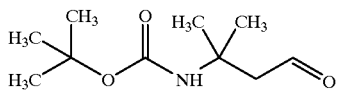

At −78° C. DMSO (1.22 ml, 17.2 mmol) was added to a solution of oxalyl chloride (1.1 ml, 12.9 mmol) in dichloromethane (15 ml). The mixture was stirred for 15 min at −78° C. A solution of 3-hydroxy-1,1-dimethylpropylcarbamic acid tert-butyl ester (1.75 g, 8.6 mmol) in dichloromethane (10 ml) was added dropwise over a period of 15 min. The solution was stirred at −78° C. for another 15 min. Triethylamine (6.0 ml, 43 mmol) was added. The solution was stirred at −78° C. for 5 min and then warmed to room temp. The solution was diluted with dichloromethane (100 ml) and extracted with 1N hydrochloric acid (100 ml). The aqueous phase was extracted with dichloromethane (50 ml). The combined organic layers were washed with a saturated solution of sodium hydrogencarbonate (100 ml) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

400 MHz-1H-NMR (CDCl$_3$): d=1.39 (s, 6 H); 1.45 (s, 9 H); 2.85 (d, 2 H); 4.73 (br. 1 H); 9.80 (t, 1 H).

Ethyl (2E)-5-(tert-Butoxycarbonylamino)-5-methylhex-2-enoate

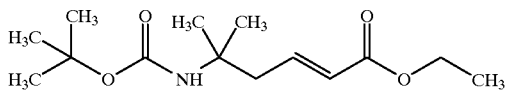

Triethylphosphonoacetate (1.96 ml, 9.8 mmol) was dissolved in THF (30 ml). Potassium tert-butoxide (1.10 g, 9.8 mmol) was added. The solution was stirred for 40 min at room temp. A solution of 3-(tert-butoxycarbonylamino)-3-methylbutanal (1.10 g, 5.5 mmol) in THF (6 ml) was added slowly. The solution was stirred at room temp. for 75 min. It was diluted with ethyl acetate (100 ml) and 1N hydrochloric acid (100 ml). The aqueous phase was extracted with ethyl acetate (2×50 ml). The combined organic layers were washed with a saturated solution of sodium hydrogencarbonate (60 ml) and dried over magnesium sulfate. The solvent was removed in vacuo. The crude product was purified by column chromatography on silica (90 g) with ethyl acetate/heptane (1:4) to give 1.27 g of ethyl (2E)-5-(tert-butoxycarbonylamino)-5-methylhex-2-enoate.

200 MHz-1H-NMR (CDCl$_3$): δ=1.30 (s, 6 H); 1.30 (t, 3 H); 1.46 (s, 9 H); 2.62 (d, 2 H); 4.27 (q, 2 H); 4.42 (br, 1 H); 5.88 (d, 1 H) 6.94 (td, 1 H).

(2E)-5-(tert-Butoxycarbonylamino)-5-methylhex-2-enoic acid

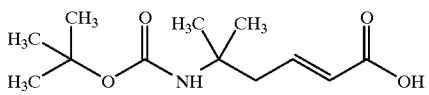

Ethyl (2E)-5-(tert-butoxycarbonylamino)-5-methylhex-2-enoate (1.233 g, 4.54 mmol) was dissolved in dioxane (20 ml). Lithium hydroxide (0.120 g, 5.00 mmol) was added as a solid. Water (10 ml) was added. The solution was stirred 16 h at room temp. The solution was diluted with water (70 ml) and was extracted with tert-butylmethylether (2×100 ml). The aqueous phase was acidified with 1N sodium hydrogensulfate solution (pH =1) and was extracted with tert-butylmethylether (3×70 ml). These organic layers were combined and dried over magnesium sulfate. The solvent was removed in vacuo to give 1.05 g of (2E)-5-(tert-butoxycarbonylamino)-5-methylhex-2-enoic acid. The crude product was used for further synthesis.

400 MHz-1H-NMR (DMSO d$_6$): δ=1.15 (s, 6 H); 1.35 (s, 9 H); 2.53 (d, 2 H); 5.75 (d, 1 H); 6.57 (br, 1 H); 6.75 (td, 1 H); 12.15 (s, 1 H)

(R) N-Methyl-N-[1-(3-methyl-[1,2,4]oxadiazol-5-yl)-2-(2-naphtyl)ethyl]carbamic acid tertbutyl ester

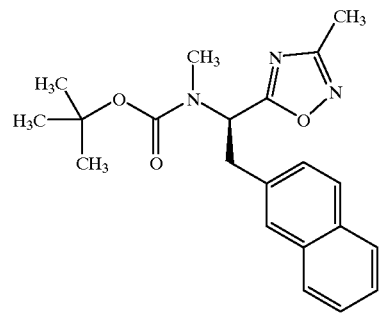

Iso-butylchloroformate (1.22 g, 9.0 mmol) was dropwise added to a solution of (R) N-methyl-N-tert-butoxycarbonyl-3-(2-naphthyl)alanine (3.0 g, 9 mmol) and N-methylmorpholine (0.91 g, 9.0 mmol) in dichloromethane (40 ml) at −20° C. After 15 min at −20° C. acetamidoxim (1.33 g, 18 mmol) was added followed by addition of N-methyl-morpholine (0.91 g, 9 mmol). After 30 min at −20° C. the reaction mixture was heated to 20° C. and diluted with N,N-dimethylformamide (40 ml). The dichloromethane was evaporated in vacuo and the reaction mixture was heated at 120° C. for 16 h. The reaction mixture was poured into water (120 ml) and extracted with ethyl acetate (total 180 ml). The organic phases were collected, washed with water (40 ml) and dried (magnesium sulfate). The solution was concentrated in vacuo to give 3.5 g of crude (R) N-methyl-N-[1-(3-methyl-[1,2,4]oxadiazol-5-yl)-2-(2-naphtyl)ethyl]carbamic acid tertbutyl ester that was used without further purification.

(R) N-Methyl-N-{1-(3-methyl-[1,2,4]oxadiazol-5-yl)-2-(2-naphthyl)ethyl}amine hydrochloride

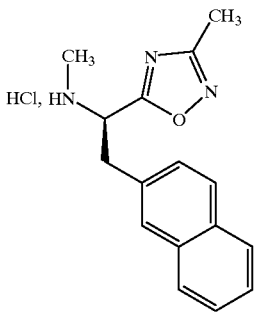

(R) N-methyl-N-[1-(3-methyl-[1,2,4]oxadiazol-5-yl)-2-(2-naphtyl)ethyl]carbamic acid tertbutyl ester (3.3 g, 9.0 mmol) was dissolved in a saturated solution of hydrogen chloride in ethyl acetate (75 ml). After 3 h at 20° C. the reaction mixture was filtered to give 1.52 g of (R) N-methyl-N-{1-(3-methyl-[1,2,4]oxadiazol-5-yl)-2-(2-naphthyl)ethyl}amine hydrochloride.

m.p. 198–202° C.

$^1$H-NMR (DMSO-$d_6$) δ2.35(s, 3H); 2.68(s, 3H); 3.43(dd, 1H); 3.80(dd, 1H); 5.29(dd, 1H); 7.30(d, 1H); 7.45–7.90(m, 7H).

HPLC: $R_t$=16.3 min (Method a)

Calculated for $C_{16}H_{17}N_3O_1$,HCl:

C, 63.26; H, 5.97; N, 13.83%; found:

C, 63,37; H, 6.11; N, 13.53%.

{(1R)-1-{N-Methyl-N-[(1R)-1-(3-methyl-[1,2,4]oxadiazol-5-yl)-2-(2-naphthyl)ethyl]carbamoyl}-2-(2-naphthyl)ethyl}carbamic acid tertbutyl ester

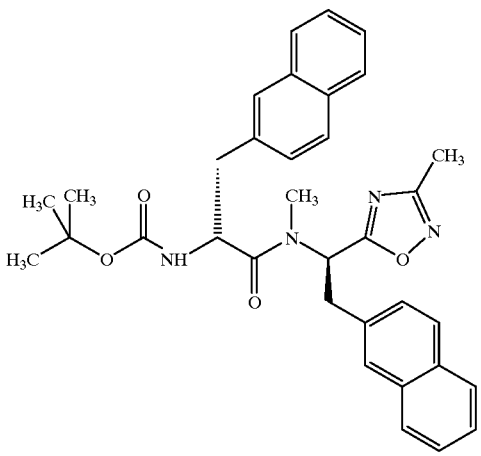

N-(3-Dimethylaminopropyl)-N'-ethylcarbodiimide hydrochloride (1.12 g, 5.85 mmol) and 1-hydroxy-7-azabenzotriazole (0.8 g, 5.85 mmol) were added to a solution of (R) N-tert-butoxycarbonyl-3-(2-naphthyl)-alanine (1.84 g, 5.85 mmol) in N,N-dimethylformamide (45 ml). After 30 min at 20° C. a mixture of (R) N-methyl-N-{1-(3-methyl-[1,2,4]oxadiazol-5-yl)-2-(2-naphthyl)ethyl}amine hydrochloride (1.27 g, 4.18 mmol) and triethylamine (0.42 g, 4.18 mmol) in N,N-dimethylformamide (15 ml) were added. After 18 h at 20° C. the reaction mixture was poured on water (200 ml) and extracted several times with ethyl acetate (total 110 ml). The combined organic phases were washed with aqueous citric acid (10%, 40 ml), a saturated solution of sodium hydrogencarbonate (3×40 ml) and water (3×40 ml). After drying (magnesium sulfate) the solution was concentrated in vacuo to give 2.4 g of crude {(1R)-1-{N-methyl-N-[(1R)-1-(3-methyl-[1,2,4]-oxadiazol-5-yl)-2-(2-naphthyl)ethyl]carbamoyl}-2-(2-naphthyl)ethyl}carbamic acid tertbutyl ester which was used for the next step without further purification.

(2R)-2-Amino-N-methyl-N-[(1R)-1-(3-methyl-[1,2,4]oxadiazol-5-yl)-2-(2-naphthyl)ethyl]-3-(2-naphthyl)propionamide, trifluoroacetic acid

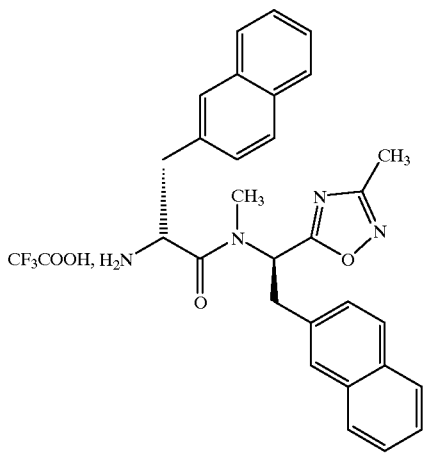

{(1R)-1-{N-Methyl-N-[(1R)-1-(3-methyl-[1,2,4]oxadiazol-5-yl)-2-(2-naphthyl)ethyl]carbamoyl}-2-(2-naphthyl)ethyl}carbamic acid tertbutyl ester (2.4 g, 4.2 mmol) was dissolved in a mixture of trifluoroacetic acid (40 ml) and dichloromethane (40 ml) at 20° C. After 10 min the reaction mixture was concentrated in vacuo and coevaporated from dichloromethane (80 ml). The residue was crystallised from ethyl acetate to give 1.19 g of (2R)-2-amino-N-methyl-N-[(1R)-1-(3-methyl-[1,2,4]oxadiazol-5-yl)-2-(2-naphthyl)-ethyl]-3-(2-naphthyl)propionamide, trifluoroacetic acid.

mp 190–191° C.

$^1$H-NMR (DMSO-$d_6$) δ2.33(s, 3H); 2.88(s, 3H); 3.00–3.15(m, 2H); 3.45(dd, 1H); 3.65(dd, 1H); 4.71(t, 1H); 7.25–7.95(m, 14H).

HPLC: $R_t$=24.3 min (Method a)

Calculated for $C_{29}H_{28}N_4O_2$,$CF_3COOH$:

C, 64.35; H, 5.05; N, 9.68%; found:

C, 64,30; H, 5.13; N, 9.44%.

63

[1,1-Dimethyl-4-((1R)-1-{N-methyl-[(1R)-1-(3-methyl-[1,2,4]oxadiazol-5-yl)-2-(2-naphthyl)ethyl]carbamoyl}-2-(2-naphthyl)ethylcarbamoyl)but-3-enyl]carbamic acid tertbutyl ester

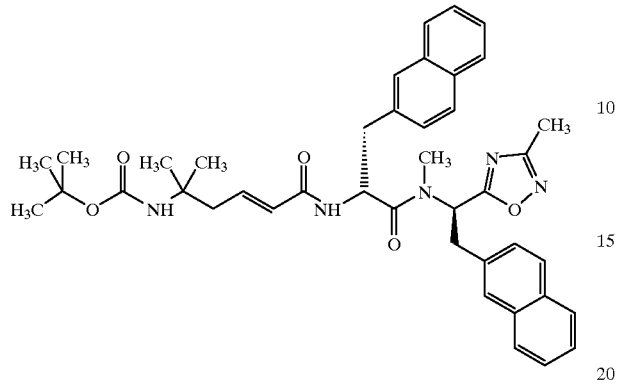

N-(3-Dimethylaminopropyl)-N'-ethylcarbodiimide hydrochloride (0.28 g, 1.48 mmol) and 1-hydroxybenzotriazole monohydrate (0.23 g, 1.48 mmol) were added to a solution of (2E)-5-(tert-butoxycarbonylamino)-5-methylhex-2-enoic acid (0.36 g, 1.48 mmol) in N,N-dimethylformamide (5 ml). After 30 min at 20° C. a mixture of (2R)-2-amino-N-methyl-N-[(1R)-1-(3-methyl-[1,2,4]oxadiazol-5-yl)-2-(2-naphthyl)-ethyl)-3-(2-naphthyl)]propionamide, trifluoroacetic acid (0.61 g, 1.06 mmol) and triethylamine (0.11 g, 1.06 mmol) in N,N-dimethylformamide (7 ml) were added. After 18 h at 20° C. the reaction mixture was poured on water (80 ml) and extracted several times with ethyl acetate (total 40 ml). The organic phases were collected and washed with aqueous citric acid (10%, 15 ml), a saturated solution of sodium hydrogencarbonate (3×15 ml) and water (3×15 ml). After drying (magnesium sulfate) the solution was concentrated in vacuo to give 0.71 g of crude [1,1-dimethyl-4-((1R)-1-{N-methyl-[(1R)-1-(3-methyl-[1,2,4]oxadiazol-5-yl)-2-(2-naphthyl)ethyl]carbamoyl}-2-(2-naphthyl)ethylcarbamoyl)but-3-enyl]carbamic acid tertbutyl ester which was used for the next step without further purification.

HPLC: $R_t$=34.9 min (Method a)

[1,1-Dimethyl-4-((1R)-1-{N-methyl-[(1R)-1-(3-methyl-[1,2,4]oxadiazol-5-yl)-2-(2-naphthyl)ethyl]carbamoyl}-2-(2-naphthyl)ethylcarbamoyl)but-3-enyl]carbamic acid tertbutyl ester (0.71 g, 1.03 mmol) was dissolved in a mixture trifluoroacetic acid (10 ml) and dichloromethane (10 ml). After 10 min at 20° C. the reaction mixture was concentrated in vacuo. The compound was chromatographed on silica (80 g) using a 10% mixture of ammonia in ethanol and dichloromethane (9:91) as eluent to give 0.44 g of the title compound.

HPLC: $R_t$=23.6 min (Method a)

Calculated for $C_{36}H_{39}N_5O_3$, 0.75$H_2O$:

C, 71.68; H, 6.77; N, 11.61%; found:

C, 71.76; H, 6.73; N, 11.12%.

64

Example 12

4-Amino-4-methylpent-2-enoic acid [(1R)-1-{N-methyl-N-[(1R)-1-(3-methyl-[1,2,4]oxadiazol-5-yl)-2-(2-naphthyl)ethyl]carbamoyl}-2-(2-naphthyl)ethyl]amide

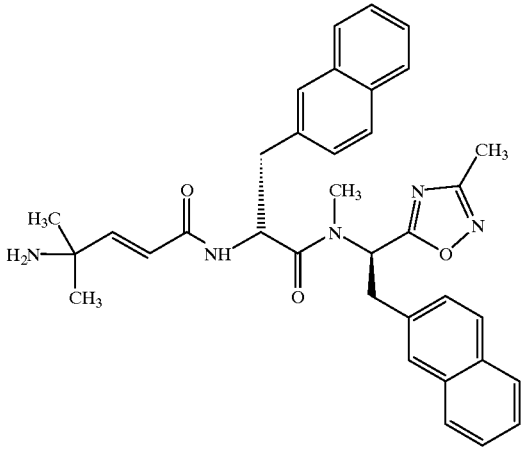

Prepared according to method E.

{1,1-Dimethyl-3-[(1R)-1-{N-methyl-N-{(1R)-1-(3-methyl-[1,2,4]oxadiazol-5-yl)-2-(2-naphthyl)ethyl}carbamoyl}-2-(2-naphthyl)ethylcarbamoyl]allyl}carbamic acid tertbutyl ester

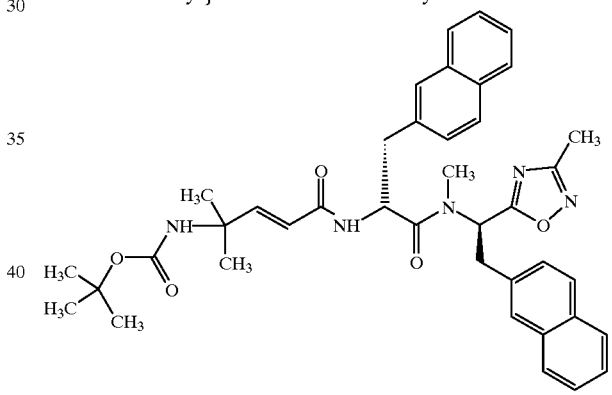

N-(3-Dimethylaminopropyl)-N'-ethylcarbodiimide hydrochloride (0.26 g, 1.38 mmol) and 1-hydroxybenzotriazole monohydrate (0.21 g, 1.38 mmol) were added to a solution of N-tertbutoxycarbonyl-4-amino-4-methylpent-2-enoic acid (0.32 g, 1.38 mmol) in N,N-dimethylformamide (5 ml). After 30 min at 20° C. a mixture of (2R)-2-amino-N-methyl-N-[(1R)-1-(3-methyl-[1,2,4]oxadiazol-5-yl)-2-(2-naphthyl)ethyl]-3-(2-naphthyl)propionamide, trifluoroacetic acid (0.57 g, 0.99 mmol) and triethylamine (0.10 g, 0.99 mmol) in N,N-dimethylformamide (6 ml) were added. After 18 h at 20° C. the reaction mixture was poured on water (75 ml) and extracted several times with ethyl acetate (total 30 ml). The organic phases were collected and washed with aqueous citric acid (10%, 15 ml), a saturated solution of sodium hydrogencarbonate (3×15 ml) and water (3×15 ml). After drying (magnesium sulfate) the solution was concentrated in vacuo to give 0.68 g of crude (1,1-dimethyl-3-[(1R)-1-{N-methyl-N-{(1R)-1-(3-methyl-[1,2,4]oxadiazol-5-yl)-2-(2-naphthyl)ethyl}carbamoyl}-2-(2-naphthyl)ethylcarbamoyl]allyl}carbamic acid tertbutyl ester which was used for the next step without further purification.

HPLC: R$_f$=33.4 min (Method a)

{1,1-Dimethyl-3-[(1R)-1-{N-methyl-N-{(1R)-1-(3-methyl-[1,2,4]oxadiazol-5-yl)-2-(2-naphthyl)ethyl}carbamoyl}-2-(2-naphthyl)ethylcarbamoyl]allyl}carbamic acid tertbutyl ester (0.68 g, 1.01 mmol) was dissolved in a mixture of trifluoroacetic acid (10 ml) and dichloromethane (10 ml). After 10 min at 20° C. the reaction mixture was concentrated in vacuo and chromatographed on silica gel (80 g) using a 10% mixture of ammonia in ethanol and dichloromethane (1:9) as eluent to give 0.48 g of the title compound.

HPLC: R$_f$=23.3 min (Method a)

Calculated for $C_{35}H_{37}N_5O_3,0.5H_2O$:

C, 71.90; H, 6.55; N, 11.98%; found:

C, 71.82; H, 6.55; N, 11.71%.

Example 13

(2E)-4-Amino-4-methylpent-2-enoic acid N-[(1R)-1-{N-methyl-N-[(1R)-1-(3-methyl-[1, 2,4]oxadiazol-5-yl)-2-(2-naphthyl)ethyl]carbamoyl}-2-(2-naphthyl)ethyl]-N-methylamide

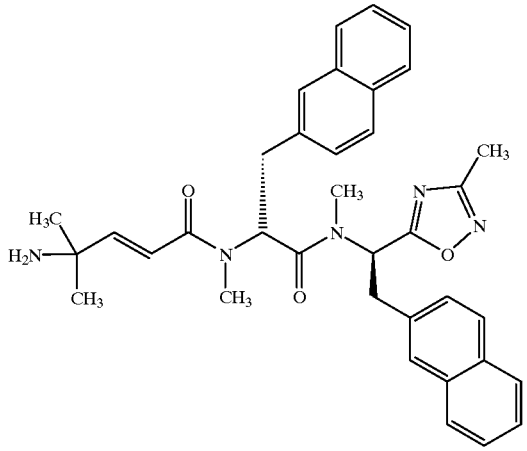

Prepared according to method E.

N-Methyl-N-((1R)-1-{N-methyl-N-[(1R)-1-(3-methyl-[(1,2,4]oxadiazol-5-yl)-2-(2-naphthyl)ethyl]carbamoyl}-2-(2-naphthyl)ethyl)carbamic acid tertbutyl ester

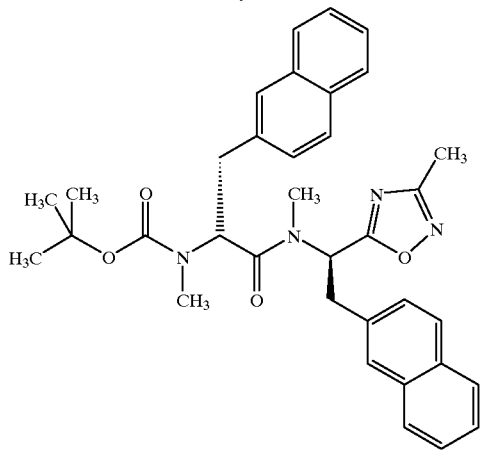

N-(3-Dimethylaminopropyl)-N'-ethylcarbodiimide hydrochloride (1.34 g, 7.0 mmol) and 1-hydroxy-7-azabenzotriazole (0.95 g, 7.0 mmol) were added to a solution of (R) N-tert-butoxycarbonyl-3-(2-naphthyl)alanine (2.31 g, 7.0 mmol) in N,N-dimethylformamide (50 ml). After 30 min at 20° C. a mixture of (R) N-methyl-N-{1-(3-methyl-[1,2,4]oxadiazol-5-yl)-2-(2-naphthyl)ethyl}amine hydrochloride (1.52 g, 5.0 mmol) and triethylamine (0.51 g, 5.0 mmol) in N,N-dimethylformamide (10 ml) was added. After 18 h at 20° C. the reaction mixture was poured on water (250 ml) and extracted several times with ethyl acetate (total 130 ml). The collected organic phases were washed with aqueous citric acid (10%, 50 ml), a saturated solution of sodium hydrogencarbonate (3×50 ml) and water (3×50 ml). After drying (magnesium sulfate) the solution was concentrated in vacuo and chromatographed on silica (110 g) using heptane and ethyl acetate (1:1) to give 2.4 g of N-methyl-N-((1R)-1-{N-methyl-N-[(1R)-1-(3-methyl-[1,2,4]oxadiazol-5-yl)-2-(2-naphthyl)ethyl]carbamoyl}-2-(2-naphthyl)ethyl)carbamic acid tertbutyl ester.

HPLC: R$_f$=36.5 min (Method a)

(2R)-2-Methylamino-N-methyl-N-[(1R)-1-(3-methyl-[1,2,4]oxadiazol-5-yl)-2-(2-naphthyl)ethyl]-3-(2-naphthyl)propionamide, trifluoroacetic acid

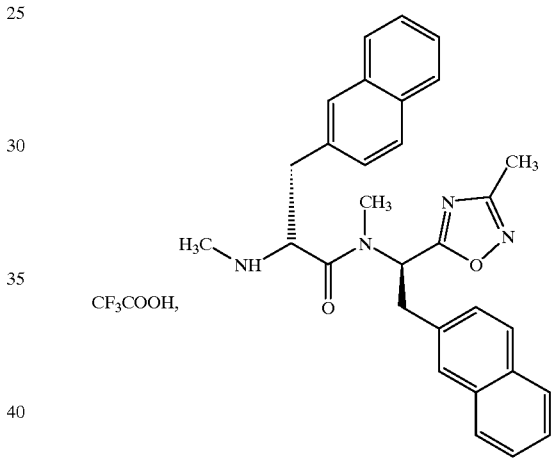

N-methyl-N-((1R)-1-{Nmethyl-N-[(1R)-1-(3-methyl[1,2,4]oxadiazol-5-yl)-2-(2-naphthyl)ethyl]carbamoyl}-2-(2-naphthyl)ethyl)carbamic acid tertbutyl ester (2.4 g, 4.2 mmol) was dissolved in a mixture of trifluoroacetic acid (40 ml) and dichloromethane (40 ml) at 20° C. After 10 min the reaction mixture was concentrated in vacuo and coevaporated from dichloromethane (80 ml). The residue was crystallised from ethyl acetate to give 1.9 g of (2R)-2-methylamino-N-methyl-N-[(1R)-1-(3-methyl-[1,2,4]oxadiazol-5-yl)-2-(2-naphthyl)ethyl]-3-(2-naphthyl)propionamide, trifluoroacetic acid.

mp 184–188° C.

$^1$H-NMR (DMSO-d$_6$) δ1.53(s, 3H); 2.34(s, 3H); 2.63(s, 3H); 3.05(dd, 1H); 3.21(dd, 1H); 3.40(dd, 1H); 3.55(dd, 1H); 4.60(t, 1H); 6.35(dd, 1H); 7.25(d, 1H); 7.40–7.90(m, 14H).

HPLC: R$_f$=24.9 min (Method a)

Calculated for $C_{30}H_{30}N_4O_2,CF_3COOH$:

C, 64.86; H, 5.27; N, 9.45%; found:

C, 65,01; H, 5.35; N, 9.32%.

67

(2E)-{1,1-Dimethyl-3-[N-((1R)-1-{N-methyl-N-{(1R)-1-(3-methyl-[1,2,4]oxadiazol-5-yl)-2-(2-naphthyl)ethyl}carbamoyl}-2-(2-naphthyl)ethyl)-N-methylcarbamoyl]allyl}carbamic acid tertbutyl ester

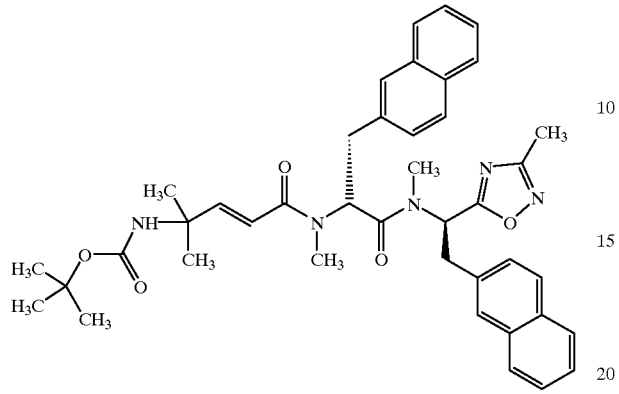

N-(3-Dimethylaminopropyl)-N'-ethylcarbodiimide hydrochloride (0.31 g, 1.6 mmol) and 1-hydroxy-7-azabenzotriazole (0.22 g, 1.6 mmol) were added to a solution of (2E)-4-tertbutoxycarbonylamino-4-methylpent-2-enoic acid (0.37 g, 1.6 mmol) in N,N-dimethylformamide (5 ml). After 30 min at 20° C. a mixture of (2R)-2-methylamino-N-methyl-N-[(1R)-1-(3-methyl-[1,2,4]oxadiazol-5-yl)-2-(2-naphthyl)-ethyl]-3-(2-naphthyl)propionamide, trifluoroacetic acid (0.68 g, 1.2 mmol) and triethylamine (0.12 g, 1.2 mmol) in N,N-dimethylformamide (5 ml) were added. After 18 h at 20° C. the reaction mixture was poured on water (80 ml) and extracted several times with ethyl acetate (total 55 ml). The organic phases were collected and washed with aqueous citric acid (10%, 15 ml), a saturated solution of sodium hydrogencarbonate (3×15 ml) and water (3×15 ml). After drying (magnesium sulfate) the solution was concentrated in vacuo and chromatographed on silica gel (80 g) using heptane and ethyl acetate (3:7) as eluent to give 0.75 g of {(2E)-1,1-dimethyl-3-[N-((1R)-1-{N-methyl-N-{(1R)-1-(3-methyl-[1,2,4]oxadiazol-5-yl)-2-(2-naphthyl)ethyl}carbamoyl}-2-(2-naphthyl)ethyl)-N-methylcarbamoyl]allyl}carbamic acid tertbutyl ester.

HPLC: $R_t$=33.8 min (Method a)

{(2E)-1,1-Dimethyl-3-[N-((1R)-1-{N-methyl-N-{(1R)-1-(3-methyl-[1,2,4]oxadiazol-5-yl)-2-(2-naphthyl)ethyl}carbamoyl}-2-(2-naphthyl)ethyl)-N-methylcarbamoyl]allyl}carbamic acid tertbutyl ester (0.62 g, 1.9 mmol) was dissolved in a mixture of trifluoroacetic acid (9 ml) and dichloromethane (9 ml). After 10 min at 20° C. the reaction mixture was concentrated in vacuo and chromatographed on silica gel (80 g) using a 10% mixture of ammonia in ethanol and dichloromethane (5:95) as eluent to give 0.44 g of the title compound.

HPLC: $R_t$=26.4 min (Method a)

Calculated for $C_{36}H_{39}N_5O_3 \cdot 0.75H_2O$:

C, 71.68; H, 6.77; N, 11.61%; found:

C, 71.81; H, 6.72; N, 11.17%.

68

Example 14

3-Aminomethyl-N-((1R)-1-{N-[(1R)-1-(((dimethylcarbamoyl)methoxy)methyl)-2-phenylethyl]-N-methylcarbamoyl}-2-(2-naphthyl)ethyl)-N-methylbenzamide

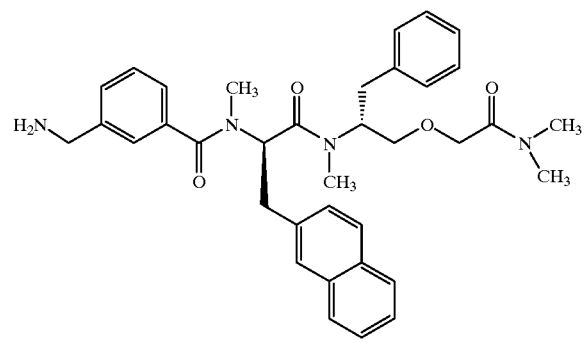

Prepared according to method G (2R)-2-(Methylamino)-3-phenylpropan-1-ol (2R)-2-(Methylamino)-3-phenylpropan-1-ol was prepared analogusly to M. J. McKennon and A. I. Meyers, K. Drauz and M. Schwarm, J. Org. Chem. 1993 (58), 3568–3571.

m.p. 69–69° C. (lit: M. J. McKennon, A. I. Meyers, K. Drauz and M. Schwarm, J. Org. Chem. 1993 (58), 3568–3571: 71–74° C.; A. Karim, A. Mortreux, F. Petit, G. Buono, G. Peiffer, C. Siv, J. Organomet. Chem. 1986, 317, 93: 68° C., for (2S)-2-(methylamino)-3-phenylpropan-1-ol).

N-((1R)-1-Hydroxymethyl-2-phenylethyl)-N-methylcarbamaic acid tert-butylester

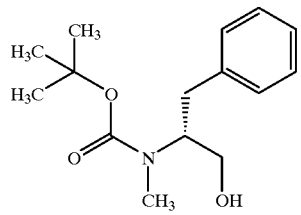

(2R)-2-(Methylamino)-3-phenylpropan-1-ol (6.00 g, 36.3 mmol) was dissolved in THF (80 ml). 1N sodium hydroxide solution (36.3 ml, 36.3 mmol) was added. A solution of di-tert-butyl dicarbonate (9.50 g, 43.6 mmol) in THF (60 ml) was slowly added at room temp. The solution was stirred 16 h at room temp. Water (200 ml) and ethyl acetate (200 ml) were added. The phases were separated. The aqueous phase was washed with ethyl acetate (2×100 ml). The combined organic layers were dried over magnesium sulfate. The solvent was removed in vacuo. The product was purified on silica (170 g) with ethyl aceate/heptane (1:1) to give 7.85 g of N-((1R)-1-hydroxymethyl-2-phenylethyl)-N-methylcarbarmic acid tert-butylester.

$^1$H-NMR (CDCl$_3$): δ1.32–1.40 (br, 9H); 2.55–2.95 (m, 5 H); 3.65–3.67 (br, 2 H); 4.10–4.35 (br, 1H); 7.05–7.35 (m, 5 H).

((2R) -2-((tert-Butoxycarbonyl)methylamino)-3-phenylpropoxy)acetic acid ethylester

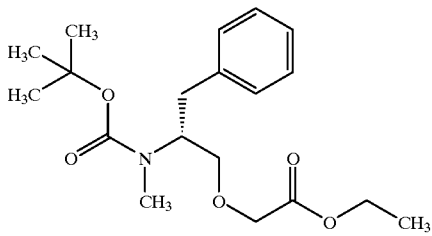

N-((1R)-1-Hydroxymethyl-2-phenylethyl)-N-methylcarbamaic acid (3.98 g, 15.0 mmol) was dissolved in 1,2-dichloroethane (150 ml). The solution was warmed to 75–80° C. Rhodium(II) acetate (0.1 g, 0.4 mmol) was added. During a time of 6 h a solution of ethyl diazoacetate (2.4 ml, 22.5 mmol) in dichloromethane (100 ml) was added. After 3 h another portion of rhodium(II) acetate (0.1 g, 0.4 mmol) was added. After all ethyl diazoacetate was added, the solution was cooled to room temp. It was filtrated through a plug of celite. The solvent was removed in vacuo. The crude product was chromatographed on silica (100 g) to give 1.53 g of ((2R)-2-((tert-butoxycarbonyl)methylamino)-3-phenylpropoxy) acetic acid ethyl ester.

$^1$H-NMR (CDCl$_3$): δ1.28 (m, 3 H); 1.39 and 1.48 (both s, together 9H); 2.65–2.95 (m, 9 H); 3.58 (m, 1 H); 3.67 (br, 1H); 3.98–4.27 (m, 4 H); 4.35–4.55 (br, 1H); 7.10–7.30 (m, 5 H).

((2R)-2-((tert-Butoxycarbonyl)methylamino)-3-phenylpropoxy)acetic acid

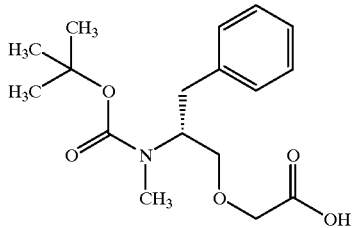

((2R)-2-((tert.-butoxycarbonyl)methylamino)-3-phenylpropoxy)acetic acid ethyl ester (0.60 g, 1.71 mmol) was dissolved in dioxane (5 ml). A solution of lithium hydroxide (0.05 g, 2.20 mmol) in water (2 ml) was added. The solution was stirred at room temp. for 56 h. Ethyl acetate (10 ml) and water (2 ml) were added. The phases were separated. The aqueous phase was extracted with ethyl acetate (10 ml). The combined organic layers were extracted with 1N sodium hydroxide solution (20 ml). The combined aqueous phases were acidified with a 1M sodium hydrogensulfate solution (pH=2) and extracted with ethyl acetate (2×20 ml). These ethyl acetate layers were combined and dried over magnesium sulfate. The solvent was removed in vacuo to give 0.38 g of crude ((2R)-2-((tert-butoxycarbonyl) methylamino)-3-phenylpropoxy) acetic acid, that was used for the following steps.

$^1$H-NMR (DMSO d$_6$): δ1.15 and 1.27 (both s, together 9H); 2.55–2.70 (m, 5 H); 3.45–3.65 (m, 2 H); 4.00–4.10 (m, 2 H); 4.30–4.50 (m, 1H); 7.15–7.35 (m, 5 H); 13.60 (br, 1H).

N,N-Dimethyl-2-((2R)-2-methylamino-3-phenylpropoxy)acetamide

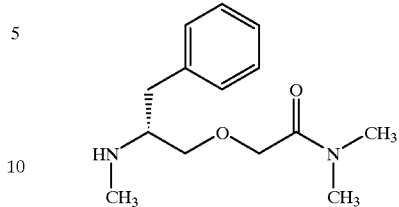

((2R)-2-((tert-Butoxycarbonyl)methylamino)-3-phenylpropoxy)acetic acid (0.37 g, 1.14 mmol) and 1-hydroxy-7-azabenzotriazole (0.26 g, 1.14 mmol) were dissolved in N,N-dimethylformamide (7 ml). N-ethyl-N'-(3-dimethylaminopropyl)carbodiimide hydrochloride (0.26 g, 1.37 mmol) was added. The solution was stirred for 30 min. A 33% solution of dimethylamine in ethanol (0.33 ml, 1.26 mmol) was added. The solution was stirred over night. Water (20 ml) and ethyl acetate (15 ml) were added. The organic phase was washed with a 1M solution of sodium hydrogensulfate (30 ml) and a saturated solution of sodium hydrogencarbonate (30 ml). It was dried over magnesium sulfate. The solvent was removed in vacuo. The crude product was purified by column chromatography on silica (15 g) using ethyl acetate and dichloromethane (1:1) as eluent. This product was dissolved in dichloromethane (3 ml) and was cooled to 0° C. Trifluoroacetic acid (1 ml) was added. The solution was stirred at 020 C. for 20 min. The solvent was removed in vacuo. The residue was dissolved in dichloromethane (10 ml) and 1N sodium hydroxide solution (10 ml). The phases were separated. The aqueous phase was extracted with dichloromethane (4×10 ml). The combined organic layers were dried over magnesium sulfate. The solvent was removed in vacuo to give 140 mg of crude N,N-dimethyl-2-((2R)-2-methylamino-3-phenylpropoxy) acetamide, which was used for further syntheses.

$^1$H-NMR (CDCl$_3$): δ2.25 (s, 1H); 2,45 (s, 3 H); 2.60–3.10 (m, 3 H); 3.94 (s, 1 H); 3.99 (s, 3H); 3.35–3.55 (m, 2 H); 4.15 (s, 2 H); 7.10–7.40 (m, 5 H).

HPLC: R$_t$=12.18 min (Method b).

N-((1R)-1-{N-[(1R)-1-(((Dimethylcarbamoyl)methoxy)methyl)-2-phenylethyl]-N-methylcarbamoyl}-2-{2-naphthyl}ethyl)-N-methylcarbamic acid tert-butylester

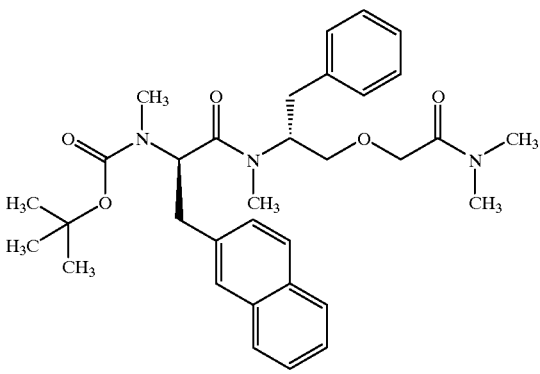

N,N-Dimethyl-2-((2R)-2-methylamino-3-phenylpropoxy)acetamide (126 mg, 0.50 mmol), (2R)-2

((tert-butoxycarbonyl)methylamino)-3-(2-naphthyl) propionic acid (250 mg, 0.75 mmol) and 1-hydroxy-7-azabenzotriazole (103 mg, 0.76 mmol) were dissolved in dichloromethane (6 ml) and N,N-dimethylformamide (5 ml) and then stirred 30 min at 0° C. with N-ethyl-N'-(3-dimethylaminopropyl)-carbodiimide hydrochloride (146 mg). Diisopropylethylamine (87 µl) was added and stirring was continued for 1 h at 0° C. After this the dichloromethane was evaporated from the mixture by a stream of nitrogen and ethyl acetate (25 ml) was added. The mixture was extracted sequentially with 5% aqueous sodium hydrogencarbonate (2×25 ml), 5% aqueous potassium hydrogensulfate (2×25 ml) and water (25 ml) and the organic phase was dried (sodium sulfate) and concentrated in vacuo yielding 265 mg of crude N-((1R)-1-{N-[(1R)-1-(((dimethylcarbamoyl) methoxy)methyl)-2-phenylethyl]-N-methylcarbamoyl}-2-{2-naphthyl}ethyl)-N-methylcarbamic acid tert-butylester.

3-Aminomethyl-N-((1R)-1-{N-[(1R)-1-(((dimethylcarbamoyl)methoxy)methyl)-2-phenylethyl]-N-methylcarbamoyl}-2-(2-naphthyl) ethyl)-N-methylbenzamide

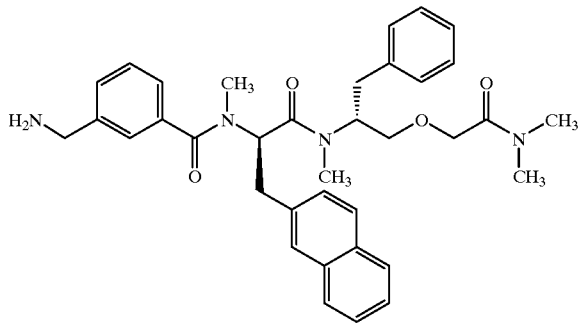

Half of the crude N-((1R)-1-{N-[(1R)-1-(((dimethylcarbamoyl)methoxy)methyl)-2-phenylethyl]-N-methylcarbamoyl}-2-{2-naphthyl}ethyl) -N-methylcarbamic acid tert-butylester (132 mg, 0.23 mmol) was dissolved in a mixture of dichloromethane and trifluoroacetic acid 1:1 (2 ml) and stirred for 10 min. The mixture was concentrated by a stream of nitrogen and the resulting oil was redissolved in 1 ml 1N hydrochloric acid, diluted with water to a volume of 50 ml and lyophilized. This lyophilized product was dissolved in dichloromethane (5 ml) and diisopropylethyl amine (171 µl) was added. To this mixture was added a solution in dichloromethane (5 ml) of 3-tert-butyloxycarbonylaminomethylbenzoic acid (503 mg, 2.0 mmol) which immediately before had been converted to the symmetrical anhydride by stirring with N-ethyl-N'-(3-dimethylaminopropyl)-carbodiimide hydrochloride (191.6 mg, 1.0 mmol) for 15 min. The reaction mixture was then concentrated to an oil and redissolved in ethyl acetate (25 ml). This mixture was extracted sequentially with 5% aqueous sodium hydrogencarbonate (50 ml), 5% aqueous potassium hydrogen-sulfate (50 ml) and water (50 ml) and the organic phase was dried (sodium sulfate) and concentrated by a stream of nitrogen to dryness. This product was dissolved in a mixture of dichloromethane and trifluoroacetic acid 1:1 (4 ml). After 10 min the mixture was concentrated by a stream of nitrogen and the resulting oil was redissolved in 5 ml 70% acetonitrile/0.1% trifluoroacetic acid and diluted with water to a volume of 50 ml. The crude product of the title compound was then purified by semipreparative HPLC in four runs on a 25 mm×250 mm column packed with 7µ C-18 silica which was preequilibrated with 29% acetonitrile in 0.05M ammonium sulfate, which was adjusted to pH 2.5 with 4M sulfuric acid.

The column was eluted with a gradient of 29%–39% acetonitrile in 0.05M ammonium sulfate, pH 2.5 at 10 ml/min during 47 min at 40° C. and the peptide containing fractions were collected, diluted with 3 volumes of water and applied to a Sep-Pak® C18 cartridge (Waters part. #:51910 ) which was equilibrated with 0.1% trifluoroacetic acid. The peptide was eluted from the Sep-Pak® cartridge with 70% acetonitrile/0.1% trifluoroacetic acid and isolated from the eluate by lyophilisation after dilution with water.

The final product obtained was characterised by analytical RP-HPLC (retention time) and by Plasma desorption mass spectrometry (molecular mass). The molecular mass found (MH⁺: 592.9 amu) agreed with the expected structure (teor. MH⁺: 593.4 amu) within the experimental error of the method.

The RP-HPLC analysis was performed using UV detection at 214 nm and a Vydac 218TP54 4.6 mm×250 mm 5µ C-18 silica column (The Separations Group, Hesperia) which was eluted at 1 ml/min at 42° C. Two different elution conditions were used:

A1: The column was equilibrated with 5% acetonitrile in a buffer consisting of 0.1M ammonium sulfate, which was adjusted to pH 2.5 with 4M sulfuric acid and eluted by a gradient of 5% to 60% acetonitrile in the same buffer during 50 min.

B1: The column was equilibrated with 5% acetonitrile/ 0.1% trifluoroacetic acid/water and eluted by a gradient of 5% acetonitrile/0.1% trifluoroacetic acid/water to 60% acetonitrile/0.1% trifluoroacetic acid/water during 50 min.

The retention time using elution conditions A1 and B1 was found to be 30.92 min and 35.15 min, respectively.

Example 15

5-((1R)-1-(((2R)-2-(((2E)-4-Amino-4-methylpent-2-enoyl)methylamino)-3-(2-naphthyl)propionyl) methylamino)-2-phenylethyl)-[1,3,4]-oxadiazole-2-carboxylic acid amide

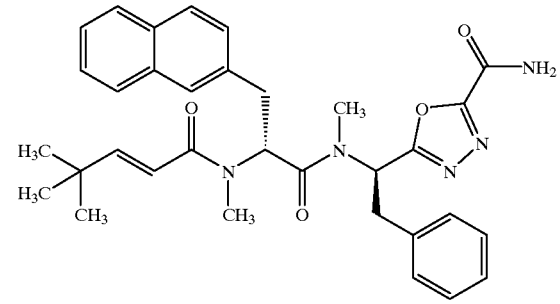

(2R)-2-((tert-Butoxycarbonyl)methylamino)-3-phenylpropionic acid ethyl ester

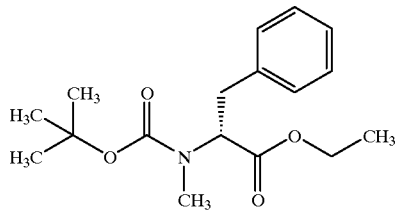

(2R)-2-((tert-Butoxycarbonyl)methylamino)-3-phenylpropionic acid (4.0 g, 14.27 mmol) was dissolved in dichloromethane (5 ml) and ethanol (0.95 ml, 16.27 mmol). 4-Dimethylaminopyridine (0.19 g, 1.57 mmol) was added. The solution was cooled to 0° C. and N-(3-dimethylaminopropyl)-N'-ethylcarbodiimide hydrochloride (2.98 g, 15.55 mmol) was added. The reaction mixture was stirred for 2 h at 0° C. for 16 h at room temp. The solvent was removed in vacuo and the residue was dissolved in ethyl acetate/water (30 ml/30 ml). The phases were separated. The organic phase was washed with a saturated solution of sodium hydrogencarbonate and water and dried over magnesium sulfate. The crude product was purified by flash chromatography on silica (180 g) with ethyl acetate/heptane 1:2 to give 1.95 g of (2R)-2-((tert-butoxycarbonyl)methylamino)-3-phenylpropionic acid ethylester.

$^1$H-NMR (CDCl$_3$): δ1.15–1.50 (m, 12 H); 2.71 (m, 3 H); 3.00 (m, 1 H); 3.80 (m, 1 H); 4.20 (br q, 2 H); 4.55 and 4.90 (both br dd, together 1 H); 7.10–7.40 (m, 5 H).

((1R)-1-Hydrazinocarbonyl-2-phenylethyl)methylcarbamic acid tert-butyl ester

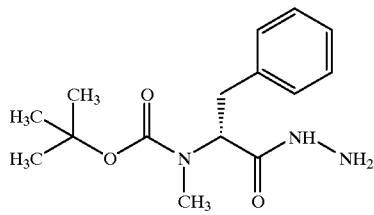

(2R)-2-((tert-Butoxycarbonyl)methylamino)-3-phenylpropionic acid ethylester (1.9 g, 6.16 mmol) was dissolved in anhydrous ethanol (15 mL). Hydrazine hydrate (3.0 ml, 61.6 mmol) was added dropwise. The solution was stirred at room temp. over night. The solvent was removed in vacuo. The residue was dissolved in ethyl acetate (40 ml) and washed with water (40 ml). The organic phase was dried over magnesium sulfate. After removal of the solvent in vacuo 1.40 g of curde ((1R)-1-hydrazinocarbonyl-2-phenylethyl)methylcarbamic acid tert-butylester was obtained, which was used for the further synthesis.

$^1$H-NMR (CDCl$_3$): δ1.20–1.50 (m, 9 H); 2.76 (s, 3 H); 3.00 (m, 1 H); 3.35 (m, 1 H); 3.85 (br, 2 H); 4.75 and 4.85 (both m, together 1 H); 7.10–7.40 (m, 5 H); 7.45 (br, 1 H).

1-((2R)-2-((tert-Butoxycarbonyl)methylamino)-3-phenylpropionyl)-2-ethoxycarbonylformylhydrazine

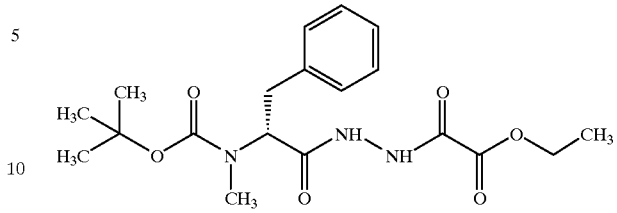

((1R)-1-Hydrazinacarbonyl-2-phenylethyl)methylcarbamic acid tert-butylester (1.4 g, 4.76 mmol) was dissolved in dichloromethane (40 ml). Triethylamine (0.8 ml, 5.71 mmol) was added and the solution was cooled to −15° C. Ethyl oxalyl chloride (0.59 ml, 5.24 mmol) was added dropwise. The solution was stirred for 15 min at −15° C. It was warmed to room temp. and extracted with water (2×20 ml) and 5% citric acid (30 ml) and washed with a saturated solution of sodium hydrogencarbonate. The organic layer was dried over magnesium sulfate. The solvent was removed in vacuo and the crude product was purified by flash chromatography on silica (140 g) with ethyl acetate/dichloromethane 1:3 to give 1.40 g of 1-((2R)-2-((tert-butoxycarbonyl)methylamino)-3-phenylpropionyl)-2-ethoxycarbonylformylhydrazine.

$^1$H-NMR (CDCl$_3$): δ1.30–1.50 (m, 12 H); 2.80 (br, 3 H); 3.05 (m, 1 H); 3.35 (m, 1 H); 4.37 (br m, 2 H); 4.82 and 4.95 (br and br t, together 1H); 7.05–7.35 (m, 5 H); 8.60, 8.95, 9.15, 9.45 (all br, together 2 H).

5-((1R)-1-((tert-Butoxycarbonyl)methylamino)-2-phenylethyl)-[1,3,4]oxadiazole-2-carboxylic acid ethylester

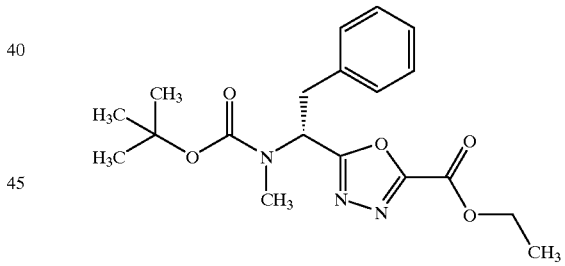

1-((2R)-2-((tert-Butoxycarbonyl)methylamino)-3-phenylpropionyl)-2-ethoxycarbonylformylhydrazine (1.4 g, 3.55 mmol) was dissolved in ether (25 ml) and THF (10 ml). Pyridine (1.44 ml 17.75 mmol) was added, and the solution was cooled to 0° C. Thionyl chloride (0.3 ml, 3.90 mmol) was added dropwise. The reaction mixture was stirred at 0° C. for 2 h. The precipitation was filtered off. The solvent was removed in vacuo without warming. The residue was dissolved in toluene (25 ml) and the solution was warmed to reflux for 2 h. The solvent was removed in vacuo. The crude product was purified by flash chromatography on silica (70 g) with ethyl acetate/dichloromethane 1:2 to give 721 mg of 5-((1R)-1-((tert-butoxycarbonyl)methylamino)-2-phenylethyl)-[1,3,4]oxadiazole-2-carboxylic acid ethylester.

$^1$H-NMR (CDCl$_3$): δ1.35 (br d, 9 H); 1.47 (t, 3 H); 2.70 (br, 3 H); 3.30 (br, 1 H); 3.50 (br, 1 H); 4.52 (br, 2 H); 5.55 and 5.88 (both br, together 1H); 7.15–7.40 (m, 5 H).

((1R)-1-(5-Carbamoyl-[1,3,4]oxadiazol-2-yl)-2-phenylethyl)methyl carbamic acid tert-butylester

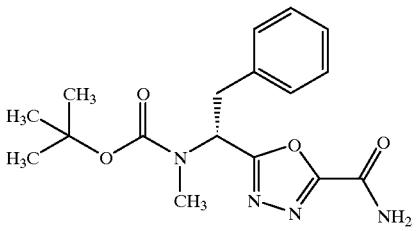

5-((1R)-1-((tert-Butoxycarbonyl)methylamino)-2-phenylethyl)-[1,3,4]oxadiazole-2-carboxylic acid ethylester (600 mg, 1.6 mmol) was dissolved in THF (4 ml) and added to refluxing ammonia. The solution was stirred for 3 h. The the ammonia was removed in a stream of nitrogen. The residue was dissolved in ethyl acetate/10% sodium hydrogensulfate solution (20 ml/20 ml). The phases were separated and the organic phase was washed with a saturated solution of sodium hydrogencarbonate and dried over magnesium sulfate. The solvent was removed in vacuo. The crude product was purified by flash chromatography on silica (40 g) with ethyl acetate/heptane 2:1 to give 383 mg of ((1R)-1-(5-carbamoyl-[1,3,4]oxadiazol-2-yl)-2-phenylethyl)methyl carbamic acid tert-butylester.

$^1$H-NMR (CDCl$_3$): δ1.30 (br, 9 H); 2.75 (br d, 3 H); 3.30 (dd, 1 H); 3.50 (br, 1 H); 5.–55 and 5.85 (both br, together 1 H); 6.27 (br, 1 H); 7.10 (br, 1 H); 7.20–7.40 (m, 5 H).

5-((1R)-1-Methylamino-2-phenylethyl)-[1,3,4]oxadiazole-2-carboxylic acid amide

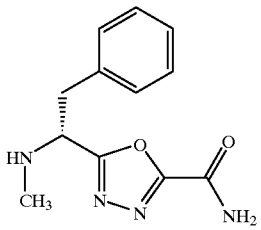

((1R)-1-(5-Carbamoyl-[1,3,4]oxadiazol-2-yl)-2-phenylethyl)methylcarbamic acid tert-butylester (350 mg, 1.01 mmol) was dissolved in dichloromethane (6 ml). The solution was cooled to 0° C. Trifluoroacetic acid (2 ml) was added dropwise. The solution was stirred for 30 min. The solvent was removed in vacuo. The residue was dissolved in dichloromethane (6 ml) and the solvent was removed in vacuo. The residue was again dissolved in dichloromethane (6 ml) and the solvent was removed in vacuo. The residue was dissolved in dichloromethane (10 ml). This phase was washed with water. The aqueous phase was lyophilized to give 247 mg of crude 5-((1R)-1-methylamino-2-phenylethyl)-[1,3,4]oxadiazole-2-carboxylic acid amide, which was used for the further synthesis.

$^1$H-NMR (DMSO d$_6$): δ2.65 (s, 3H); 3.35 (dd, 1 H); 3.62 (dd, 1 H); 5.20 (dd, 1 H); 7.10–7.40 (m, 5 H); 8.35 (s, 1 H); 8.68 (s, 1 H).

((1R)-1-(((1R)-1-(5-Carbamoyl-[1,3,4]oxadiazol-2-yl)-2phenylethyl)methylcarbamoyl)-2-(2-naphthyl)ethyl)methylcarbamic acid tert-butylester

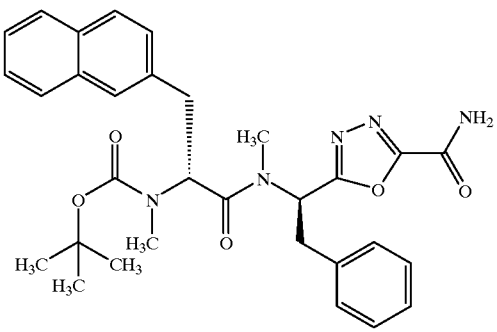

5-((1R)-1-Methylamino-2-phenylethyl)-[1,3,4]oxadiazole-2-carboxylic acid amide (240 mg, 0.98 mmol), (R)-2-((tert-butoxycarbonyl)methylamino)-3-(2-naphthyl)propionic acid (320 mg, 0.98 mmol) and 1-hydroxy-7-azabenzotriazole (133 mg, 0.98 mmol) were dissolved in dichloromethane (8 ml) and DMF (4 ml). The solution was cooled to 0° C. and N-(3-dimethylaminopropyl)-N'-ethylcarbodiimide hydrochloride (230 mg, 1.18 mmol) was added. After 10 min triethylamine (0.35 ml, 2.46 mmol) was added. The solution was stirred for 1h at 0° C. and subsequently for 16 h at room temp. The solution was diluted with ethyl acetate (30 ml) and water (20 ml). The phases were separated and the aqueous phase was extracted with ethyl acetate (20 ml). The combined organic layers were washed with a saturated solution of sodium hydrogencarbonate (30 ml) and dried over magnesium sulfate. The solvent was removed in vacuo. The crude product was purified by flash chromatography on silica (50 g) with ethyl acetate to give 301 mg of ((1R)-1-(((1R)-1-(5-carbamoyl-[1,3,4]oxadiazol-2-yl)-2-phenylethyl) methylcarbamoyl)-2-(2-naphthyl)ethyl)methylcarbamic acid tert-butylester.

$^1$H-NMR (CDCl$_3$): δ0.84, 0.95, 1.07, 1.25 (all s, together 9 H); 2.05, 2.15, 2.42, 2.75, 2.76, 2.77, 2.87, 3.98 (all s, together 6 H); 6.90–7.90 (m, 12 H).

5-((1R)-1-(Methyl((2R)-2-methylamino-3-(2-naphthyl)propionyl)amino)-2-phenylethyl)-[1,3,4]oxadiazol-2-carboxylic acid amide

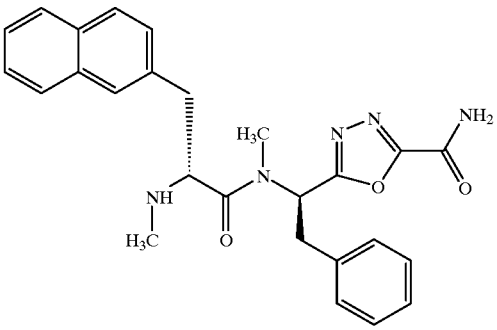

((1R)-1-(((1R)-1-(5-Carbamoyl-[1,3,4]oxadiazol-2-yl)-2-phenylethyl)methylcarbamoyl)-2-(2-naphthyl)ethyl) methylcarbamic acid tert-butylester (300 mg, 0.55 mmol) was dissolved in dichloromethane (3 ml) and cooled to 0° C. Trifluoroacetic acid (3 ml) was added dropwise. The solution was stirred for 5 min at 0° C. The solvent was removed in vacuo. The residue was dissolved in ethyl acetate (5 ml), and the solvent was removed in vacuo. The residue was dissolved in ethyl acetate (5 ml), and the solvent was removed in vacuo. The residue was dissolved in 3M hydrogen chloride in ethyl acetate (5 ml), and the solvent was removed in vacuo. The residue was dissolved in 3M hydrogen chloride in ethyl acetate (5 ml), and the solvent was removed in vacuo to give 238 mg of crude 5-( (1R)-1-(methyl((2R)-2-methylamino-3-(2-naphthyl)propionyl) amino)-2-phenylethyl)-[1,3,4)]oxadiazol-2-carboxylic acid amide, which was used for the further synthesis.

$^1$H-NMR (CDCl$_3$): δ2.40 (s, 3H); 2.55–4.40 (m, 9 H); 7.10–7.90 (m, 9H).

((E)-3-(((1R)-1-(((1R)-1-(5-Carbamoyl-[1,3,4] oxadiazol-2-yl)-2-phenylethyl)methylcarbamoyl)-2-(2-naphthyl)ethyl)methylcarbamoyl)-1,1-dimethylallyl)carbamic acid tert-butylester

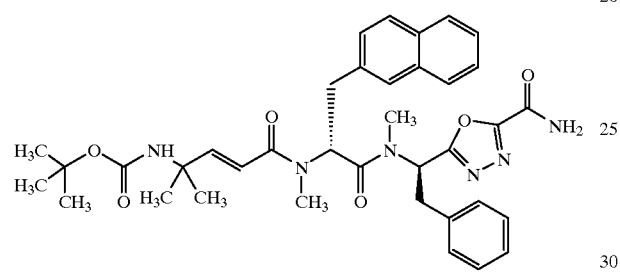

(2E)-4-tert-Butoxycarbonylamino-4-methylpent-2-enoic acid (143 mg, 0.62 mmol) was dissolved in dichloromethane (4 ml). 1-Hydroxy-7-azabenzotriazole (85 mg, 0.62 mmol) and subsequently N-(3-dimethylaminopropyl)-N'-ethylcarbodiimide hydrochloride (119 mg, 0.62 mmol) were added. The solution was stirred for 15 min at room temp. 5-((1R)-1-(Methyl((2R)-2-methylamino-3-(2-naphthyl) propionyl)amino)-2-phenylethyl)-[1,3,4]oxadiazol-2-carboxylic acid amide (230 mg, 0.52 mmol) was added. The solution was stirred for 5 min and ethyldiisopropylamine (0.11 ml, 0.62 mmol) was given to the reaction mixture. It was stirred for 16 h at room temp., diluted with ethyl acetate (20 ml) and extracted with water (20 ml). The phases were separated. The aqueous phase was extracted with ethyl acetate (2×10 ml). The combined organic layers were washed with a saturated solution of sodium hydrogencarbonate and dried over magnesium sulfate. The crude product was purified by flash-chromatography on silica (40 g) with dichloromethane/ethyl acetate 1:1 to give 126 mg of ((E)-3-(((1R)-1-(((1R)-1-(5-carbamoyl-[1,3,4]oxadiazol-2-yl)-2-phenylethyl)methylcarbamoyl)-2-(2-naphthyl)ethyl) methylcarbamoyl)-1,1-dimethylallyl)carbamic acid tert-butyl ester.

$^1$H-NMR (CDCl$_3$): δ1.1–1.5 (m, 15 H); 2.6–3.7 (m, 12H).
HPLC (Method b): R$_t$=44.95 min.
PDMS: 668.8 ([M]$^+$)

((E)-3-(((1R)-1-(((1R)-1-(5-Carbamoyl-[1,3,4]oxadiazol-2-yl)-2-phenylethyl)methylcarbamoyl)-2-(2-naphthyl)ethyl) methylcarbamoyl)-1,1-dimethylallyl)carbamic acid tert-butylester (120 mg, 0.18 mmol) was dissolved in dichloromethane (3 ml). The solution was cooled to 0° C. Trifluoroacetic acid (3 ml) was added dropwise. The reaction mixture was stirred for 5 min at 0° C. The solvent was removed in vacuo-without warming. The residue was dissolved in dichloromethane (5 ml) and the solvent was removed in vacuo. This last procedure was repeated two times. The residue was dissolved in water (5 ml) and 1N hydrochloric acid (1 ml, 1 mmol) was added. The solvent was removed in vacuo. The residue was dissolved in 3M hydrogen chloride in ethyl acetate (3 ml), and the solvent was removed in vacuo. This last procedure was repeated. The crude product was purified by HPLC-chromatography on a 25 mm×250 mm 5µ C18 silica column with a gradient of 28% to 38% acetonitrile in a 0.1M ammonium sulfate buffer, which was adjusted to pH 2.5 with 4M sulfuric acid to give 64 mg of the title compound.

HPLC (Method b): R$_t$=30.133 min
PDMS: 569.6 ([M+H]$^+$)

Example 16

Piperidine-4-carboxylic acid N-methyl-N-{-1 (methyl-[1-(3-methyl-[1,2,4]oxadiazol-5-yl)-2-(2-naphthyl)ethyl]carbamoyl)-2-(2-naphthyl) ethyl}amide

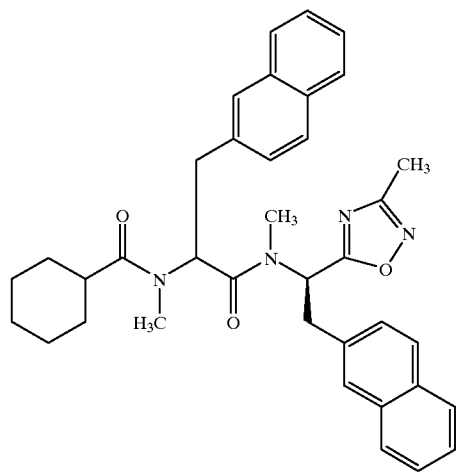

Prepared according to method E.

N-Methyl-N-{(1R)-1-{N-methyl-N-[(1R)-1-(3-methyl-[1,2,4]oxadiazol-5-yl)-2-(2-naphthyl)ethyl] carbamoyl}-2-(2-naphthyl)ethyl}carbamic acid tertbutylester

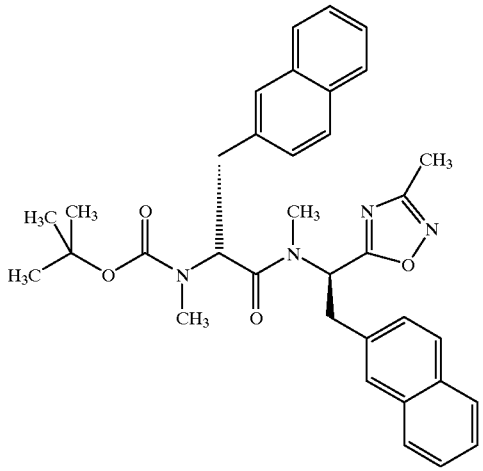

N-(3-Dimethylaminopropyl)-N'-ethylcarbodiimide hydrochloride (1.34 g, 7.0 mmol) and 1-hydroxy-7- azabenzotriazole (0.95 g, 7.0 mmol) were added to a solution of (R) N-methyl-N-tert-butoxycarbonyl-3-(2-naphthyl) alanine (2.31 g, 7.0 mmol) in N,N-dimethylformamide (50 ml). After 30 min at 20° C. a mixture of (R) N-methyl-N-{1-(3-methyl-[1,2,4]oxadiazol-5-yl)-2-(2-naphthyl) ethyl}amine hydrochloride (1.52 g, 5.0 mmol) and triethylamine (0.51 g, 5.0 mmol) in N,N-dimethylformamide (10 ml) were added. After 18 h at 20° C. the reaction mixture was poured on water (250 ml) and extracted several times with ethyl acetate (total 130 ml). The collected organic phases were washed with aqueous citric acid (10%, 50 ml), a saturated solution of sodium hydrogencarbonate (50 ml) and water (3×50 ml). After drying (magnesium sulfate) the solution was concentrated in vacuo and the residue was chromatographed on silica (110 g) using ethyl acetate and heptane (1:1) as eluent to give 2.4 g of N-methyl-N-{(1R)-1-{N-methyl-N-[(1R)-1-(3-methyl-[1,2,4]-oxadiazol-5-yl)-2-(2-naphthyl)ethyl]carbamoyl}-2-(2-naphthyl) ethyl}carbamic acid tert-butylester as a foam.

HPLC: $R_t$=36.5 min (method a)

(2R)-2-Methylamino-N-methyl-N-[(1R)-1-(3-methyl-[1,2,4]oxadiazol-5-yl)-2-(2-naphthyl)ethyl]-3-(2-naphthyl)propionamide, trifluoroacetic acid

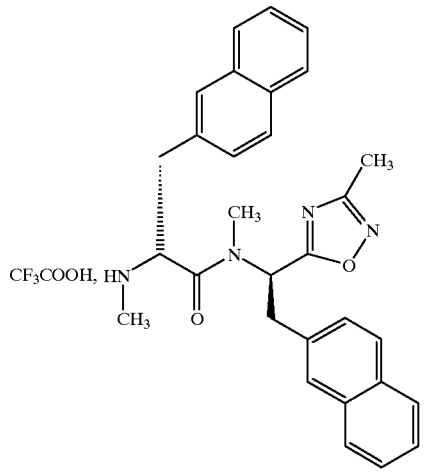

5 N-Methyl-N-{(1R)-1-({-methyl-N-[(1R)-1(3-methyl-[1,2,4]oxadiazol-5-yl)-2-(2-naphthyl)ethyl]carbamoyl}-2-(2-naphthyl)ethyl}carbamic acid tert-butylester (2.4 g, 4.2 mmol) was dissolved in a mixture of trifluoroacetic acid (40 ml) and dichloromethane (40 ml) at 20° C. After 10 min the reaction mixture was concentrated in vacuo and coevaporated from heptane (80 ml) and dichloromethane (80 ml). The residue was crystallised from ethyl acetate to give 1.12 g of (2R)-2-methylamino-N-methyl-N-[(1R)-1-(3-methyl-[1,2,4]oxadiazol-5-yl)-2-(2-naphthyl)ethyl]-3-(2-naphthyl) propionamide, trifluoroacetic acid.

mp 184–188° C.

$^1$H-NMR (DMSO-$d_6$) δ1.52(s,3H); 2.32(s,3H); 2.68(s, 3H); 3.03(dd,1H); 3.22(dd, 1H); 3.55(dd, 1H); 4.62(t, 1H); 6.35(dd, 1H); 7.25–7.95(m, 14H).

HPLC: $R_t$=24.9 min (Method a)

Calculated for $C_{30}H_{30}N_4O_2$, $CF_3COOH$, 0.25EtOAc:
C, 64.49; H, 5.41; N, 9.12%; found:
C, 65.01; H, 5.35; N, 9.32%.

4-{N-Methyl-N-=(1R)-1-[N-methyl-N-((1R)-1-(3-methyl-[1,2,4]oxadiazol-5-yl)-2-(2-naphthyl)ethyl) carbamoyl]-2-(2-naphthyl)ethyl) carbamoyl}piperidine-1-carboxylic acid tert-butyl ester

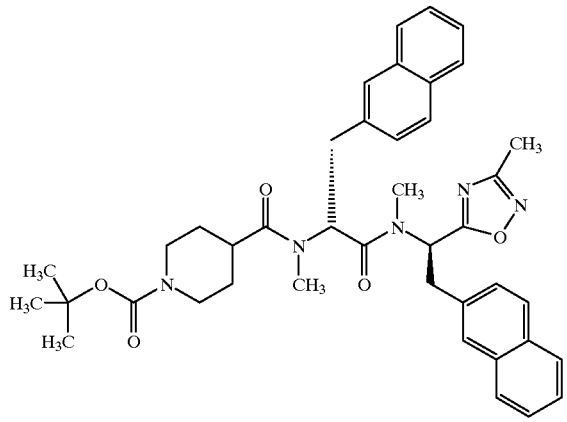

N-(3-Dimethylaminopropyl)-N'-ethylcarbodiimide hydrochloride (0.37 g, 1.91 mmol) and 1-hydroxybenzotriazole monohydrate (0.26 g, 1.91 mmol) were added to a solution of N-tert-butoxycarbonyl-4-piperidine carboxylic acid (0.44 g, 1.91 mmol) in N,N-dimethylformamide (5 ml). After 45 min at 20° C. a mixture of (2R)-2-methylamino-N-methyl-N-[(1R)-1-(3-methyl-[1,2,4]oxadiazol-5-yl)-2-(2-naphthyl) ethyl-3-(2-naphthyl)] propionamide, trifluoroacetic acid (0.81 g, 1.37 mmol) and triethylamine (0.19 g, 1.37 mmol) in N,N-dimethylformamide (10 ml) were added. After 18 h at 20° C. the reaction mixture was poured on water (100 ml) and extracted several times with ethyl acetate (total 70 ml). The organic phases were collected and washed with aqueous citric acid (10%, 20 ml), a saturated solution of sodium hydrogencarbonate (20 ml) and water (3×20 ml). After drying (magnesium sulfate) the solution was concentrated in vacuo and the residue was chromatographed on silica (80 g) using ethyl acetate and heptane (3:2) as eluent to give 0.88 g of 4-{N-methyl-N-{(1R)-1-[N-methyl-N-((1R)-1-(3-methyl-[1,2,4]oxadiazol-5-yl)-2-(2-naphthyl)ethyl) carbamoyl]-2-(2-naphthyl)ethyl)carbamoyl}piperidine-1-carboxylic acid tert-butyl ester.

HPLC: $R_t$=36.1 min (Method a)

4-{N-Methyl-N-{(1R)-1-[N-methyl-N-((1R)-1-(3-methyl-[1,2,4]oxadiazol-5-yl)-2-(2-naphthyl)ethyl) carbamoyl]-2-(2-naphthyl)ethyl)carbamoyl}piperidine-1-carboxylic acid tert-butyl ester (0.88 g, 1.28 mmol) was dissolved in a mixture of trifluoroacetic acid (12 ml) and dichloromethane (12 ml). After 10 min at 20° C. the reaction mixture was concentrated in vacuo. The compound was chromatographed on silica (75 g) using a 10% mixture of ammonia in ethanol and dichloromethane (1:9) as eluent to give 0.56 g of two isomers of the title compound.

HPLC:
diastereoisomer I: $R_t$=25.24 min (Method a)
diastereoisomer II: $R_t$=25.26 min (Method a)
Calculated for $C_{30}H_{39}N_5O_3$, $H_2O$:
C, 71.15; H, 6.80; N, 11.52%; found:
C, 71.27; H, 6.68; N, 11.28%.

Example 17

Piperidine-4-carboxylic acid N-{1-(N-[methyl-N-[1-(3-methyl-[1,2,4]-oxadiazole-5-yl)-2-(2naphthyl)ethyl]carbamoyl)-2-(2-naphthyl)ethyl}amide

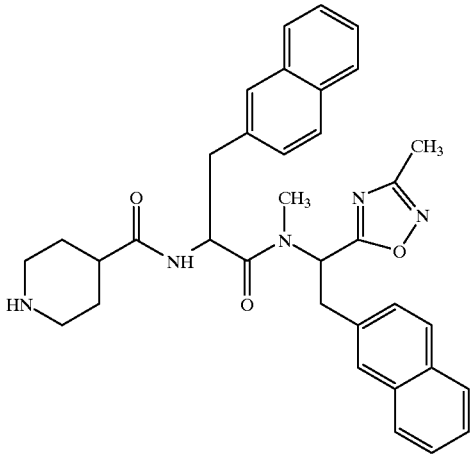

Prepared according to method E.

4-((1R)-1-{N-Methyl-N-[(1R)-1-(3-methyl-[1,2,4]oxadiazol-5-yl)-2-(2-naphthyl)ethyl]carbamoyl}-2-(2-naphthyl)ethyl)carbamoylpiperidine-1-carboxylic acid tert-butylester

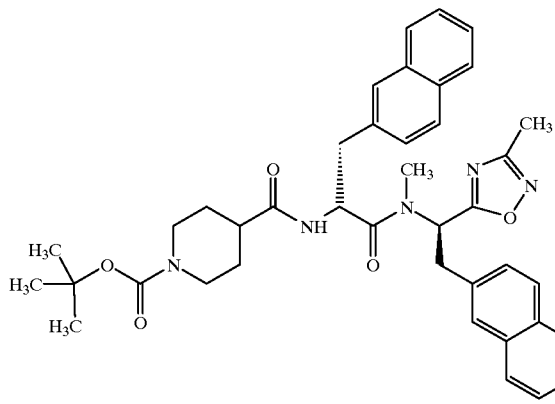

N-(3-Dimethylaminopropyl)-N'-ethylcarbodiimide hydrochloride (0.42 g, 2.2 mmol) and 1-hydroxybenzotriazole monohydrate (0.34 g, 2.2 mmol) were added to a solution of N-tert-butoxycarbonyl-4-piperidine carboxylic acid (0.50 g, 2.2 mmol) in N,N-dimethylformamide (5 ml). After 30 min at 20° C. a mixture of (2R)-2-amino-N-methyl-N-[(1R)-1-(3-methyl-[1,2,4]oxadiazol-5-yl)-2-(2-naphthyl)ethyl]-3-(2-naphthyl)propionamide, trifluoroacetic acid (0.9 g, 1.54 mmol) and triethylamine (0.16 g, 1.54 mmol) in N,N-dimethylformamide (10 ml) were added. After 18 h at 20° C. the reaction mixture was poured on water (85 ml) and extracted several times with ethyl acetate (total 90 ml). The organic phases were collected and washed with aqueous citric acid (10%, 15 ml), a saturated solution of sodium hydrogencarbonate (15 ml) and water (3×15 ml). After drying (magnesium sulfate) the solution was concentrated in vacuo and the residue was chromatographed on silica (110 g) using ethyl acetate and heptane (1:1) as eluent to give 0.50 g of 4-((1R)-1-{N-methyl-N-[(1R)-1-(3-methyl-[1,2,4]oxadiazol-5-yl)-2-(2-naphthyl)ethyl]carbamoyl}-2-(2naphthyl)ethyl)carbamoylpiperidine-1-carboxylic acid tert-butylester.

$^1$H-NMR (DMSO-$d_6$) δ2.40(s,3H); 2.95(s,3H); 3.45(dd, 1H); 3.60(dd,1H); 4.85(m,.1H); 6.08(m, 1H); 7.10(d, 1H); 7.40–7.90(m, 13H).

HPLC: $R_t$=34.0 min (Method a)

4-((1R)-1-{N-Methyl-N-[(1R)-1-(3-methyl-[1,2,4]oxadiazol-5-yl)-2-(2-naphthyl)ethyl]carbamoyl}-2-(2-naphthyl)ethyl)carbamoylpiperidine-1-carboxylic acid tert-butylester (0.50 g, 0.74 mmol) was dissolved in a mixture of trifluoroacetic acid (10 ml) and dichloromethane (10 ml). After 10 min at 20° C. the reaction mixture was concentrated in vacuo. The compound was chromatographed on silica (38 g) using a 10% mixture of ammonia in ethanol and dichloromethane (3:7) as eluent to give 0.26 g of the title compound.

$^1$H-NMR (DMSO-$d_6$) δ3.45(dd,$_1$H); 3.61(dd,1H); 4.72 (m,1H); 6.10(dd, 1H); 7.20(d, 1H); 7.40–8.00(m, 14H).

HPLC: $R_t$=24.8 min (Method a)

Calculated for $C_{35}H_{37}N_5O_3, 0.5\ H_2O$:

C, 71.90; H, 6.55; N. 11.98%; found:

C, 71.77; H, 6.52; N, 12.09%.

Example 18

5-{1-[N-(2-(piperidine-4-carbonylamino)-3-(2-naphthyl)propionyl)-N-methylamino]-2-(2-naphthyl)ethyl}-[1,2,4]oxadiazole-3-carboxylic acid (2-propyl)ester

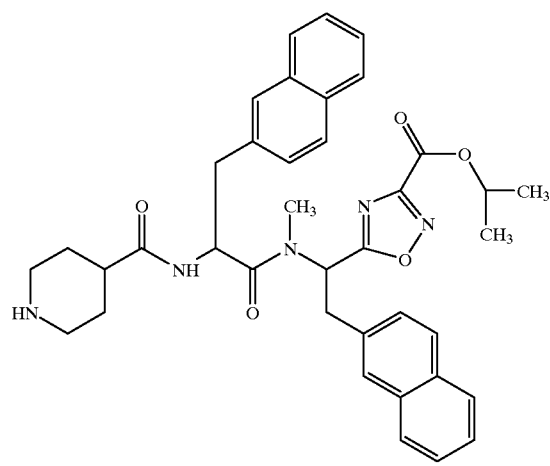

(R) 5-(1-Methylamino-2-(2-naphthyl)ethyl)-[1,2,4]oxadiazole-3-carboxylic acid (2-propyl)ester

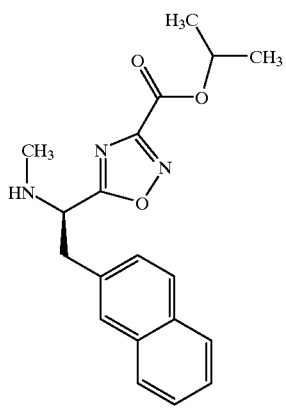

(R) 5-(1-methylamino-2-(2-naphthyl)ethyl)-[1,2,4]oxadiazole-3-carboxylic acid ethyl ester hydrochloride (1.64 g, 4.5 mmol) was suspended in 2-propanol (35 ml). After addition of tetraisopropyl titanate (1.3 g, 4.5 mmol) the reaction mixture was refluxed for 18 h. Hydrochloric acid (1N, 30 ml) was added and the reaction mixture was extracted with ethyl acetate (150 ml). The organic phase was washed with a saturated aqueous solution of sodium hydrogencarbonate (50 ml) and water (3×50 ml). After drying (magnesium sulfate) the solution was concentrated in vacuo to give 1.3 g of (R) 5-(1-methylamino-2-(2-naphthyl)ethyl)-[1,2,4]oxadiazole-3-carboxylic acid (2-propyl)ester that was used for the next step without further purification.

$^1$H-NMR (DMSO-d$_6$) δ1.31(d,6H); 2.21(d,3H); 3.3(m, 2H); 4.40(t,1H); 5.72(m,1H); 7.35–7.95(m, 7H).

HPLC: R$_t$=20.5 min (Method a)

5-{(1R)-1-[N-((2R)-2-tert-Butoxycarbonylamino-3-(2-naphthyl)-propionyl)-N-methylamino]-2-(2-naphthyl)ethyl}-[1,2,4]oxadiazole-3-carboxylic acid (2-propyl)ester

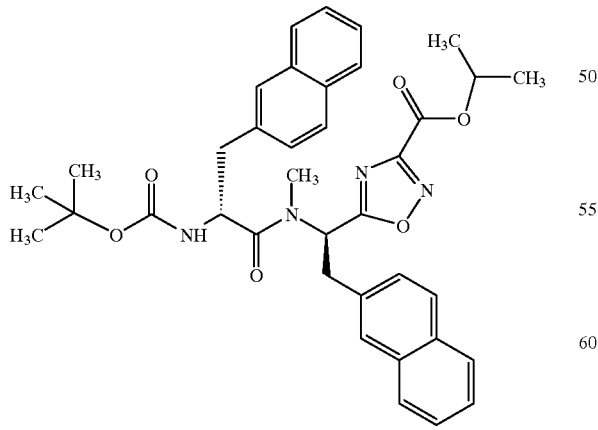

N-(3-Dimnethylaminopropyl)-N'-ethylcarbodiimide hydrochloride (2.15 g, 6.8 mmol) and 1-hydroxy-7-azabenzotriazole (0.93 g, 6.8 mmol) were added to a solution of (R) N-tert-butoxycarbonyl-3-(2-naphthyl)alanine (2.15 g, 6.8 mmol) in N,N-dimethylformamide (50 ml). After 30 min at 20° C. a solution of (R) 5-(1-methylamino-2-(2-naphthyl)ethyl)-[1,2,4]oxadiazole-3-carboxylic acid (2-propyl)ester (1.65 g, 4.9 mmol) in N,N-dimethylformamide (15 ml) was added. After 18 h the reaction mixture was poured on water (500 ml) and extracted several times with ethyl acetate (total 450 ml). The collected organic phases were washed with aqueous citric acid (10%, 75 ml), a saturated solution of sodium hydrogencarbonate (75 ml), water (3×75 ml) and dried (magnesium sulfate). The solution was concentrated in vacuo and the residue was chromatographed on silica (160 g) using ethyl acetate and heptane (1:2) as eluent to give 2.4 g of 5-{(1R)-1-[N-((2R)-2-tert-butoxycarbonylamino-3-(2-naphthyl)propionyl-N-methylamino]-2-(2-naphthyl)ethyl}-[1,2,4]oaxdiazole-3-carboxylic acid (2-propyl)ester.

HPLC: R$_t$=36.5 min (Method a)

5-{(1R)-1-[N-((2R)-2-Amino-3-(2-naphthyl)propionyl)-N-methylamino]-2-(2-naphthyl)ethyl}-[1,2,4]oxadiazole-3-carboxylic acid (2-propyl)ester, trifluoro acetic acid

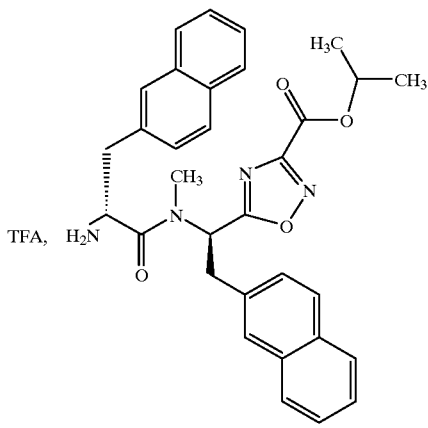

5-{(1R)-1-[N-((2R)-2-tert-Butoxycarbonylamino-3-(2-naphthyl)-propionyl)-N-methylamino]-2-(2-naphthyl)ethyl}-[1,2,4]oxadiazole-3-carboxylic acid (2-propyl)ester (2.1 g, 3.3 mmol) was suspended in a saturated mixture of trifluoroacetic acid and dichloromethane (1:1, 60 ml). After 10 min at 20° C., the reaction mixture was concentrated in vacuo to give 2.2 g of 5-{(1R)-1-[N-((2R)-2-amino-3-(2-naphthyl)propionyl)-N-methylamino]-2-(2-naphthyl)ethyl}-[1,2,4]oxadiazole-3-carboxylic acid (2-propyl)ester, trifluoroacetate, that was used for the next step without further purification.

4-((1R)-1-{N-[(1R)-1-(3-(2-propoxy)carbonyl-[1,2,4]oxadiazol-5-yl)-2-(2-naphthyl)ethyl]-N-methylcarbamoyl}-2-(2-naphthyl)-ethylcarbamoyl)piperidine-1-carboxylic acid tert-butyl ester

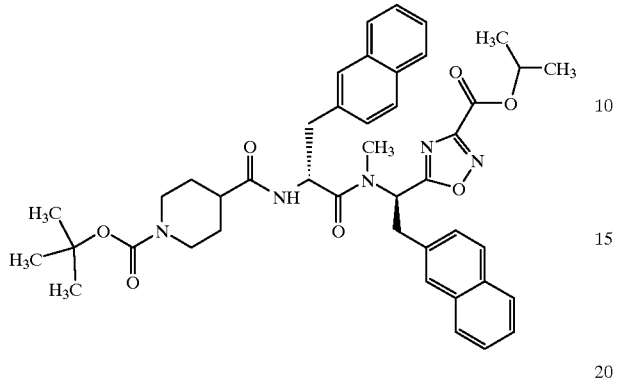

N-(3-Dimethylaminopropyl)-N'-ethylcarbodiimide hydrochloride (1.22 g, 6.35 mmol) and 1-hydroxybenzotriazole monohydrate (0.97 g, 6.35 mmol) were added to a solution of N-tert-butoxycarbonyl-4-piperidinecarboxylic acid (1.46 g, 6.35mmol) in N,N-dimethylformamide (20 ml). After 30 min at 20° C. a solution of 5-{(1R)-1-[N-(2R)-2-amino-3-(2-naphthyl)propionyl]-N-methylamino]-2-(2-naphthyl)ethyl}-[1,2,4]oxadiazole-3-carboxylic acid (2-propyl)ester (2.95 g, 4.53 mmol) and triethylamine (0.47 g, 4.53 mmol) in N,N-dimethylformamide (20 ml) was added. After 18 h at 20° C. the reaction mixture was poured on water (240 ml) and extracted several times with ethyl acetate (total 240 ml). The organic phases were collected and washed with aqueous citric acid (10%, 35 ml), a saturated solution of sodium hydrogencarbonate (35 ml) and water (3×35 ml). After drying (magnesium sulfate) the solution was concentrated in vacuo and purified by flash chromatography on silica gel (100 g) using ethyl acetate and heptane (1:1) to give 2.6 g of 4-((1R)-1-{N-([(1R)-1-(3-(2-propoxy)carbonyl-[1,2,4]oxadiazol-5-yl)-2-(2-naphthyl)ethyl]-carbamoyl}-2-(2-naphthyl)ethylcarbamoyl)piperidine-1-carboxylic acid tert-butyl ester.

$^1$H-NMR (DMSO-d$_6$) δ

HPLC: R$_t$=35.9 min (Method a)

4-((1R)-1-{N-([(1R)-1-(3-(2-Propoxy)carbonyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tert-butyl ester (1.0 g, 1.34 mmol) was dissolved in a mixture trifluoroacetic acid and dichloromethane (1:1, 25 ml). After 10 min at 20° C. the reaction mixture was concentrated in vacuo. The compound was purified by flash chromatography with silica gel (75 g) using a mixture of dichloromethane and 10% ammonia in ethanol (9:1) as eluent to give 0.77 g of the title compound.

$^1$H-NMR (DMSO-d$_6$) δ.

Example 19

5-{1-[N-(2-(piperidine-4-carbonylamino)-3-(2-naphthyl)propionyl)-N-methylamino]-2-(2-naphthyl)ethyl}-[1,2,4]oxadiazole-3-carboxylic acid, trifluoro acetate

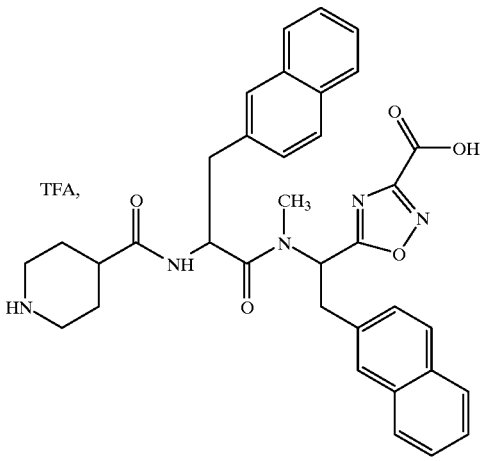

Prepared according to method E.

4-(1-{[1-(3-Carboxy-[1,2,4]oxadiazol-5-yl)-2-(2-naphthyl)ethyl]-N-methylcarbamoyl}-2-(2-naphthyl)-ethylcarbamoyl)piperidine-1-carboxylic acid tert-butylester

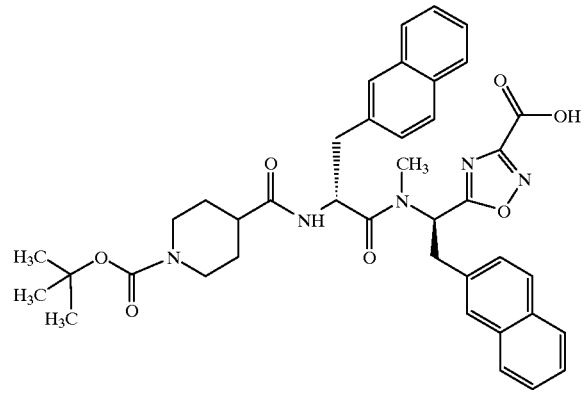

4-((1R)-1-{[(1R)-1-(3-Ethoxycarbonyl-[1,2,4]oxadiazol-5-yl)-2-(2-naphthyl)ethyl]-N-methylcarbamoyl}-2-(2-naphthyl)-ethylcarbamoyl)piperidine-1-carboxylic acid tert-butyl ester(0.79 g, 1.06 mmol) was dissolved in dioxane (5.5 ml). Water (3 ml) and solid lithium hydroxide (0.03 g) was added. After 18 h at 20° C. the reaction mixture was diluted with water (15 ml) and extracted with tert-butyl-methylether (2×10 ml). The aqueous phase was acidified with 1N aqueous sodium hydrogenphosphate (2.5 ml) and extracted with tert-butyl-methylether (3×40 ml). The collected organic phases were dried (magnesium sulfate) and concentrated in vacuo. The residue was chromatographed on silica (60 g) using a mixture of dichloromethane and 10% ammonia in ethanol (4:1) as eluent to give 0.41 g of 4-(1-{[1-(3-carboxy-[1,2,4]oxadiazol-5-yl)-2-(2-naphthyl)ethyl]-N-methylcarbamoyl}-2-(2-naphthyl)-ethylcarbamoyl)piperidine-1-carboxylic acid tert-butylester.

$^1$H-NMR (DMSO-$d_6$) δ.

4-(1-{[1-(3-Carboxy-[1,2,4]oxadiazol-5-yl)-2-(2-naphthyl)ethyl]-N-methylcarbamoyl}-2-(2-naphthyl)-ethylcarbamoyl)piperidine-1-carboxylic acid tert-butylester (0.41 g, 0.58 mmol) was dissolved in a mixture trifluoroacetic acid and dichloromethane (1:1, 12 ml). After 10 min at 20° C. the reaction mixture was concentrated in vacuo to give 0.4 g of the title compound as a crude product.

PDMS: (teor. MH$^+$=606.7; found MH$^+$=605.9)

Example 20

Piperidine-4-carboxylic acid (1-{N-[1-(3-methylcarbamoyl-[1,2,4]oxadiazol-5-yl)-2-(2-naphthyl)ethyl]-N-methylcarbamoyl}-2-(2-naphthyl)ethyl)amide

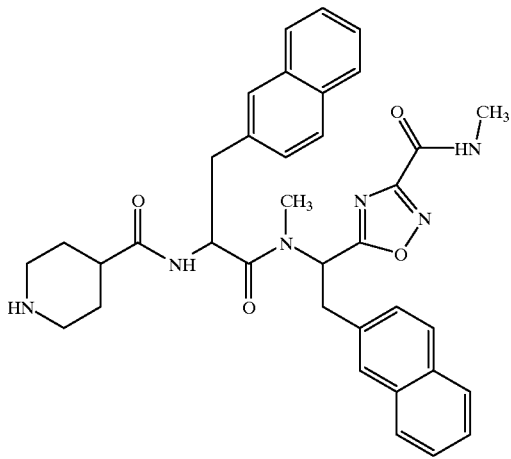

Prepared according to method E.

4-(1-{N-[1-(3-Methylcarbamoyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tertbutylester

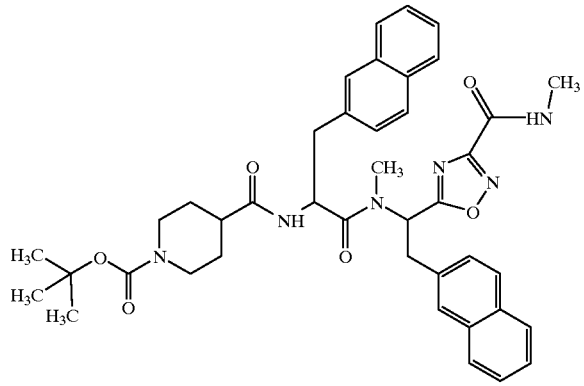

4-((1R)-1-{N-[(1R)-1-(3-Propoxycarbonyl-[1,2,4]oxadiazol-5-yl)-2-(2-naphthyl)ethyl]-N-methylcarbamoyl}-2-(2-naphthyl)ethylcarbamoyl)piperidine-1-carboxylic acid tert-butyl ester (0.80 g, 1.07 mmol) was dissolved in 33% methylamine in ethanol and stirred at 90° C. for 18 h in a closed reaction vessel. The reaction mixture was concentrated in vacuo and the residue was chromatographed on silica (60 g) using ethyl acetate and heptane (7:3) as eluent to give 0.15 g of 4-(1-{-N-[1-(3-methylcarbamoyl-[1,2,4]oxadiazol-5-yl)-2-(2-naphthyl)-ethyl]-N-methylcarbamoyl}-2-(2-naphthyl)ethylcarbamoyl)piperidine-1-carboxylic acid tert butyl ester.

HPLC: R$_t$=31.5 min (Method a)

4-(1-{N-[1-(3-Methylcarbamoyl-[1,2,4]oxadiazol-5-yl)-2-(2-naphthyl)-ethyl]-N-methylcarbamoyl}-2-(2-naphthyl)ethylcarbamoyl)piperidine-1-carboxylic acid tert butyl ester (0.15 g, 0.21 mmol) was dissolved in a mixture of trifluoroacetic acid and dichloromethane (1:1, 4 ml). After 5 min at 20° C. the reaction mixture was concentrated in vacuo. The compound was purified by flash chromatography with silica gel (40 g) using a mixture of dichloromethane and 10% ammonia in ethanol (9:1) as eluent to give 0.08 g of the title compound.

HPLC: R$_t$=20.9 min (Method a)

Example 21

(2E)-5-Amino-5-methylhex-2-enoic acid {1-[N-(1-(3-benzylcarbamoyl-[1,2,4]oxadiazol-5-yl)-2-phenylethyl)-N-methyl-carbamoyl]-2-(2-naphthyl)ethyl}amide

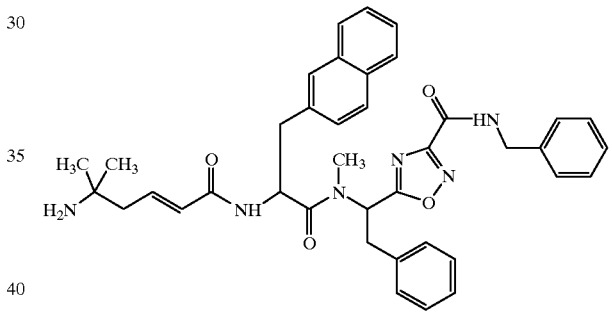

(R) 5-(1-Methylamino-2-phenylethyl)-[1,2,4]oxadiazole-3-carboxylic acid benzylamide

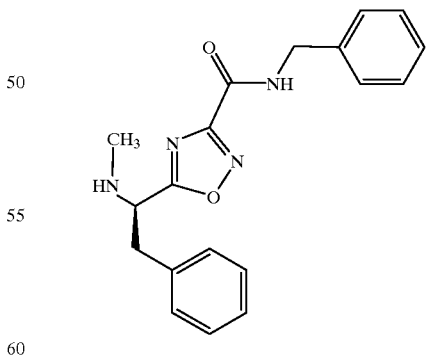

(R) 5-(1-Methylamino-2-phenylethyl)-[1,2,4]oxadiazole-3-carboxylic acid ethylester (3.3 g, 9.0 mmol) was dissolved in ethanol (30 ml). Benzylamine (3 ml) was added and the reaction mixture was stirred for 18 h at 20° C. The reaction mixture was concentrated in vacuo and the residue was crystallised from ethanol to give 2.07 g of (R) 5-(1-methylamino-2-phenylethyl)-[1,2,4]oxadiazole-3-carboxylic acid benzylamide.

m.p. 128–128.5° C.

$^1$H-NMR (DMSO-$d_6$) δ2.22 (s, 3H); 3.08 (dd, 1H); 3.18 (dd, 1H); 4.26 (t, 1H); 4.45 (d, 2H); 7.10–7.45 (m, 1H); 9.50 (t, 1H).

HPLC: $R_t$=17.3 min (Method a)

Calculated for $C_{19}H_{20}N_4O_2$,0.25 EtOH:
C, 67.32; H, 6.23; N, 16.10%; found:
C, 67.35; H, 6.03; N, 16.25%.

{(1R)-1-{N-Methyl-N-[(1R)-1-(3-benzylcarbamoyl-[1,2,4]oxadiazol-5-yl)-2-phenylethyl]carbamoyl}-2-(2-naphthyl)ethyl}carbamic acid tert-butyl ester

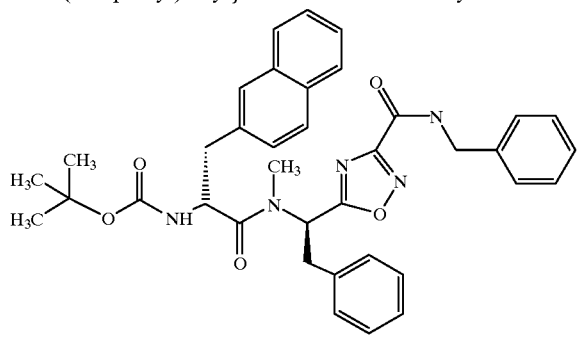

N-(3-Dimethylaminopropyl)-N'-ethylcarbodiimide hydrochloride (1.64 g, 8.57 mmol) and 1-hydroxy-7-azabenzotriazole (1.17 g, 8.57 mmol) were added to a solution of (R) N-tert-butoxycarbonyl-3-(2-naphthyl)alanine (2.70 g, 8.57 mmol) in N,N-dimethylformamide (40 ml). After 20 min at 20° C. a solution of (R) 5-(1-methylamino-2-phenylethyl)-[1,2,4]oxadiazole-3-carboxylic acid benzylamide (2.06 g, 6.12 mmol) in dimethylformamide (40 ml) was added. After 18 h at 20° C. the reaction mixture was poured on water (250 ml) and extracted several times with ethyl acetate (total 200 ml). The collected organic phases were washed with aqueous citric acid (10%, 50 ml), a saturated solution of sodium hydrogencarbonate (3×50 ml) and water (3×50 ml). After drying (magnesium sulfate) the solution was concentrated in vacuo and the residue was chromatographed on silica (150 g) using ethyl acetate and heptane (1:1) as eluent to give 3.9 of {(1R)-1-{N-methyl-N-[(1R)-1-(3-benzylcarbamoyl-[1,2,4]oxadiazol-5-yl)-2-phenylethyl]carbamoyl}-2-(2-naphthyl)ethyl}carbamic acid tertbutyl ester.

2-Amino-N-methyl-N-[1-(3-benzylcarbamoyl-[1,2,4]oxadiazol-5-yl)-2-phenylethyl]-3-(2-naphthyl)propionamide, trifluoro acetic acid

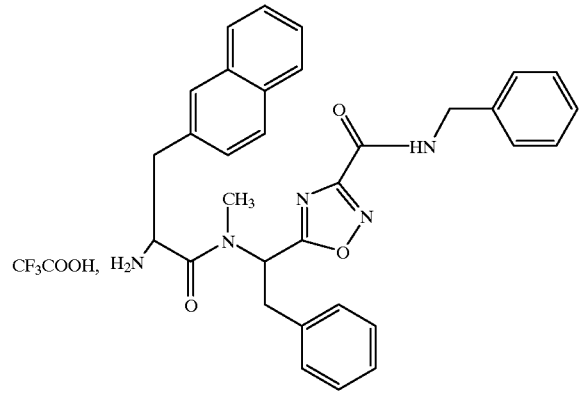

{(1R)-1-{N-methyl-N-[(1R)-1-(3-benzylcarbamoyl-[1,2,4]oxadiazol-5-yl)-2-phenylethyl]carbamoyl}-2-(2-naphthyl)ethyl}carbamic acid tert-butylester (3.9 g, 6.15 mmol) was dissolved in a mixture of trifluoroacetic acid (40 ml) and dichloromethane (40 ml) at 20° C. After 10 min the reaction mixture was concentrated in vacuo and coevaporated from heptane and then from dichloromethane to give 4 g of two isomers of crude 2-amino-N-methyl-N-[1-(3-benzylcarbamoyl-[1,2,4]oxadiazol-5-yl)-2-phenylethyl]-3-(2-naphthyl)propionamide, trifluoro acetic acid that was used for the next step without further purification.

$^1$H-NMR (DMSO-$d_6$) δ2.88 (s); 3.21 (s); 3.32 (m); 3.55 (m); 4.52 (m); 5.95 (m); 6.21 (m).

HPLC:
isomer I: $R_t$=24.2 min (Method a)
isomer II: $R_t$=25.4 min (Method a)

[(2E)-1,1-Dimethyl-4-(1-{N-methyl-N-[1-(3-benzylcarbamoyl-[1,2,4]oxadiazol-5-yl)-2-phenylethyl]carbamoyl}-2-(2-naphthyl)ethylcarbamoyl)but-3-enyl]carbamic acid tert-butylester

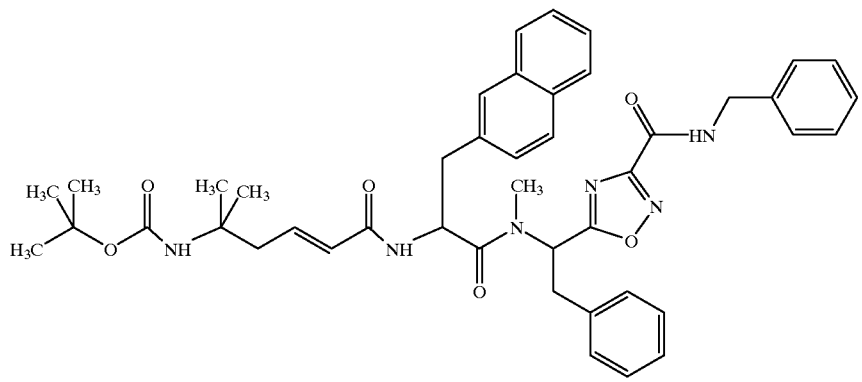

N-(3-Dimethylaminopropyl)-N'-ethylcarbodiimide hydrochloride (0.40 g, 2.1 mmol) and 1-hydroxybenzotriazole monohydrate (0.32 g, 2.1 mmol) were added to a solution of (2E)-5-(tert-butoxycarbonylamino)-5-methylhex-2-enoic acid (0.51 g, 2.1 mmol) in N,N-dimethylformamide (5 ml). After 30 min at 20° C. a mixture of 2-amino-N-methyl-N-[1-(3-benzylcarbamoyl-[1,2,4]oxadiazol-5-yl)-2-phenylethyl]-3-(2-naphthyl)propionamide, trifluoroacetic acid (1.0 g, 1.5 mmol) and triethylamine (0.15 g, 1.5 mmol) in N,N-dimethylformamide (12 ml) were added. After 18 h at 20° C. the reaction mixture was poured on water (100 ml) and extracted several times with ethyl acetate (total 65 ml). The organic phases were collected and washed with aqueous citric acid (10%, 20 ml), a saturated solution of sodium hydrogencarbonate (20 ml) and water (3×20 ml). After drying (magnesium sulfate) the solution was concentrated in vacuo and the residue was chromatographed on silica (85 g) using ethyl acetate and heptane (1:1) as eluent to give 0.77 g of two isomers of [(2E)-1,1-dimethyl-4-(1-{N-methyl-[1-(3-benzylcarbamoyl-[1,2,4]oxadiazol-5-yl)-2-phenylethyl]carbamoyl}-2-(2-naphthyl)ethylcarbamoyl)but-3-enyl]carbamic acid tert-butylester.

HPLC:

Isomer I: $R_t$=34.1 min (Method a)

Isomer II: $R_t$=34.4 min (Method a)

[(2E)-1,1-Dimethyl-4-(1-{N-methyl-N-[1-(3-benzylcarbamoyl-[1,2,4]oxadiazol-5-yl)-2-phenylethyl]carbamoyl}-2-(2-naphthyl)ethylcarbamoyl)but-3-enyl]carbamic acid tert-butylester (0.77 g, 1.0 mmol) was dissolved in a mixture trifluoroacetic acid (2 ml) and dichloromethane (2 ml). After 10 min at 20° C. the reaction mixture was diluted with dichloromethane (25 ml) and neutralised with a saturated aqueous solution of sodium hydrogencarbonate. The organic phase was dried (magnesium sulfate) and concentrated in vacuo to give 0.7 g of two isomers of the title compound.

HPLC:

Isomer I: $R_t$=24.5 min (Method a)

Isomer II: $R_t$=25.3 min (Method a)

Example 22

(2E)-5-Amino-5-methylhex-2-enoic acid N-{(1R)-1-[N-((1R)-1-benzyl-2,5-dihydroxypentyl)-N-methylcarbamoyl]-2-(2-naphthyl)ethyl}-N-methylamide

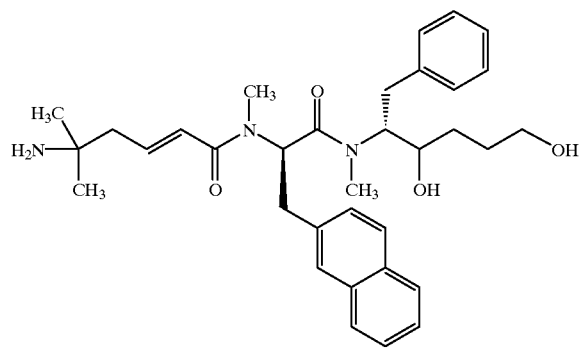

Prepared according to method J.

N-((1R)-1-Formyl-2-phenylethyl)-N-methylcarbamic acid tert-butyl ester

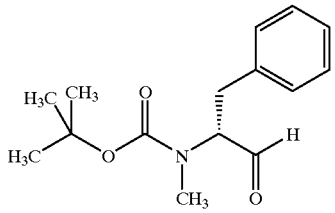

Oxalyl chloride (4.24 mL, 48.61 mmol) was dissolved in dichloromethane (30 mL). The solution was cooled to −63° C. A solution of DMSO (4.6 mL, 64.81 mmol) in dichloromethane (20 mL) was added dropwise. The solution was stirred for 5 min and a solution of N-((1R)-1-(hydroxymethyl)-2-phenylethyl)-N-methylcarbamic acid tert-butylester (8.6 g, 32.41 mmol) in dichloromethane (200 mL) was added dropwise over a period of 30 min. The reaction mixture was stirred for 20 min at −63° C. A solution of triethylamine (18.07 mL, 129.62 mmol) in dichloromethane (40 mL) was added over a period of 25 min. The solution was warmed to −35° C. and immediately cooled to −63° C. It was stirred at this temp. for 1 h. Acetic acid (8.15 mL, 142.58 mmol) was added. The reaction mixture was warmed to 10° C. and washed with water (2×200 mL) and satd. sodium hydrogencarbonate solution (150 mL). The org. phase was dried over magnesium sulfate. The solvent was removed in vacuo to give 7.536 of N-((1R)-1-formyl-2-phenylethyl)-N-methylcarbamic acid tert-butylester $^1$H-NMR (CDCl$_3$): δ=1.40 and 1.44 (both s, together 9H); 2.52 and 2.58 (both s, together 3H); 2.90 and 3.00 (both dd, together 1H); 3.81 (dd, 1H); 4.00 and 4.20 (both dd, together 1H); 7.10–7.35 (m, 5H).

N-((1R)-1-Benzyl-2-hydroxypent-4-enyl)-N-methylcarbamic acid tert-butylester

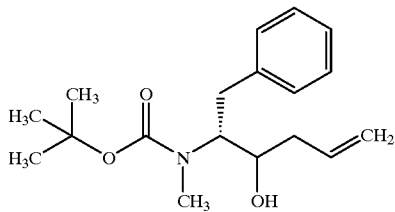

N-((1R)-1-Formyl-2-phenylethyl)-N-methylcarbamic acid tert-butylester (6.0 g, 20.0 mmol) was dissolved in ether (150 mL). The solution was cooled to −78° C. and allylmagnesium bromide (22 mL of a 1.0 M solution in ether, 22 mmol) was added dropwise. After addition, the solution was warmed to room temp. It was given onto 10% ammonium chloride solution in water (200 mL). The phases were separated. The aqueous phase was extracted with ethyl acetate (3×50 mL). The organic layers were combined and washed with satd. sodium hydrogencarbonate solution (100 mL) and dried over magnesium sulfate. The solvent was removed in vacuo. The crude product was purified by flash chromatography on silica (260 g) with ethyl acetate/heptane 1:1 to give 4.00 g of N-((1R)-1-benzyl-2-hydroxypent-4-enyl)-N-methylcarbamic acid tert-butylester.

$^1$H-NMR (CDCl$_3$): δ=1.10–1.50 (m, 9H); 1.90–3.40 (m, 8H); 3.50–4.10 (m, 2H); 5.00–5.30 (m, 2H); 5.90 (m, 1H); 7.10–7.40 (m, 5H).

((1R)-1-Benzyl-2,5-dihydroxypentyl)methyl carbamic acid tert-butylester

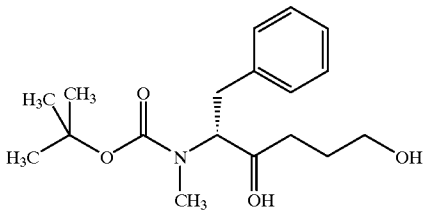

N-((1R)-1-Benzyl-2-hydroxypent-4-enyl)-N-methylcarbamic acid tert-butylester (3.95 g, 11.60 mmol) was dissolvend in THF (90 mL) and added to a solution of 9-borabicyclo[3.3.1]nonane (46.64 mL of a 0.5M solution in THF, 23.32 mmol)in THF (90 mL). The solution was heated to reflux for 16 h. The mixture was cooled to room temp. Ethanol (22 mL) was added dropwise. 6N Sodium hydroxide solution in water (6.6 mL, 39,44 mmol) and subsequently hydrogen peroxide (35% solution in water) were added slowly. The reaction mixture was heated to reflux for 1 h and cooled to room temp. It was given onto 1N sodium hydroxide solution (200 mL). The phases were separated. The aqueous phase was extracted with ethyl acetate (3×50 mL). The combined organic layers were washed with a 37% solution of sodium hydrogensulfite (150 mL). The solution was dried over magnesium sulfate. It was washed with a 37% solution of sodium hydrogensulfite (200 mL) and dried over magnesium sulfate. The solvent was removed in vacuo. The residue was dissolved in ethyl acetate (200 mL), washed with 37% solution of sodium hydrogensulfite (200 mL) and dried over magnesium sulfate. The crude product was chromatographed on silica (180 g) with ethyl acetate and subsequently on silica (100 g) with dichloromethane/methanol/25% aqueous ammonia 100:10:1 to give 586 mg of ((1R)-1-benzyl-2,5-dihydroxypentyl)methylcarbamic acid tert-butylester

MS (EI): 365 (20%; [M+1]$^+$)

$^1$H-NMR (CDCl$_3$): δ=1.22 and 1.40 (both s, together 9H); 1.60–1.90 (m, 5H); 2.50, 2.60, and 2.73 (all s, together 3H);2.80–4.00 (m, 7H); 7.10–7.35 (m, 5H).

(5R)-4-Hydroxy-5-(methylamino)-6-phenylhexyl acetate

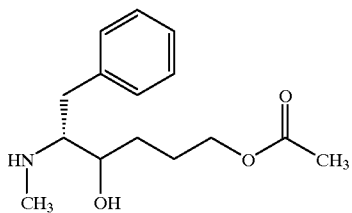

((1R)-1-Benzyl-2,5-dihydroxypentyl)methylcarbamic acid tert-butylester (560 mg, 1.52 mmol) was dissolved in ethyl acetate (10 mL). 3M Hydrogen chloride in ethyl acetate (2.0 mL, 6.08 mmol) was added. The solution was stirred at room temp. for 1 h. It was diluted with ethyl acetate (10 mL) and extracted with 1N sodium hydroxide solution (30 mL). The aqueous phase was extracted with ethyl acetate (3×10 mL). The combined organic phases were dried over magnesium sulfate. The solvent was removed in vacuo. The residue was dissolved in dichloromethane (5 mL). The solution was cooled to 0° C. Trifluoroacetic acid (5 mL) was added. The solution was stirred at this temp. for 5 min. The solvents were removed in vacuo. The residue was dissolved in ethyl acetate (10 mL). The solution was extracted with iN sodium hydroxide solution (10 mL). The aqueous phase was extracted with ethyl acetate (2×5 mL). The combined organic layers were dried over magnesium sulfate. The solvent was removed in vacuo. The crude product was purified by flash chromatography on silica (40 g) with dichloromethane/methanol/25% aqueous ammonia 100:10:1 to give 136 mg of (5R)-4-hydroxy-5-(methylamino)-6-phenylhexyl acetate.

$^1$H-NMR (CDCl$_3$): δ=1.50–2.05 (m, 4H); 2.07 (s, 3H); 2.30 (s, 3H); 2.55 (dd, 1H); 2.65 (td, 1H); 2.82 (dd, 1H); 3.75 (td, 1H); 4.15 (m, 2H); 7.15–7.35 (m, 5H).

HPLC (method B): 17.87 min (85%)

(5R)-5-({(2R)-2-[((2E)-5-Amino-5-methylhex-2-enoyl)methylamino]-3-(2-naphthyl)propionyl}methylamino)-4-hydroxy-6-phenylhexyl acetate

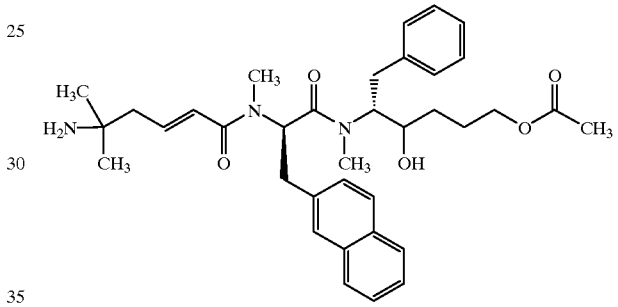

(5R)-4-Hydroxy-5-(methylamino)-6-phenylhexyl acetate (126 mg, 0.475 mmol), (2R)-2-(tert-butoxycarbonylmethylamino)-3-(2-naphthyl)propionic acid (313 mg, 0.95 mmol and 1-hydroxy-7-azabenzotriazole (65 mg, 0.475 mmol) was dissolved in dichloromethane/dimethylformamide 2:1 (9 ml) at 0° C. N-ethyl-N'-(3-dimethylaminopropyl)carbodiimide hydrochloride (91 mg, 0.475 mmol) was added and the the mixture stirred at 0° C. for h and then at room temp. for 48 h. The dichloromethane was evaporated from the mixture using a stream of nitrogen and ethyl acetate (50 ml) was added. The resulting solution was extracted sequentially with 5% aqueous sodium hydrogencarbonate (50 ml), water (50 ml), 5% aqueous potassium hydrogen sulphate (50 ml) and water (50 ml). The resulting organic phase was dried with sodium sulfate and concentrated in vacuum on a rotary evaporator to dryness. This dry material was dissolved in dichloromethane (2 ml) and trifluoroacetic acid (2 ml) and allowed to react for 10 min and then concentrated to an oil using a stream of nitrogen and the resulting oil was dissolved in 70% acetonitrile (1 ml). 1 N hydrochloric acid (3 ml) and water (47 ml) were added and the resulting mixture was immediately frozen and lyophilized. This lyophilized product was dissolved in dichloromethane/dimethylformamide 2:1 (9 ml) and (2E)-5-tert-butyloxycarbonylamino-5-methylhex-2-enoic acid (231 mg, 0.95 mmol) and 1-hydroxy-7-azabenzotriazole (129 mg, 0.95 mmol) was added. The mixture was cooled to 0° C., N-ethyl-N'-(3-dimethylaminopropyl)-carbodiimide hydrochloride (91 mg) and diisopropylethylamine (81 μl, 0.475 mmol) was added and the mixture was stirred for 1 h at 0° C. and for 18 h at room temp. The dichloromethane was evaporated from the mixture using a stream of nitrogen and ethyl acetate (50 ml) was added. The resulting solution was extracted sequentially with 5% aqueous sodium hydrogencarbonate (50 ml), water (50 ml), 5% aqueous potassium hydrogen sulfate (50 ml) and water (50 ml). The resulting organic phase was dried with sodium sulfate and concentrated in vacuum on a rotary evaporator to dryness. The dry material was dissolved in dichloromethane (2 ml) and trifluoroacetic acid (2 ml) and allowed to react for 10 min and then concentrated to an oil using a stream of nitrogen. The resulting oil was dissolved in 70% acetonitrile (5 ml) and water (45 ml).

15 ml Of the solution of crude (5R)-5-({(2R)-2-[((2E)-5-amino-5-methyhex-2-enoyl)methylamino]-3-(2-naphthyl)propionyl}methylamino)-4-hydroxy-6-phenylhexyl acetate was cooled to 0° C. and 1M sodium hydroxide (15 ml) was added dropwise under stirring. After stirring 10 min at 0° C. acetic acid (2 ml) and water (50 ml) were added. The product was isolated from this solution by semipreparative HPLC in three runs on a 25 mm×250 mm column packed with 7μ C-18 silica which was preequilibrated with 28% acetonitrile in 0.05M ammonium sulfate, which was adjusted to pH 2.5 with 4M sulfuric acid.

The column was eluted with a gradient of 28%–38% acetonitrile in 0.05M ammonium sulfate, pH 2.5 at 10 ml/min during 47 min at 40° C. and the peptide containing fractions were collected, diluted with 3 volumes of water and applied to a Sep-Pak® C18 cartridge (Waters part. #:51910) which was equilibrated with 0.1% trifluoroacetic acid. The peptide was eluted from the Sep-Pak® cartridge with 70% acetonitrile 0.1% trifluoroacetic acid and isolated from the eluate by lyophilisation after dilution with water.

The final product obtained was characterised by analytical RP-HPLC (retention time) and by Plasma desorption mass spectrometry (molecular mass). Mass spectrometry which was performed using a Bio-Ion 20 time-of-flight instrument (Bio-Ion Nordic AB, Uppsala Sweden). The result agreed with the expected structure (M+H found=560.2,M+H theory=560.8).

The RP-HPLC analysis was performed using UV detection at 214 nm and a Vydac 218TP54 4.6 mm×250 mm 5μ C-18 silica column (The Separations Group, Hesperia) which was eluted at 1 ml/min at 42° C. Two different elution conditions were used:

A1: The column was equilibrated with 5% acetonitrile in a buffer consisting of 0.1M ammonium sulfate, which was adjusted to pH 2.5 with 4M sulfuric acid and eluted by a gradient of 5% to 60% acetonitrile in the same buffer during 50 min.

B1: The column was equilibrated with 5% acetonitrile/0.1% trifluoroacetic acid/water and eluted by a gradient of 5% acetonitrile/0.1% trifluoroacetic acid/water to 60% acetonitrile/0.1% trifluoroacetic acid/water during 50 min.

The retention time using elution conditions A1 and B1 was found to be 30.08 min and 31.78 min, respectively.

Example 23

3-Aminomethyl-N-((1R)-1-{N-[(1R)-1-(2-hydroxyethoxymethyl)-2-phenylethyl]-N-methylcarbamoyl}-2-(2-naphthyl)ethyl)-N-methylbenzamide

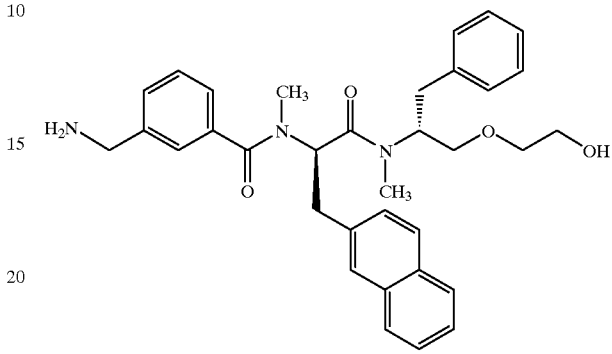

Prepared according to method K

N-((1R)-1-(2-Hydroxyethoxymethyl)-2-phenylethyl)-N-methylcarbamic acid tert-butylester

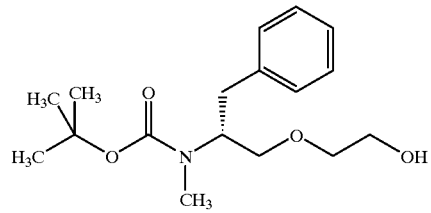

((2R)-2-(tert-Butoxycarbonylmethylamino)-3-phenylpropoxy)acetic acid ethyl ester (0.50 g, 1.42 mmol) was dissolved in THF (4 mL). Lithium boronhydride (1.56 mL of a 2.0 M solution in THF, 3.13 mmol) was added dropwise. Ethanol (8 mL) was added. The reaction mixture was stirred 16 h at room temp. The solution was acidified with 10% citric acid to pH=4. The solvent was removed in vacuo. The residue was dissolved in water (50 mL). This solution was extracted with dichloromethane (3×40 mL). The combined organic layers were dried over magnesium sulfate. The solvent was removed in vacuo. The crude product was purified by flash chromatography on silica (30 g) with dichloromethane/ethyl acetate 1:1 as eluent to give 0.29 g of N-((1R)-1-(2-hydroxyethoxymethyl)-2-phenylethyl)-N-methylcarbamic acid tert-butylester $^1$H-NMR (CDCl$_3$): δ=1.32 and 1.41 (both s, together 9H); 2.50–2.85 (m, 5H); 3.40–3.80 (m, 6H); 4.40 and 4.60 (both br, together 1H); 7.10–7.35 (m, 5H).

2-((2R)-2-Methylamino-3-phenylpropoxy)ethanol

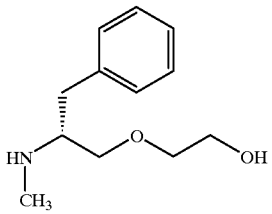

N-((1R)-1-(2-Hydroxyethoxymethyl)-2-phenylethyl)-N-methylcarbamic acid tert-butylester (0.29 g, 0.90 mmol) was dissolved in dichloromethane (3 mL). Trifluoroacetic acid (1 mL) was added. The solution was stirred at 0° C. for 15 min. The solvents were removed in vacuo. The residue was dissolved in dichloromethane (10 mL) and extracted with 1N sodium hydroxide (10 mL). The organic phase was dried over magnesium sulfate. The solvent was removed in vacuo to give 0.11 g of crude 2-((2R)-2-methylamino-3-phenylpropoxy)ethanol, which was used for further syntheses.

HPLC (method b): 9.10 min.

$^1$H-NMR (CDCl$_3$): δ=2.48 (s, 3H); 2.75 (dd, 1H); 2.80–3.00 (m, 2H); 3.40 (dd, 1H); 3.45–3.65 (m, 3H); 3.65–3.80 (m, 2H); 7.15–7.35 (m, 5H).

2-( (2R)-2-Methylamino-3-phenylpropoxy)ethanol (91 mg, 0.435 mmol), (2R)-2-(tert-butoxycarbonylmethylamino)-3-(2-naphthyl)propionic acid (215 mg, 0.653 mmol) and 1-hydroxy-7-azabenzotriazole (HOAT) (89 mg, 0.653 mmol) was dissolved in dichloromethane (10 ml) and N,N-Dimethylfermamide (5 ml). After cooling to 0° C. N-(3-dimethylaminopropyl)-N'-ethylcarbodiimide hydrochloride (125 mg, 0.653 mmol) was added and after stirring 30 min at 0° C. diisopropylethylamine (75 μl, 0.435 mmol) was added. After stirring at room temp. the dichloromethane was removed by a stream of nitrogen and ethyl acetate (25 ml) was added. The mixture was extracted with 5% sodium hydrogencarbonate (2×25 ml), 5% potassium hydrogensulfate and water (25 ml). The organic phase was dried over sodium sulfate andd concentrated in vacuum to give N-((1R)-1-(N-((1R)-1-(2-hydroxyethoxymethyl)-2-phenylethyl)-N-methylcarbamoyl)-2-(2-naphthyl)ethyl)-N-methylcarbamic acid tert-butylester as a dry residue (240 mg). Half of this N-((1R)-1-(N-((1R)-1-(2-hydroxyethoxymethyl)-2-phenylethyl)-N-methylcarbamoyl)-2-(2-naphthyl)ethyl)-N-methylcarbamic acid tert-butylester (120 mg, 0.230 mmol) was dissolved in dichloromethane (1 ml) and trifluoroacetic acid (1 ml) and allowed to react for 10 min and then concentrated to an oil using a stream of nitrogen and the resulting oil was dissolved in 70% acetonitrile (1 ml). 1 N hydrochloric acid (1 ml) and water (50 ml) was added and the resulting mixture was immediately frozen and lyophilized.

This lyophilized product was dissolved in dichloromethane (5 ml) and a solution of 3-(tert-butoxycarbonylaminomethyl)benzoic acid (503 mg, 2.0 mmol) and N-ethyl-N'-(3-dimethylaminopropyl)-carbodiimide hydrochloride (192 mg, 1 mmol) in dichloromethane (5 ml) which had been allowed to react at 0° C. for 15 min was added. Finally diisopropylethylamine (171 μl, 1.0 mmol) was added and the mixture was stirred for 72 h at room temp. The dichloromethane was evaporated from the mixture using a stream of nitrogen and ethyl acetate (25 ml) was added. The resulting solution was extracted sequentially with 5% aqueous sodium hydrogencarbonate (2×25 ml), water (25 ml), 5% aqueous potassium hydrogensulfate (25 ml) and water (25 ml). The resulting organic phase was dried with sodium sulfate and concentrated in vacuum on a rotary evaporator to dryness. The dry material was dissolved in dichloromethane (2 ml) and trifluoroacetic acid (2 ml) and allowed to react for 10 min and then concentrated to an oil using a stream of nitrogen. The resulting oil was dissolved in 70% acetonitrile (5 ml) and water (400 ml).

Analytical HPLC using conditions A1 (described below) showed the prescence of two major peaks with the retention times 28.82 min and 35.67 min a minor peak at 29.98 min. Plasma desorption mass spectrometry of collected fractions. Mass spectrometry which was performed using a Bio-Ion 20 time-of-flight instrument (Bio-lon Nordic AB, Uppsala Sweden), indicated that the minor product was the desired product. The result agreed with the expected structure (M+H found=553.0, M+H theory=554.7). The other two product resulted from acylations during synthesis of the hydroxy group left unprotected.

All three compounds were isolated by semipreparative HPLC in four runs on a 25 mm×250 mm column packed with 7μ C-18 silica which was preequilibrated with 37% acetonitrile in 0.05M ammonium sulphate, which was adjusted to pH 2.5 with 4M sulphuric acid. The column was eluted with a gradient of 37%–44% acetonitrile in 0.05M ammonium sulfate, pH 2.5 at 10 ml/min during 47 min at 40° C. and each of the product containing fractions were collected, diluted with 3 volumes of water and applied to Sep-Pak® C18 cartridges (Waters part. #:51910 ) which were equilibrated with 0.1% trifluoroacetic acid. The products were eluted from the Sep-Pak® cartridges with 70% acetonitrile 0.1% trifluoroacetic acid and isolated from the eluate by lyophilisation after dilution with water.

The compounds corresponding to the two major peaks were saponified to reverse the undesired acylations in order to increase the yield of the target compound. The compounds were dissolved in 1.5 ml 0.066 N sodium hydroxide for 15 min followed by neutralisation with 1 ml 1N hydrochloric acid. Then the target compound was isolated by semi-preparative HPLC using a procedure similar to the one described above.

The final product obtained was characterised by analytical RP-HPLC (retention time). The RP-HPLC analysis was performed using UV detection at 214 nm and a Vydac 218TP54 4.6 mm×250 mm 5μ C-18 silica column (The Separations Group, Hesperia) which was eluted at 1 ml/min at 42° C. Two different elution conditions were used:

A1: The column was equilibrated with 5% acetonitrile in a buffer consisting of 0.1M ammonium sulfate; which was adjusted to pH 2.5 with 4M sulfuric acid and eluted by a gradient of 5% to 60% acetonitrile in the same buffer during 50 min.

B1: The column was equilibrated with 5% acetonitrile/ 0.1% trifluoroacetic acid/water and eluted by a gradient of 5% acetonitrile/0.1% trifluoroacetic acid/water to 60% acetonitrile/0.1% trifluoroacetic acid/water during 50 min.

The retention time using elution conditions A1 and B1 was found to be 29.87 min and 34.28 min, respectively.

Example 24

Piperidine-4-carboxylic acid ((1R,2E)-4-hydroxymethyl-5-(2-naphthyl)-1-((2-naphthyl)methyl)pent-2-enyl)amide

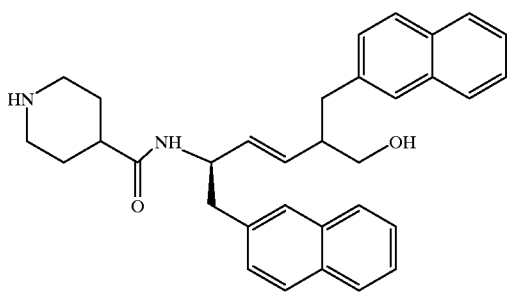

((1R)-4-(tert-Butyldimethylsilanyloxymethyl)-1-((2-naphthyl)methyl)-5-(2-naphthyl)pent-2-enyl)carbamic acid tert-butylester

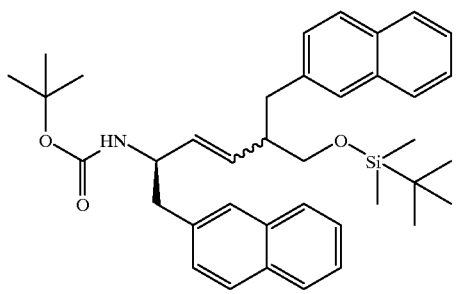

This compound was prepared as in example 9. ((1R)-1-benzenesulfonylmethyl-2-(2-naphthyl)ethyl)carbamic acid tert-butylester (3.71 g; 8.74 mmol) and 2-(tert-butyldimethylsilanyloxymethyl)-3-(2-naphthyl)propionaldehyde (4.3 g; 13.11 mmol) were used as starting materials. Chromatography was carried out using diethylether/heptane 1:3 as eluent on silica (5×25 cm) to afford 2.20 g of ((1R)-4-(tert-butyldimethylsilanyloxymethyl)-1-((2-naphthyl)methyl)-5-(2-naphthyl)pent-2-enyl)carbamic acid tert-butyl ester as a mixture of isomers.

$^1$H-NMR (CDCl$_3$) (selected peaks) δ0.0–0.05 (four s, 6H), 0.85–0.95 (four s, 9H), 1.30–1.40 (three s, 9H), 5.2–5.5 (m, 2H)

(3E,5R)5-Amino-6-(2-naphthyl)-2-((2-naphthyl)methyl)hex-3-en-1-ol

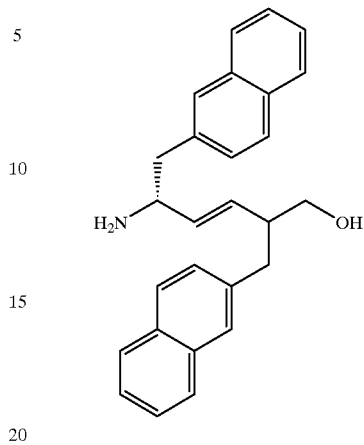

((1R)-4-(tert-Butyldimethylsilanyloxymethyl)-1-((2-naphthyl)methyl)-5-(2-naphthyl)pent-2-enyl)carbamic acid tert-butylester (2.20 g; 3.60 mmol) was dissolved in a mixture of acetonitrile (100 ml) and an aqueous solution of hydrogen fluoride (48%, 4.5 ml). After stirring for 3 h a mixture of ethyl acetate (200 ml) and aqueous sodium carbonate (10%, 200 ml) was added. The phases were separated and the organic phase was dried (Magnesium sulfate) and evaporated in vacuo. The residue was chromatographed on silica (4×38 cm) using a mixture of ethyl acetate (85%), ethanol (14%) and conc. aqueous ammonia (1%) as eluent. Two close spots were separated this way. The one that eluted first was clean on HPLC whereas the following contained several isomers. The first fraction had E-geometry and 220 mg of (3E,5R)-5-amino-6-((2-naphthyl)-2-(2-naphthyl)methyl)hex-3-en-1-ol were taken to the next step.

$^1$H-NMR (CDCl$_3$) δ1.45 (s(br), 3H); 2.55–2.92 (m, 5H); 3.35–3.68 (m, 3H); 5.37 (dd, part of ABX-syst., J$_1$=15 Hz, J$_2$=7 Hz, 1H), 5.52 (dd, part of ABX-syst., J$_1$=15 Hz, J$_2$=5 Hz, 1H), 7.15–7.84 (m, 14 H).

(N-tert-Butyloxycarbonyl-piperidine-4-carboxylic acid ((1R,2E) (4-hy-droxymethyl)-5-(2-naphthyl)-1-((2naphthyl)methyl)pent-2-enyl)amide

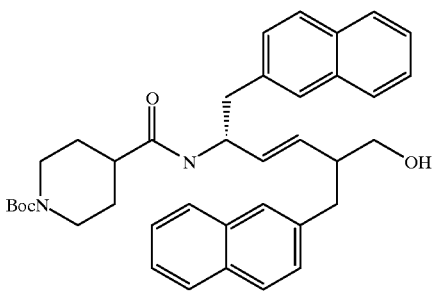

N-tert-Butyloxycarbonylpiperidine-4-carboxylic acid (378 mg; 0.991 mmol) and EDAC (198 mg; 1.038 mmol) were dissolved in methylene chloride (15 ml) and stirred for 15 min. (3E,5R)-5-Amino-6-(2-naphthyl)-2-((2-naphthyl)methyl)hex-3-en-1-ol (180 mg; 0.472 mmol) was added and the mixture was stirred for 6 h. The organic phase was washed with sodium hydrogensulfate (10%, 10 ml) and sodium hydrogencarbonate (satd., 15 ml), dried (Magnesium sulfate). The solvent was removed in vacuo and the residue was chromatograped on silica (30×2.5 cm) using ethyl acetate/heptane 1:1 as eluent to afford 220 mg of N-tert-butyloxycarbonylpiperidine-4-carboxylic acid ((1R,2E)-4-(hydroxymethyl)-5-(2(-naphthyl)-1-(2-naphthyl)methyl)-pent-2-enyl)amide $^1$H-NMR (CDCl$_3$): δ: 1.35–1.55 (m, (s at 1.45); 15 H); 1.93–2.01 (m, 1H); 2.55–2.68 (m, 4H); 2.70–2.90 (m, 2H); 3.01 (dd, 1H); 3.38 (dd, 1H); 3.55 (d(br), 1H); 4.67 (p, 1H); 5.18 (d, 1H); 5.31 (dd, 1H), 5.37 (dd, 1H), 7.15–7.79 (m, 14H).

N-tert-Butyloxycarbonylpiperidine-4-carboxylic acid ((1R,2E)-4-(hydroxymethyl)-5-(2-naphthyl)-1-((2-naphthyl)methyl)pent-2-enyl)-amide (220 mg; 0.371 mmol) was dissolved in methylene chloride (5 ml) and trifluoroacetic acid (5 ml) and stirred for 90 min. The volatiles were removed in vacuo and methylene chloride (20 ml) was added and removed in vacuo 3 times successively to afford 170 mg of the title compound.

$^1$H-NMR (CDCl$_3$) (selected peaks) δ4.60 (1H); 5.43 (m, 2H); 7.00–7.77 (14 H), 8.7 and 9.05 (s(br), 2H).

ESMS: (M+H)$^+$: 493.2

HPLC (Al): R$_t$=36.15 min.

Example 25

Piperidine-4-carboxylic acid ((1R)-2-(2-naphthyl)-1-((1R)-2-(2-naphthyl)-1-(1-phenethyl-1H-tetrazol-5-yl)ethyl-carbamoyl)ethyl)amide

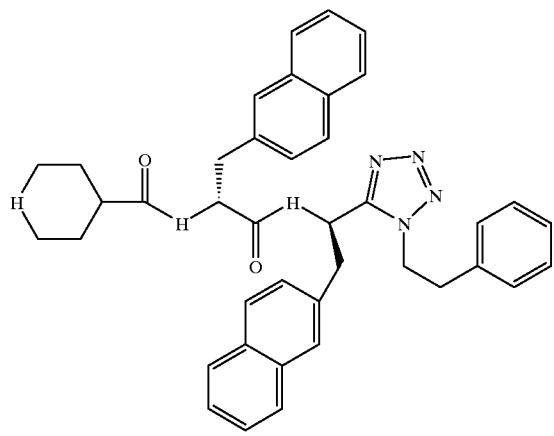

((1R)-2-(2-Naphthyl)-1-(phenethylcarbamoyl)ethyl)carbamic acid tert-butyl ester

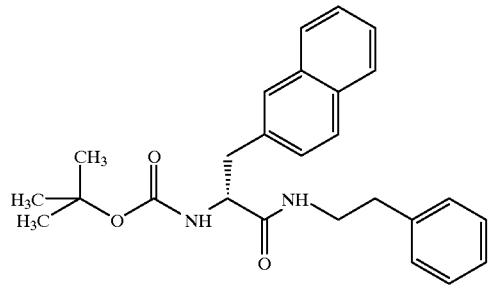

D-tert-Butyloxycarbonyl-(2-naphthyl)alanine (5.0 g, 15.85 mmol) was dissolved in dry methylene chloride (80 ml). HOBT (2.14 g; 15.85 mmol) and EDAC (3.34; 17.43 mmol) were added and the mixture was stirred for 15 min. Phenethylamine (2.0 ml; 15.85 mmol) was added and the mixture was stirred 24 h at room temperature. Methylene chloride (200 ml) was added and the organic phase was washed with water (100 ml), sodium hydrogencarbonate (satd. 100 ml) and dried (Magnesium sulfate). The solvent was removed in vacuo and the residue was chromatographed on silica (3.5×40 cm) using methylene chloride/ethyl acetate (6:1) as eluent to afford 4.9 5 g of ((1R)-2-(2-naphthyl)-1-(phenethylcarbamoyl)ethyl)carbamic acid tert-butyl ester H-NMR (CDCl$_3$): δ: 1.39 (s, 9H); 2.52 (m, 1H); 2.64 (m, 1H); 3.15 (dd, 1H); 3.23 (dd, 1H); 3.36 (m; 1H); 3.45 (m, 1H); 4.31 (dd, 1H); 5.08 (s(br); 1H); 5.62 (s(br); 1H); 6.85–7.82 (12 arom.)

((1R )-2-(2-Naphthyl)-1-(1-phenethyl-1H-tetrazol-5-yl)ethyl)carbamic acid tert-butylester

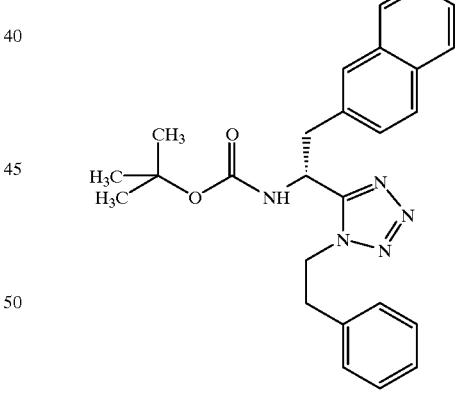

((1R)-2-(2-Naphthyl)-1-(phenethylcarbamoyl)ethyl) carbamic acid tert-butyl ester (2.20 g, 5.26 mmol) was dissolved in dry THF (50 ml). Triphenylphosphine (2.76 g; 10.52 mmol) diethylazodicarboxylate (1.66 g, 10.52 mmol) and trimethylsilyl azide (1.22 g; 10.52 mmol) were added. The mixture was stirred overnight at room temperature. Ammonium ceric nitrate (23.06 g; 21.04 mmol) was dissolved in water (400 ml) and added dropwise to the reation mixture. THF (120 ml) was added and the reaction mixture was extracted with methylene chloride (3×300 ml). The organic phase was dried (magnesium sulfate) and the solvent was removed in vacuo. The residue was chromatographed on silica (5×40 cm) using ethyl acetate/heptane as eluent (1:1) to afford 0.30 g of ((1R)-2-(2-naphthyl)-1-(1-phenethyl-1H-tetrazol-5-yl)ethyl)carbamic acid tert-butylester H-NMR (CDCl₃) δ1.32 (s, 9H); 2.72 (m, 1H); 2.98 (m, 1H); 3.13 (dd; 1H); 3.41 (dd, 1H); 4.42 (t, 2H); 4.99 (dd; 1H); 5.12 (d, 1H); 6.82–7.80 (12 arom.H)

(1R)-2-(2-Naphthyl)-1-(1-phenethyl-1H-tetrazol-5-yl)ethylamine

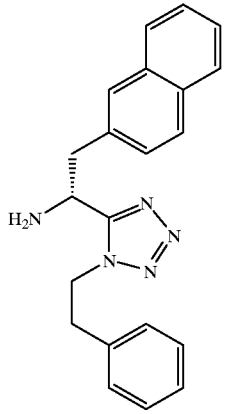

((1R )-2-(2-Naphthyl)-1-(1-phenethyl-1H-tetrazol-5-yl)ethyl)carbamic acid tert-butylester (0.30 g; 0.68 mmol) was dissolved in methylene chloride (20 ml) and trifluoroacetic acid (2 ml) was added. The mixture was stirred for 3 h at RT. The solvent was removed in vacuo and the residue was dissolved in methylene chloride (50 ml) and washed with sodium hydrogencarbonate (10%; 30 ml). The organic phase was dried (Magnesium sulfate) and the solvent removed in vacuo. The residue was chromatographed on silica (2.5×15 cm) using ethyl acetate as eluent to afford 170 mg of (1R)-2-(2-naphthyl)-1-(1-phenethyl-1H-tetrazol-5-yl)ethylamine.

H-NMR (CDCl₃) δ1.75 (s(br); 2H); 3.00 (m 2H); 3.09 (d, 2H); 3.92 (t, 1H); 4.25 (m, 2H); 6.85–7.85 (12 arom.H).

((1R)-2-(2-Naphthyl)-1-((1R)-2-(2-naphthyl)-1-(1-phenethyl-1H-tetrazol-5-yl)ethylcarbamoyl)ethyl) carbamic acid tert-butyl ester

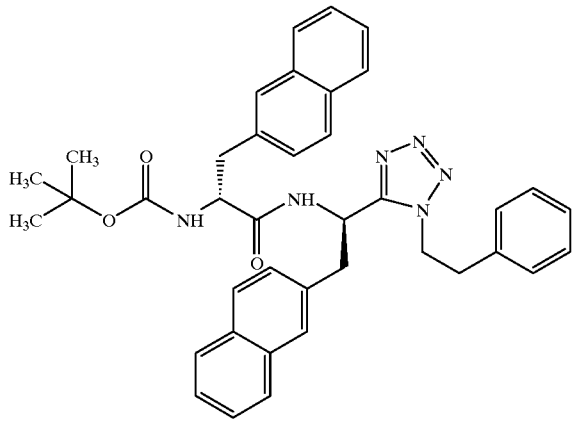

D-tert-Butyloxycarbonyl-(2-Naphthyl)alanine (0.129 g; 0.408 mmol) was dissolved in methylene chloride (10 ml).

HOBT (55 mg; 0.408 mmol) and EDAC (86 mg; 0.449 mmol) were added and the mixture was stirred for 15 min. at RT. (1R)-2-(2-Naphthyl)-1-(1-phenethyl-1H-tetrazol-5-yl)ethylamine (141 mg; 0.408 mmol) was added and the mixture was stirred overnight. Methylene chloride (25 ml) was added and the organic phase was washed with sodium hydrogen carbonate (10%; 25 ml), sodium hydrogen sulfate (10%; 25 ml) and water (25 ml). The organic phase was dried (Magnesium sulfate) and the solvent was removed in vacuo to afford 237 mg of ((1R)-2-(2-naphthyl)-1-((1R)-2-(2-naphthyl)-1-(1-phenethyl-1H-tetrazol-5-yl)ethylcarbamoyl)ethyl)carbamic acid tert-butylester.

H-NMR (CDCl₃) δ1.30 (s, 9H); 2.75 (m, 1H); 2.95 (m, 4H); 3.33 (dd, 1H); 4.15 (m, 2H); 4.30 (m, 1H); 4.65 (d(br), 1H); 5.18 (dd, 1H); 6.60–7.85 (19 arom. H).

(2R)-2-Amino-3-(2-naphthyl)-N-((1R)-2-(2-naphthyl)-1-(1-phenethyl-1H-tetrazol-5-yl)ethyl) propionamide

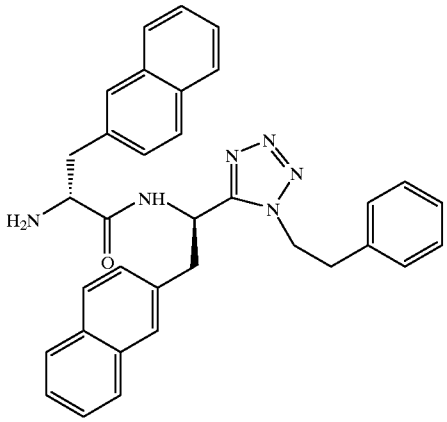

((1R)-2-(2-Naphthyl)-1-((1R)-2-(2-naphthyl)-1-(1-phenethyl-1H-tetrazol-5-yl)ethylcarbamoyl)ethyl)carbamic acid tert-butyl ester (215 mg; 0.34 mmol) was dissolved in a mixture of methylene chloride (4 ml) and trifluoroacetic acid (2 ml) and stirred at room temperature for 30 min. The solvent was removed in vacuo and the residue was dissolved in ethyl acetate and aqueous sodium hydrogencarbonate (10%; 10 ml). The phases were separated, the organic phase was dried (Magnesium sulfate) and the solvent removed in vacuo. The residue was chromatographed on silica (3×20 cm) using ethyl acetate as eluent to afford 152 mg of (2R)-2-amino-3-(2-naphthyl)-N-((1R)-2-(2-naphthyl)-1-(1-phenethyl-1H-tetrazol-5-yl)ethyl)propionamide.

H-NMR (CDCl₃) δ2.16 (dd, 1H); 2.80–3.15 (m, 4H); 3.35–3.55 (m, 2H); 4.48 (dd, 2H); 5.19 (dd, 1H); 6.90–8.02 (21 H)

4-((1R)-2-(2-Naphthyl)-1-((1R)-2-(2-naphthyl)-1-(1-phenethyl-1H-tetra-zol-5-yl)ethylcarbamoyl)ethylcarbamoyl)piperidine-1-carboxylic acid tert-butylester

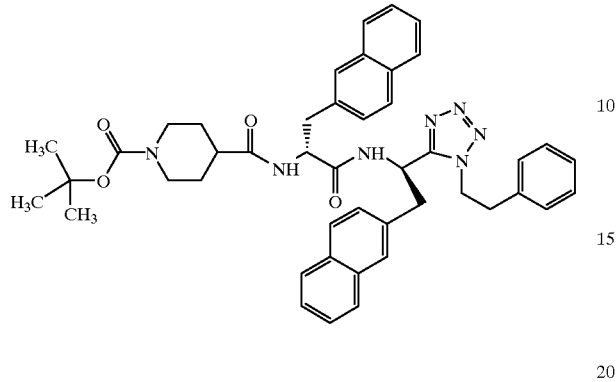

N-tert-butyloxycarbonylpiperidine-4-carboxylic acid (68 mg; 0.296 mmol) was dissolved in methylene chloride (7 ml). HOBT (40 mg; 0.296 mmol) and EDAC (62 mg; 0.326 mmol) were added and the mixture was stirred 15 min at RT. (2R)-2-Amino-3-(2-naphthyl)-N-((1R)-2-(2-naphthyl)-1-(1-phenethyl-1H-tetrazol-5-yl)ethyl)propionamide (152 mg; 0.296 mmol) was added and stirring was continued overnight. Methylene chloride (25 ml) was added. The organic phase was washed with aqueous sodium hydrogencarbonate (25 ml), aqueous sodium hydrogensulfate (10%; 25 ml) and water (25 ml). The organic phase was dried (Magnesium sulfate) and the solvent removed in vacuo to afford 170 mg of 4-((1R)-2-(2-Naphthyl)-1-((1R)-2-(2-naphthyl)-1-(1-phenethyl-1H-tetrazol-5-yl) ethylcarbamoyl) ethylcarbamoyl)piperidine-1-carboxylic acid tert-butylester.

H-NMR (CDCl$_3$) δ1.25–1.52 (m and s, 13H); 1.79 (m, 1H); 2.58 (m, 2H); 2.75 (m, 1H); 2.86 (dd, 1H); 2.96 (dd, 1H); 3.05 (d, 2H); 3.27 (dd, 1H); 3.98 (m, 1H); 4.15 (m, 2H); 4.57 (dd, 1H); 5.04 (dd, 1H); 5.72 (d(br); 1H); 6.53 (d(br); 1H); 6.71–7.80 (19 arom. H)

4-(1R)-2-(2-Naphthyl)-1-((1R)-2-(2-naphthyl)-1-(1-phenethyl-1H-tetrazol-5-yl)ethylcarbamoyl) ethylcarbamoyl)piperidine-1-carboxylic acid tert-butylester (164 mg; 0.218 mmol) was dissolved in methylene chloride (6 ml) and trifluoroacetic acid (3 ml) and stirred for 20 min at RT. The solvent was removed in vacuo. Methylene chloride (10 ml) was added and the organic phase was washed with aqueous sodium hydrogencarbonate (10%; 10 ml). The organic phase was dried (Magnesium sulfate) and the solvent was removed in vacuo. The residue was dissolved in ethyl acetate (5 ml) and hydrogen chloride in ethyl acetate (3M; 2 ml) was added. The solvent was removed in vacuo. The residue was dissolved in methanol (5 ml) and evaporated and this was repeated 3 times with methylene chloride to afford 110 mg of the title compound as a hydrochloride.

H-NMR (CDCl$_3$) (selected peaks) δ2.50 (m, 2H); 2.73 (m, 1H); 2.89–3.09 (m, 7H); 3.31 (dd, 1H); 4.21 (m, 2H); 4.68 (dd, 1H); 5.10 (dd, 1H); 6.70–7.75 (19 arom. H)

HPLC: R$_t$=38.07 min (A1)

Example 26

Piperidine-4-carboxylic acid N-methyl-N-((1R)-2-(2-naphthyl)-1-((1R)2-(2-naphthyl)-1-thiocarbamoylethylcarbamoyl)ethyl)amide

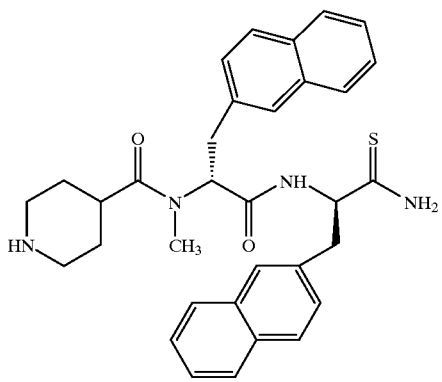

(2R)-2-(N-tert-Butoxycarbonyl-N-methylamino)-3-(2-naphthyl)propionic acid methyl ester

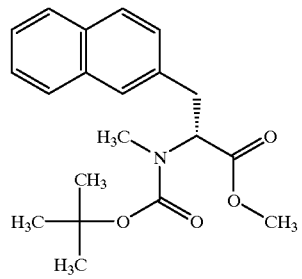

(2R)-2-tert-Butoxycarbonylamino-3-(2-naphthyl) propionic acid (10.0 g; 32.79 mmol) was dissolved in dry DMF (100 ml). Iodomethane (12.25 ml; 196.72 mmol) and silver oxide (26.6 g; 114.75 mmol) were added. The reaction mixture was stirred 12 hours at room temperature. The reaction mixture was filtered and methylene chloride (400 ml) was added to the filtrate. The organic phase was washed with aqueous potassium cyanide (5%; 2×100 ml), water (3×150 ml) and dried (MgSO$_4$). The solvent was removed in vacuo to afford 10.9 g of (2R)-(N-tert-butoxycarbonyl-N-methylamino)-3-(2-naphthyl)propionic acid methylester.

H-NMR (CDCl$_3$) δ (mixture of rotameres) 1.30, 1.35 (two s, 9H); 2.71, 2.74 (two s, 3H); 3.45, 3.19 (two m, 2H); 3.72, 3.74 (two s, 3H); 4.65, 5.06 (two dd, 1H); 7.30–7.80 (7 arom. H)

107

(2R)-2-(N-tert-Butoxycarbonyl-N-methylamino)-3-(2-naphthyl)propionic acid

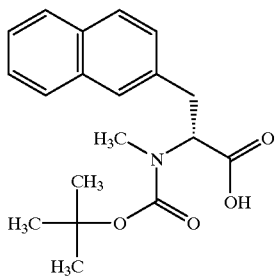

(2R)-2-(N-tert-Butoxycarbonyl-N-methylamino)-3-(2-naphthyl)propionic acid methylester (15.0 g; 43.73 mmol) was dissolved in dioxane (150 ml) and cooled on an icebath. Water (115 ml) and lithium hydroxide (1.15 g; 48.10 mmol) were added. The reaction mixture was stirred 4 hours at room temperature. Ethyl acetate (300 ml) and water (200 ml) were added. Sodium hydrogensulfate (3%) was added until acidic reaction (pH=2.5). The organic phase was washed with water (200 ml) and dried (Magnesium sulfate). The solvent was removed in vacuo to afford 13.5 g of (2R)-2-(N-tert-Butoxycarbonyl-N-methylamino)-3-(2-naphthyl)propionic acid.

H-NMR (CDCl$_3$) δ (mixture of rotameres) 1.30, 1.47 (two s, 9H); 2.66, 2.78 (two s, 3H); 3.21, 3.38 (two dd, 1H); 3.48, 3.51 (two d, 1H); 4.75, 4.83 (two dd, 1H); 7.31–7.82 (7 arom. H).

((1R)-2-(2-Naphthyl)-1-thiocarbamoylethyl)carbamic acid tert-butyl ester

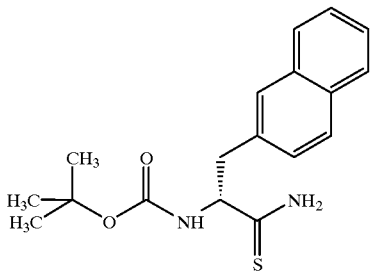

(2R)-2-tert-Butoxycarbonylamino-3-(2-naphthyl)propionic acid amide (1.058 g; 3.36 mmol) and 2,4-bis(4-methoxyphenyl)-1,3-dithia-2,4-diphosphetane-2,4-disulfide (Lawesson's reagent) (0.71 g; 1.76 mmol) were dissolved in dioxane (6 ml). The reaction mixture was heated 30 min at 60° C. and stirred 12 hours at room temperature. The solvent was removed in vacuo and to the residue was added a mixture of water/sodium hydrogencarbonate (1:1; 15 ml) and stirred 30 min at room temperature. The mixture was filtered. The solid was washed with water (2×5 ml) and chromatographed on silica (2×15 cm) using ethyl acetate/heptane (2:1) to afford 0.914 g of ((1R)-2-(2-naphthyl)-1-thiocarbamoylethyl)carbamic acid tert-butylester.

H-NMR (CDCl$_3$) δ1.44 (s,9H); 3.28 (m, 2H); 4.74 (dd, 1H); 4.94 (d(br), 1H); 7.35–7.79 (7 arom. H).

108

(2R) 2-Amino-3-(2-naphthyl)propionthioamide

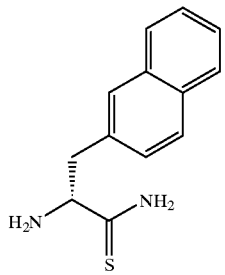

((1R)-2-(2-Naphthyl)-1-thiocarbamoylethyl)carbamic acid tert-butylester (0.45 g; 1.36 mmol) was dissolved in methylene chloride (1.5 ml) and trifluoroacetic acid (1.5 ml) was added. The reaction mixture was stirred for 40 min at room temperature. The solvent was removed in vacuo and the residue was dissolved in methylene chloride. Aqueous sodium hydrogencarbonate was added until basic reaction and the aqueous phase was extracted with methylene chloride (3×15 ml). The combined organic phases were dried (MgSO$_4$) and the solvent was removed in vacuo to afford 0.311 g of (2R)-2-amino-3-(2-naphthyl)propionthioamide.

$^1$H-NMR (CDCl$_3$) δ2.36 (dd, 1H); 3.79 (dd, 1H); 4.19 (dd, 1H); 7.40–7.85 (7 arom. H).

N-Methyl-N-((1R)-2-(2-naphthyl)-1-((1R)-2-(2-naphthyl)-1-thiocarbamoylethylcarbamoyl)ethyl)carbamic acid tert-butylester.

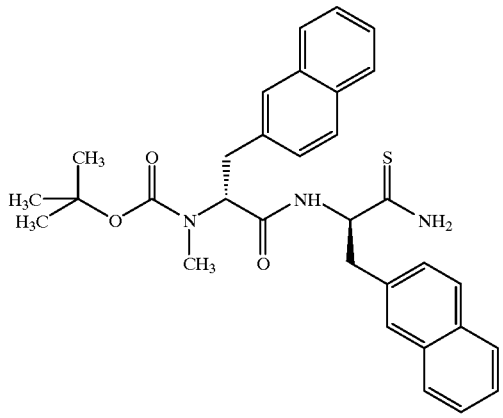

(2R)-2-Amino-3-(2-naphthyl)propionthioamide (0.290 g; 1.2 mmol), (2R)-2-(N-tert-butoxycarbonyl-N-methylamino)-3-(2-naphthyl)propionic acid (0.436 g; 1.3 mmol), HOBT (0.176 g; 1.3 mmol) and EDAC (0.267 g; 1.4 mmol) were dissolved in methylene chloride (20 ml) and stirred 12 hours at RT. Methylene chloride (40 ml) was added and the organic phase was washed with aqueous sodium hydrogensulfate (10%; 40 ml), aqueous sodium hydrogencarbonate (satd.; 40 ml) and dried (Magnesium sulfate). The solvent was removed in vacuo to afford 0.53 g of N-methyl-N-((1R)-2-(2-naphthyl)-1-((1R)-2-(2-naphthyl)-1-thiocarbamoylethylcarbamoyl)ethyl)carbamic acid tert-butylester.

H-NMR (CDCl$_3$) δ (mixture of rotamers, selected peaks) 1.28 (s, 9H); 2.45, 2.51 (two s, 3H); 4.90 (m, 1H); 5.12, 5.20 (two m, 1H).

(2R)-2-Methylamino-3-(2-naphthyl)-N-((1R)-2-(2-naphthyl)-1-thiocarbamoylethyl)propionamide

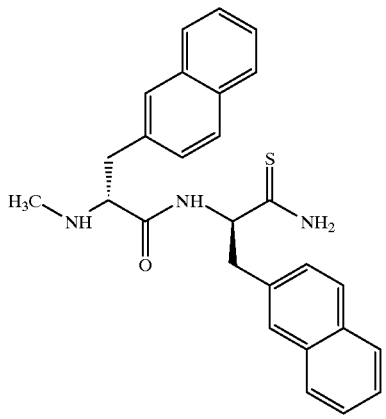

N-Methyl-N-(1R)-2-(2-naphthyl)-1-(1R)-2-(2-naphthyl)-1-thiocarbamoylethylcarbamoyl)ethyl)carbamic acid tert-butylester (0.25 g; 0.462 mmol) was dissolved in methylene chloride (1.5 ml) and trifluoroacetic acid (1.5 ml) was added. The reaction mixture was stirred 1 h at RT. The solvent was removed in vacuo and the residue was dissolved in methylene chloride (5 ml) and washed with aqueous sodium hydrogencarbonate (5 ml). The organic phase was dried (Magnesium sulfate) and the solvent was removed in vacuo to afford 0.201 g of (2R)-2-methylamino-3-(2-naphthyl)-N-((1R)-2-(2-naphthyl)-1-thiocarbamoylethyl)propionamide.

H-NMR (CDCl$_3$) δ2.16 (s, 3H); 2.46 (dd, 1H); 3.07 (dd, 1H); 3.20–3.41 (m, 4H); 5.09 (dd, 1H); 7.12–8.13 (m, 16H)

4-(N-Methyl-N-((1R)-2-(2-naphthyl)-1-((1R)-2-(2-naphthyl)-1-thiocarbamoylethylcarbamoyl)ethyl)carbamoyl)piperidine-1-carboxylic acid tert-butylester

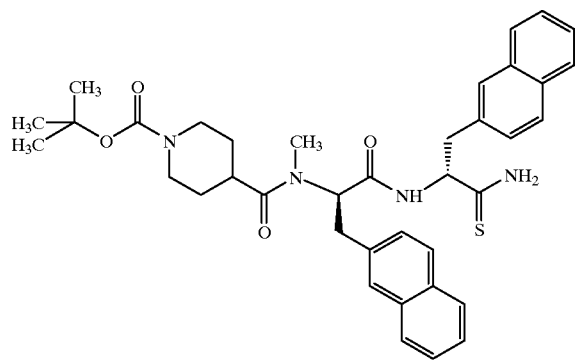

N-tert-Butyloxycarbonylpiperidin-4-carboxylic acid (97 mg; 0.424 mmol) was dissolved in methylene chloride (2 ml). HOAt (58 mg; 0.424 mmol) and EDAC (85 mg; 0.444 mmol) were added. The reaction mixture was stirred 15 min at RT. (2R)-2-Methylamino-3-(2-naphthyl)-N-((1R)-2-(2-naphthyl)-1-thiocarbamoylethyl)propionamide (17 mg; 0.386 mmol) was dissolved in methylene chloride (2 ml) and added. Diisopropylethylamine (0.073 ml; 0.424 mmol) was added and the reaction mixture was stirred 12 hours at room temperature. Tert-butylmethylether (25 ml) was added and the reaction mixture was washed with water (25 ml), aqueous sodium hydrogencarbonate (15 ml), aqueous sodium hydrogensulfate (10%; 15 ml), water (15 ml) and dried (magnesium sulfate). The solvent was removed in vacuo and the residue was chromatographed on silica (3.5×30 cm) using gradient elution, starting with ethyl acetate/heptane (1:1) increasing to ethyl acetate/heptane (2:1) to afford 0.190 g of 4-(N-methyl-N-((1R)-2-(2-naphtyl)-1-((1R)-2-(2-naphthyl)-1-thiocarbamoylethylcarbamoyl)ethyl)carbamoyl)piperidine-1-carboxylic acid tert-butylester.

H-NMR (CDCl$_3$) δ (mixture of rotamers, selected peaks): 1.40, 1.42 (two s, 9H); 2.49, 2.70 (two s, 3H); 3.10 (dd, 1H); 3.48 (dd, 1H); 5.00, 5.09 (two dd, 1H)

4-(N-Methyl-N-((1R)-2-(2-naphthyl)-1-((1R)-2-(2-naphthyl)-1-thiocarbamoylethylcarbamoyl)ethyl)carbamoyl)piperidine-1-carboxylic acid tert-butylester (0.190 g; 0.291 mmol) was dissolved in methylene chloride (5 ml). Trifluoroacetic acid (5 ml) was added and the reaction mixture was stirred 15 min at RT. The solvent was removed in vacuo and the residue was dissolved in methylene chloride and evaporated (2×5 ml). The residue was chromatographed on silica (2×30 cm) using 25% aqueous ammonia/ethanol/methylene chloride (1:9:90) as eluent to afford 57 mg of the title compound.

ESMS: (M+H)$^+$: 553.2
HPLC (A1): R$_t$=29.4 min.

Example 27

Piperidine-4-carboxylic acid ((1R)-1-((1R)-1-(4-carbamoyl-5-phenyl-1,3-thiazol-2-yl)-2-(2-naphthyl)ethylcarbamoyl)-2-(2-naphthyl)ethyl)amide

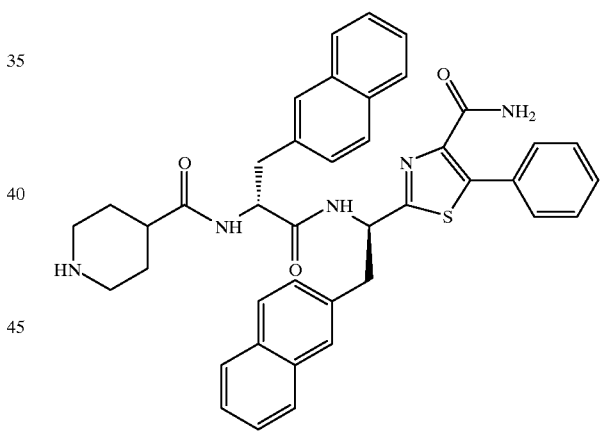

2-Amino-3-oxo-3-phenylpropionic acid methylester

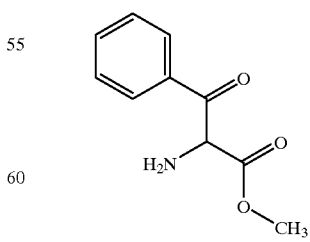

Dry tetrahydrofuran (250 ml) was cooled to −78° C. Potassium tert-butoxide (6.37 g; 56.72 mmol) was dissolved in dry tetrahydrofuran (100 ml) and added.

(Benzhydrylideneamino) acetic acid methyl ester (14.35 g; 56.72 mmol) was added and the reaction mixture was stirred 30 min at −78° C. Benzoyl chloride (6.59 g; 56.72 mmol) was added dropwise and the reaction mixture was stirred 30 min at −78° C. Hydrochloric acid (1.0 M; 175 ml) was added dropwise. The reaction mixture was heated to room temperature and 2/3 of the solvent was removed in vacuo. Water (700 ml) was added and the reaction mixture was washed with diethyl ether (400 ml). The aqueous phase was evaporated in vacuo and the residue was dissolved in methanol and evaporated (2×150 ml). Methanol (80 ml) was added. The mixture was filtrated and the filtrate was evaporated in vacuo. The residue was recrystallised from tetrahydrofuran/diethyl ether to afford 8.86 g of 2-amino-3-oxo-3-phenylpropionic acid methylester as a hydrochloride.

H-NMR (DMSO) δ3.66 (s, 3H); 6.25 (s, 1H); 7.57–8.17 (5 arom. H); 9.20 (s(br); 3H).

2-((2R)-2-tert-Butoxycarbonylamino-3-(2-naphthyl) propionylamino)-3-oxo-3-phenylpropionic acid methylester

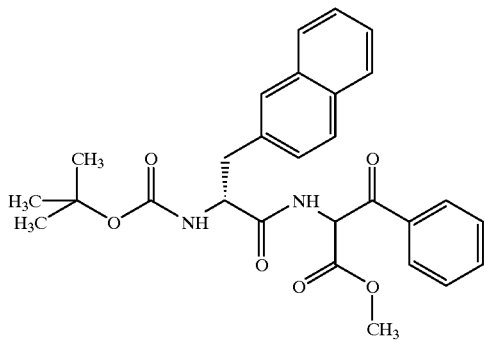

(2R)-2-tert-Butoxycarbonylamino-3-(2-naphthyl) propionic acid (5.49 g; 17.42 mmol) was dissolved in dry tetrahydrofuran (200 ml) and N-methylmorpholine (1.92 ml; 17.42 mmol) was added. The reaction mixture was cooled to −20° C. and stirred 15 min. Isobutyl chloroformate (2.27 ml; 17.42 mmol) was dissolved in dry tetrahydrofuran (3 ml) and added dropwise to the reaction mixture at −20° C. N-methylmorpholine (1.92 ml; 17.42 mmol) and 2-amino-3-oxo-3-phenylpropionic acid methylester (4.0 g; 17.42 mmol) were added and and the mixture was stirred 30 min at −20° C. The reaction mixture was heated to room temperature and the solvent was. removed in vacuo. The residue was dissolved in methylene chloride (200 ml), washed with water (200 ml) and dried (magnesium sulfate). The solvent was removed in vacuo and the residue was chromatographed on silica (5×45 cm) using heptane/ethyl acetate/methylene chloride (2:1:1) as eluent to afford 6.19 g of a diastereomeric mixture of 2-((2R)-2-tert-butoxycarbonylamino-3-(2-naphthyl)propionylamino)-3-oxo-3-phenylpropionic acid methylester.

H-NMR (CDCl₃) δ1.48 (s, 9H); 3.28 (m, 2H), 3.59, 3.67 (two s, 3H); 4.58 (s(br), 1H); 5.00, 5.03 (two m, 1H); 6.13, 6.17 (two d, 1H); 7.28–8.12 (m, 13 H).

2-((1R)-1-tert-Butoxycarbonylamino-2-(2-naphthyl) ethyl)-5-phenyl-1,3-thiazole-4-carboxylic acid methylester

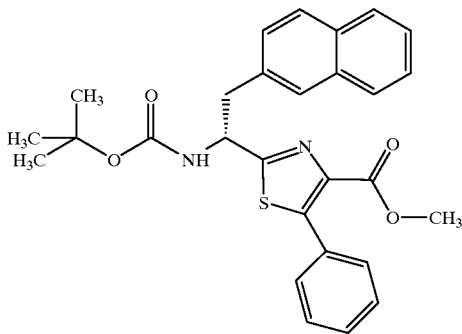

2-((2R)-2-tert-Butoxycarbonylamino-3-(2-naphthyl) propionylamino)-3-oxo-3-phenylpropionic acid methylester (2.2 g; 4.069 mmol) and 2,4-bis(4-methoxyphenyl)-1,3-dithia-2,4-diphosphetane-2,4-disulfide (Lawesson's reagent) (4.1 g; 10.17 mmol) were refluxed 6 hours in 50 ml tetrahydrofuran. The solvent was removed in vacuo and the residue was chromatographed on silica; (4×40 cm) using ethyl acetate/heptane (1:1) as eluent and the residue was recrystalised from ethyl acetate/heptane (1:1; 50 ml) to afford 1.45 g of 2-((1R)-1-(tert-butoxycarbonylamino)-2-(2-naphthyl)-ethyl)-5-phenyl-1,3-thiazole-4-carboxylic acid methyl ester.

H-NMR (CDCl₃) δ1.39 (s, 9H); 3.48 (dd(br); 1H); 3.55 (dd, 1H); 3.85 (s, 3H); 5.26 (s(br), 1H); 5.38 (m, 1H); 7.24–7.81 (12 arom H).

2-((1R)-1-(1-tert-Butoxycarbonylamino)-2-(2-naphthyl)ethyl)-5-phenyl-1,3-thiazole-4-carboxylic acid

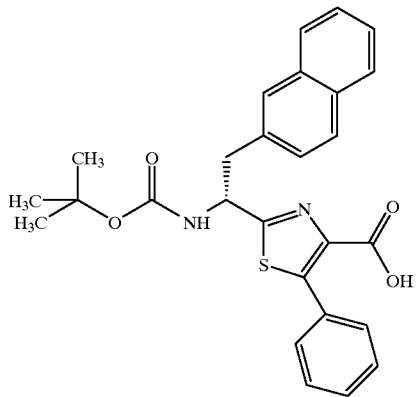

2-((1R)-1-(tert-Butoxycarbonylamino)-2-(2-naphthyl) ethyl)-5-phenyl-1,3-thiazole-4-carboxylic acid methylester (0.35 g; 0.716 mmol) was dissolved in ethanol (99%; 40 ml) and lithium hydroxide (0.112 g; 4.654 mmol) was added. The reaction mixture was stirred 12 hours at room temperature. The solvent was removed in vacuo and the residue was dissolved in water (50 ml) and diethyl ether (50 ml). The solution was made acidic with sodium hydrogensulfate (10%), and the organic phase was dried (magnesium sulfate). The solvent was removed in vacuo to afford 0.185 g of 2-((1R)-1-(tert-butoxycarbonylamino)-2-(2-naphthyl) ethyl)-5-phenyl-1,3-thiazole-4-carboxylic acid.

H-NMR (DMSO) δ1.24 (s, 9H); 3.20 (dd, 1H); 3.55 (dd, 1H); 5.11 (m, 1H); 7.48–7.93 (12 arom. H)

2-((1R)-1-(tert-Butoxycarbonylamino)-2-(2-naphthyl)ethyl)-5-phenyl-1,3-thiazole-4-carboxylic acid amide

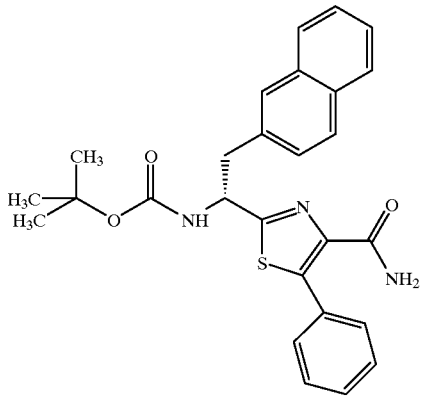

2-((1R)-1-(tert-Butoxycarbonylamino)-2-(2-naphthyl) ethyl)-5-phenyl-1,3-thiazole-4-carboxylic acid (0.17 g; 0.362 mmol) was dissolved in methylene chloride (8 ml). 1-Hydroxybenzotriazole (0.049 g; 0.362 mmol) and N-(3-dimethylaminopropyl)-N'-ethylcarbodiimide hydrochloride (0.083 g; 0.434 mmol) were added. The reaction mixture was stirred 15 min at room temperature. Ammonium hydrogencarbonate (0.057 g; 0.724 mmol) was added and the reaction mixture was stirred 12 h at room temperature. Methylene chloride (20 ml) was added and the reaction mixture was washed with sodium hydrogencarbonate (10%; 10 ml), sodium hydrogensulfate (5%; 2×10 ml) and dried (magnesium sulfate). The solvent was removed in vacuo and the residue was chromatographed on silica (2×15 cm) using ethyl acetate/heptane (1:1) as eluent to afford 0.155 g of 2-((1R)-1-(tert-butoxycarbonylamino)-2-(2-naphthyl) ethyl)-5-phenyl-1,3-thiazole-4-carboxylic acid amide.

$^1$H-NMR (CDCl$_3$) δ1.38 (s, 9H); 3.39–3.52 (m, 2H); 5.17 (d(br), 1H); 5.35 (m, 1H); 5.52 (s(br); 1H); 7.15 (s(br); 7.22–7.82 (12 arom. H).

2-((1R)-1-Amino-2-(2-naphthyl)ethyl)-5-phenyl-1,3-thiazole-4-carboxylic acid amide

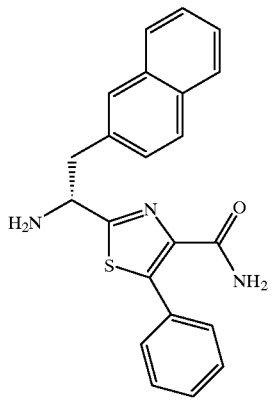

2-((1R)-1-(tert-Butoxycarbonylamino)-2-(2-naphthyl) ethyl)-5-phenyl-1,3-thiazole-4-carboxylic acid amide (0.155 g; 0.327 mmol) was dissolved in methylene chloride (4 ml) and trifluoroacetic acid (4 ml) was added. The reaction mixture was stirred 1 hour at room temperature and the solvent was removed in vacuo. The residue was dissolved in methylene chloride and evaporated (2×2 ml). The residue was dissolved in diethyl ether (2 ml). Hydrochloric acid (1 N; 3 ml) and methanol (10 ml) were added. The solvent was removed in vacuo to afford 0.106 g of 2-((1R)-1-amino-2-(2-naphthyl)-ethyl)-5-phenyl-1,3-thiazole-4-carboxylic acid amide.

$^1$H-NMR (CDCl$_3$) (selected peaks) δ3.45–3.60 (m, 2H); 5.28 (m, 1H).

((1R)-1-((1R)-1-(4-Carbamoyl-5-phenyl-1,3-thiazole-2-yl)-2-(2-naphthyl)ethylcarbamoyl)-2-(2-naphthyl)ethyl)carbamic acid tert-butylester

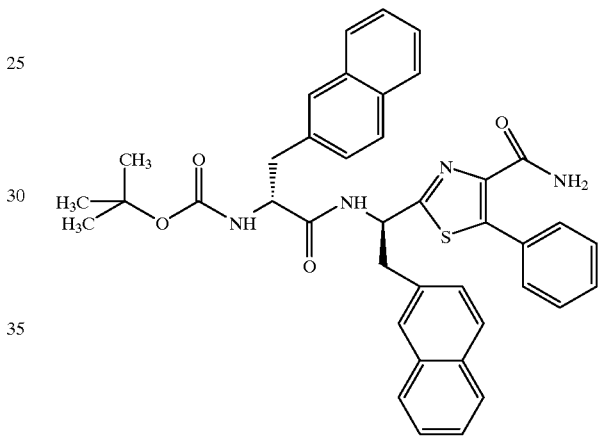

(2R)-2-tert-Butoxycarbonylamino-3-(2-naphthyl) propionic acid (0.107 g; 0.341 mmol) was dissolved in methylene chloride/dimethyl formamide (5:1; 20 ml). 1-Hydroxybenzotriazole (0.046 g; 0.341 mmol) and N-(3-dimethylaminopropyl)-N'-ethylcarbodiimide hydrochloride (0.071 g; 0.369 mmol) were added. The reaction mixture was stirred 15 min at room temperature and 2-((1R)-1-amino-2-(2-naphthyl)ethyl)-5-phenyl-1,3-thiazole-4-carboxylic acid amide (0.106 g; 0.284 mmol) was added. The reaction mixture was stirred 12 hours at room temperature. The reaction mixture was washed with water (20 ml), sodium hydrogensulfate (10%; 20 ml), sodium hydrogencarbonate (satd; 20 ml), water (20 ml) and dried (magnesium sulfate). The solvent was removed in vacuo and the residue was chromatographed on silica (2×15 cm) using ethyl acetate/heptane (2:1) as eluent to afford 0.22 g of ((1R)-1-((1R)-1-(4-carbamoyl-5-phenyl-1,3-thiazole-2-yl)-2-(2-naphthyl)-ethylcarbamoyl)-2-(2-naphthyl)ethyl)carbamic acid tert-butyl ester.

$^1$H-NMR (CDCl$_3$) (selected peaks) δ1.32 (s,9H); 3.13–3.41 (m, 4H); 4.42 (dd, 1H); 5.56 (dd, 1H).

2-((1R)-1-((2R)-2-Amino-3-(2-naphthyl)propionylamino)-2-(2-naphthyl)ethyl)-5-phenyl-1,3-thiazole-4-carboxylic acid amide

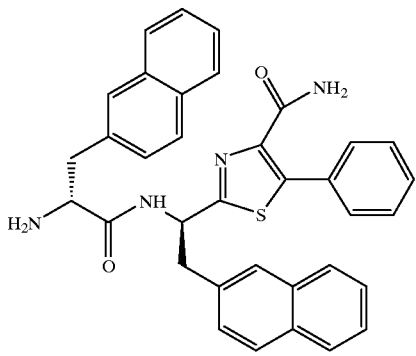

((1R)-1-((1R)-1-(4-Carbamoyl-5-phenyl-1,3-thiazol-2-yl)-2-(2-naphthyl)ethylcarbamoyl)-2-(2-naphthyl)ethyl) carbamic acid tert-butylester (0.22 g; 0.328 mmol) was dissolved in methylene chloride (2.5 ml) and trifluoroacetic acid (2.5 ml) was added. The reaction mixture was stirred 1 h at room temperature and the solvent was removed in vacuo. The residue was dissolved in methylene chloride and evaporated (2×5 ml). The residue was dissolved in methylene chloride (10 ml) and washed with sodium hydrogencarbonate (satd; 10 ml), water (10 ml) and dried (magnesium sulfate). The solvent was removed in vacuo to afford 0.155 g of 2-((1R)-1-((2R)-2-amino-3-(2-naphthyl)propionylamino)-2-(2-naphthyl)ethyl)-5-phenyl-1,3-thiazole-4-carboxylic acid amide.

H-NMR (CDCl$_3$) δ2.55 (dd, 1H); 3.22 (dd, 1H); 3.40 (dd, 1H); 3.52 (dd, 1H); 3.69 (dd, 1H); 5.53 (s(br), 1H); 5.67 (dd, 1H); 7.13–8.12 (m, 22H).

4-(((1R)-1-((1R)-1-(4-Carbamoyl-5-phenyl-1,3-thiazol-2-yl)-2-(2-naphthyl)ethylcarbamoyl)-2-(2-naphthyl)ethyl)carbamoyl)piperidine-1-carboxylic acid tert-butylester

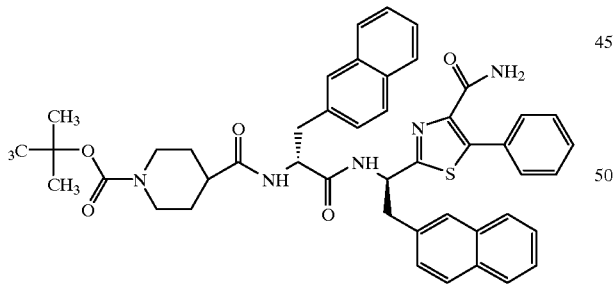

N-tert-Butyloxycarbonylpiperidine-4-carboxylic acid (0.140 g; 0.612 mmol) was dissolved in methylene chloride (5 ml) and N-(3-dimethylaminopropyl)-N'-ethylcarbodiimide hydrochloride (0.058 g; 0.306 mmol) was added. The reaction mixture was stirred 15 min at room temperature. 2-((1R)-1-((2R)-2-(Amino-3-(2-naphthyl)-propionylamino)-2-(2-naphthyl)ethyl)-5-phenyl-1,3-thiazole-4-carboxylic acid amide (0.155 g; 0.278 mmol) was dissolved in methylene chloride (10 ml) and added to the reaction mixture. The reaction mixture was stirred 8 hours at room temperature and washed with water (20 ml), sodium hydrogencarbonate (satd, 20 ml) and dried (magnesium sulfate). The solvent was removed in vacuo and the residue was chromatographed on silica (2.5×30 cm) using ethyl acetate to afford 0.171 g of 4-(((1R)-1-((1R)-1-(4-carbamoyl-5-phenyl-1,3-thiazol-2-yl)-2-(2-naphthyl)ethylcarbamoyl)-2-(2-naphthyl)ethyl)carbamoyl)piperidine-1-carboxylic acid tert-butylester.

$^1$H-NMR (CDCl$_3$) (selected peaks) δ1.44 (s,9H); 2.81 (t, 1H); 3.12 (m, 2H); 3.42 (dd, 1H); 3.85–4.02 (m, 4H); 4.88 (dd, 1H); 5.52 (dd, 1H);

4-(((1R)-1-((1R)-1-(4-Carbamoyl-5-phenyl-1,3-thiazol-2-yl)-2-(2-naphthyl)ethylcarbamoyl)-2-(2-naphthyl)ethyl)carbamoyl)piperidine-1-carboxylic acid tert-butylester (0.171 g; 0.219 mmol) was dissolved in methylene chloride/trifluoroacetic acid (1:1; 10 ml) and stirred 20 min at room temperature. The solvent was removed in vacuo and the residue was dissolved in methylene chloride and evaporated in vacuo three times (3×5 ml) to afford 0.175 g of the title compound.

$^1$H-NMR (CDCl$_3$) (selected peaks) δ3.37 (m, 2H); 3.44 (dd; 1H); 4.80 (m, 1H); 5.55 (dd, 1H).

ESMS: (M+H)$^+$: 682.4

HPLC: (method B): R$_t$=35.08 min.

The following compound may be prepared using the same method as in example 21 using methylamine instead of benzylamine:

(2E)-5-Amino-5-methylhex-2-enoic acid {1-[N-(1-(3-methylcarbamoyl-[1,2,4]oxadiazol-5-yl)-2-phenylethyl)-N-methylcarbamoyl]-2-(2-naphthyl)ethyl}amide

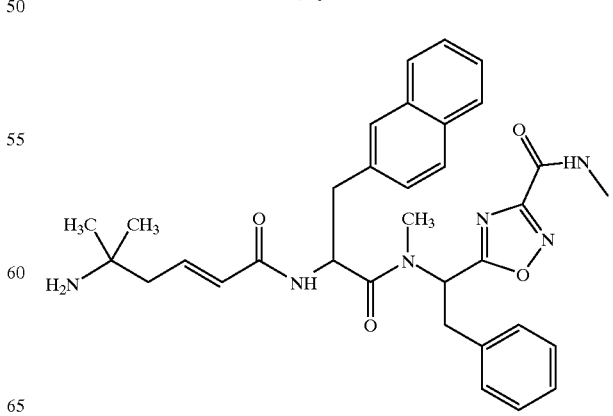

The following compound may be prepared using the same method as in example 21 using dimethylmethylamine instead of benzylamine:

(2E)-5-Amino-5-methylhex-2-enoic acid {1-[N-(1-(3-dimethylcarbamoyl-[1,2,4]oxadiazol-5-yl)-2-phenylethyl)-N-methylcarbamoyl]-2-(2-naphthyl)ethyl}amide

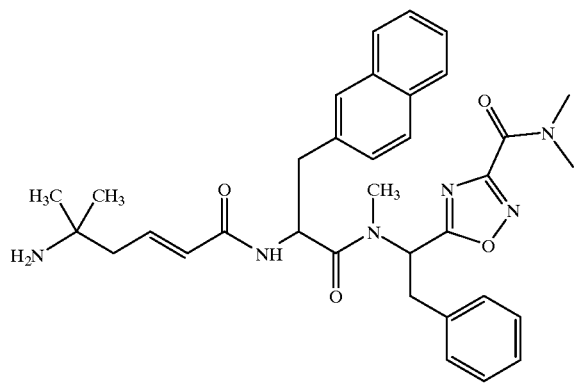

The following compound may be prepared according to method K, analougosly to example 23, using (2E)-5-tert-butoxycarbonylamino-5-methylhex-2-onic acid instead of 3-tert-butoxycarbonylaminomethylbenzoic acid.

(2E)-5-Amino-5-methyl-N-((1R)-1-(N-((1R)-1-(2-hydroxyethoxymethyl)-2-phenylethyl)-N-methylcarbamoyl)-2-(2-naphthyl)ethyl)-N-methylhex-2-enoic acid amide

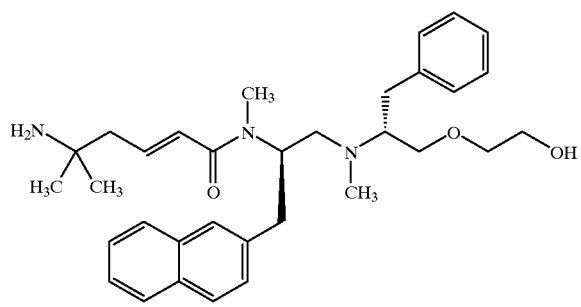

The following compound may be prepared analougosly to example 23, using methylmagnesium bromide instead of lithium boronhydride and (2E)-5-tert-butoxycarbonylamino-5-methylhex-2-onic acid instead of 3-tert-butoxycarbonylaminomethylbenzoic acid.

(2E)-5-Amino-5-methyl-N-((1R)-1-(N-((1R)-1-(2-hydroxy-2-methylpropoxymethyl)-2-phenylethyl)-N-methylcarbamoyl)-2-(2-naphthyl)ethyl)-N-methylhex-2-enoic acid

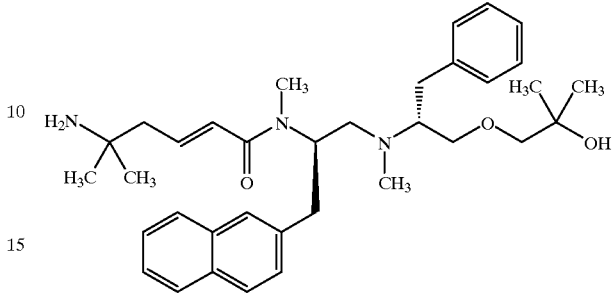

What is claimed is:
1. A compound of formula I

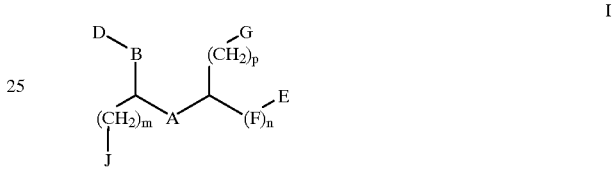

Wherein
n is 0 or 1;
m is 1 or 2;
p is 0, 1 or 2;
A is

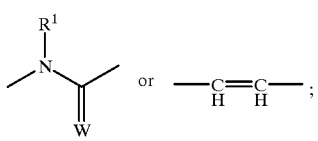

wherein $R^1$ is hydrogen or $C_{1-6}$-alkyl,
W is =O or =S;
with the proviso that when n is 1 and A is a secondary or tertiary amide, B or F is not an amide;
B is

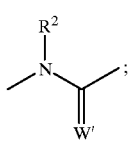

wherein $R^2$ is hydrogen or $C_{1-6}$-alkyl,
W' is =O or =S;
D is

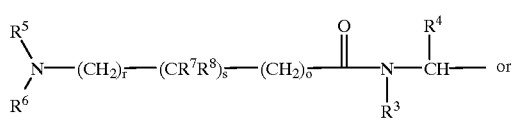

-continued

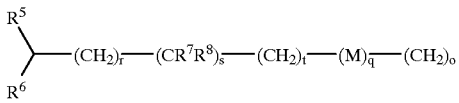

wherein $R^3$, $R^4$, $R^5$, $R^6$, $R^7$ and $R^8$ independently are hydrogen or $C_{1-6}$-alkyl optionally substituted with halogen, amino, hydroxy or aryl; or $R^5$ and $R^6$, $R^6$ and $R^7$, $R^5$ and $R^8$ or $R^7$ and $R^8$ form —$(CH_2)_i$—U—$(CH_2)_j$—, wherein i and j independently are 1 or 2, and U is —O—, —S— or a valence bond;

M is —O—, —S—, —CH=CH—,

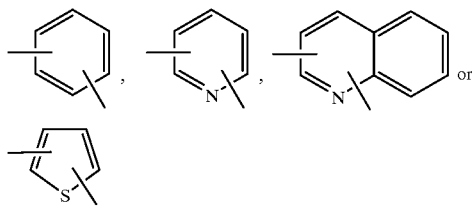

optionally substituted with halogen, amino, hydroxy, $C_{1-6}$-alkyl or $C_{1-6}$-alkoxy;

o, r and t are independently 0, 1, 2, 3 or 4;

q and s are independently 0 or 1;

and r+s+t is 1, 2, 3 or 4;

E is hydrogen,

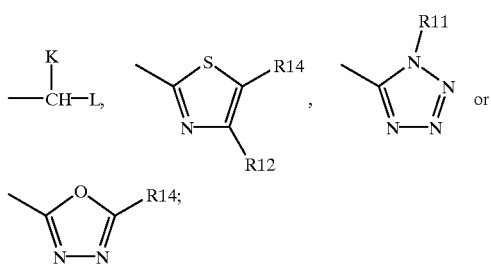

wherein L is hydrogen, —$OR^9$, —$CONR^9R^{10}$, $C_{1-6}$-alkyl optionally substituted with hydroxy or $C_{1-6}$-alkoxy, or L is

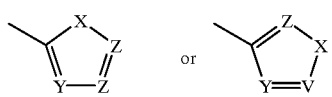

wherein $R^9$ and $R^{10}$ are independently hydrogen, $C_{1-6}$-alkyl or together form —$(CH_2)_k$—U'—$(CH_2)_l$—, wherein k and l independently are 1, 2 or 3, and k+l is 3, 4, 5 or 6, U' is —O—, —S— or a valence bond;

X is —$N(R^{11})$—, —O— or —S—,

V is —$C(R^{12})$= or —N=,

Y is —$C(R^{13})$= or —N=,

Z is —$C(R^{14})$= or —N=, $R^{12}$, $R^{13}$ and $R^{14}$ independently are hydrogen, —$COOR^{15}$, —$CONR^{16}R^{17}$, —$(CH_2)_vNR^{16}R^{17}$, —$(CH_2)_uOR^{15}$, halogen, hydroxy, $C_{1-6}$-alkyl, phenyl, oxazol-5-yl, 5-methyl-[1,2,4]oxadiazol-3-yl, $R^{11}$, $R^{15}$, $R^{16}$ and $R^{17}$ independently are hydrogen or $C_{1-6}$-alkyl optionally substituted with aryl, and u and v are independently 0 or 1, 2, 3, 4, 5 or 6;

K is hydrogen or

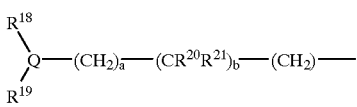

wherein $R^{18}$, $R^{19}$, $R^{20}$ and $R^{21}$ are independently hydrogen, $C_{1-6}$-alkyl optionally substituted with halogen, amino, $C_{1-6}$-alkylamino, hydroxy or aryl; or $R^{18}$ and $R^{19}$, $R^{18}$ and $R^{21}$, $R^{19}$ and $R^{20}$ or $R^{20}$ and $R^{21}$ form —$(CH_2)_{k'}$—Z—$(CH_2)_{l'}$— where k' and l' independently are 1, 2 or 3, and k'+l' are 3, 4, 5 or 6;

Z is —O—, —S— or a valence bond;

b is 0 or 1;

a and d are independently 0, 1, 2, 3 or 4;

and a+b is 1 to 4;

Q is >$CR^{22}$— or >N—, wherein $R^{22}$ is hydrogen or $C_{1-6}$-alkyl,

F is

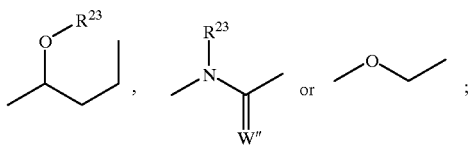

wherein $R^{23}$ is hydrogen or $C_{1-6}$-alkyl,

W" is =O or =S;

G is hydrogen,

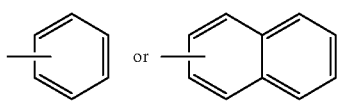

optionally substituted with halogen, amino, hydroxy, $C_{1-6}$-alkyl or $C_{1-6}$-alkoxy;

J is

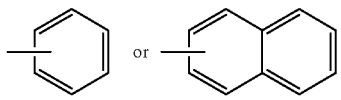

optionally substituted with halogen, amino, hydroxy, $C_{1-6}$-alkyl or $C_{1-6}$-alkoxy; or a pharmaceutically acceptable salt thereof, or optical isomers thereof, in the form of separated, pure or partially purified optical isomers or racemic mixtures thereof.

2. The compound of formula

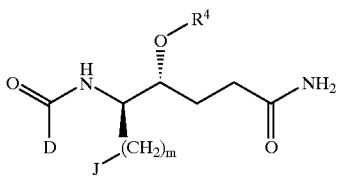

wherein D, J. R⁴ and m are as defined in claim 1;

or a pharmaceutically acceptable salt thereof, or optical isomers thereof, in the form of separated, pure or partially purified optical isomers or racemic mixtures thereof.

3. The compound of formula

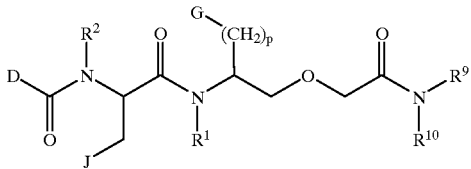

wherein D, R², J, R¹, G, R⁹, R¹⁰ and p are as defined in claim 1;

or a pharmaceutically acceptable salt thereof, optical isomers thereof, in the form of separated, pure or partially purified optical isomers or racemic mixtures thereof.

4. The compound of formula

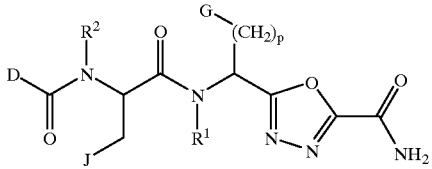

wherein D, R², J, R¹, G, and p are as defined in claim 1;

or a pharmaceutically acceptable salt thereof, or optical isomers thereof, in the form of separated, pure or partially purified optical isomers or racemic mixtures thereof.

5. The compound of formula

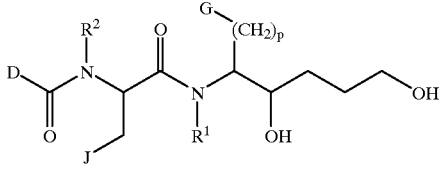

wherein D, R², J, R¹, G, and p are as defined in claim 1;

or a pharmaceutically acceptable salt thereof, or optical isomers thereof, in the form of separated, pure or partially purified optical isomers or racemic mixtures thereof.

6. The compound of formula

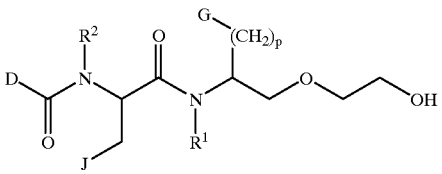

wherein D, R², J, R¹, G, and p are as defined in claim 1, or a pharmaceutically acceptable salt thereof, or optical isomers thereof, in the form of separated, pure or partially purified optical isomers or racemic mixtures thereof.

7. The compound of formula

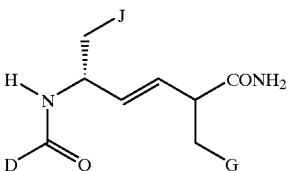

wherein D, G and J are as defined in claim 1;

or a pharmaceutically acceptable salt thereof, or optical isomers thereof, in the form of separated, pure or partially purified optical isomers or racemic mixtures thereof.

8. A compound of claim 1 selected from the group consisting of (3R) Piperidine-3-carboxylic acid ((1R,2E)-4-hydroxymethyl-1-(2-naphthyl)methyl-5-phenylpent-2-enyl)amide, 3-Aminomethyl-N-((1R,2E)-4-hydroxymethyl-1-(2-naphthyl)methyl-5-phenylpent-2-enyl)benzamide, 3-Aminomethyl-N-((1R, 2E, 4S)-4-carbamoyl-5-(2-naphthyl)-1-(2-naphthyl)methylpent-2-enyl)benzamide, Piperidine-4-carboxylic acid ((1R,2E,4S)-4-carbamoyl-5-(2-naphthyl)-1-(2-naphthyl)methylpent-2-enyl)amide, N-((1R)-1-(((1R)-1-(((1S)-5-Amino-1-(dimethylcarbamoyl) pentylcarbamoyl)-2-phenylethoxy)methyl)-2-(2-naphthyl)ethyl)-3-aminomethylbenzamide, N-((1R,4S)-4-(((1S)-5-Amino-1-(dimethylcarbamoyl) pentyl)carbamoyl)-1-((2-naphthyl)methyl)-2-oxo-5-phenylpentyl)-3-aminomethylbenzamide, N-((1R,2R,4S)-4-(((1S)-5-Amino-1-(dimethylcarbamoyl) pentyl)carbamoyl)-2-hydroxy-1-(2-naphthyl)methyl-5-phenylpentyl)-3-aminomethylbenzamide, Piperidine-3-carboxylic acid ((1R, 2R, 4S)-4-(((1S)-5-amino-1-(dimethylcarbamoyl)pentyl)carbamoyl)-2-hydroxy-1-((2-naphthyl)methyl)-5-phenylpentyl)amide, 5-((1R)-1-(N-((2R)-2-(3-Aminomethylbenzoylamino)-3-(2-naphthyl)propionyl)-N-methylamino)-2-phenylethyl)-[1,3,4]oxadiazole-2-carboxylic acid amide, 3-Aminomethyl-N-((1R)-1-{N-[(1R)-1-(((dimethylcarbamoyl)methoxy)methyl)-2-phenylethyl]-N-methylcarbamoyl}-2-(2-naphthyl)ethyl)-N-methylbenzamide, 5-((1R)-1-(((2R)-2-(((4E)4-Amino-4-methylpent-2-enoyl) methylamino)-3-(2-naphthyl)propionyl)methylamino)-2-phenylethyl)-[1,3,4]-oxadiazole-2-carboxylic acid amide (2E)-5-Amino-5-methylhex-2-enoic acid N-{(1R)-1-[((1R)-1-benzyl-2,5-dihydroxypentyl)-N-methylcarbamoyl]-2-(2-naphthyl)ethyl}-N-methylamide, 3-Aminomethyl-N-((1R)-1-{N-[(1R)-1-(2-hydroxyethoxymethyl)-2-phenylethyl]-N- methylcarbamoyl}-2-(2-naphthyl)ethyl)-N-methylbenzamide,

Piperidine-4-carboxylic acid ((1R,2E)4-hydroxymethyl-5-(2-naph-thyl)-1-((2-naphthyl)methyl)pent-2-enyl)amide, Piperidine-4-carboxylic acid ((1R)-2-(2-naphthyl)-1-((1R)-2-(2-naphthyl)-1-(1-phenethyl-1H-tetrazol-5-yl)ethylcarbamoyl)ethyl)amide, Piperidine-4-carboxylic acid N-methyl-N-((1R9-2-(2-naphthyl)-1-((1R)2-(2-naphthyl)-1-thiocarbamoylethylcarbamoyl)ethyl)amide, Piperidine-4-carboxylic acid ((1R)-1-((1R)-1-(4-carbamoyl-5-phe-nyl-1,3-thiazol-2-yl)-2-(2-naphthyl)ethylcarbamoyl)-2-(2-naph-thyl)ethyl)amide, (2E)-5-Amino-5-methyl-N-((1R)-1-(N-((1R)-1-(2-hydroxyethoxymethyl)-2-phenylethyl)-N-methylcarbamoyl)-2-(2-naphthyl)ethyl)-N-methylhex-2-enoic acid amide, and (2E)-5-Amino-5-methyl-N-((1R)-1-(N-((1R)-1-(2-hydroxy-2-methylpropoxymethyl)-2-phenylethyl)-N-methylcarbamoyl)-2-(2-naphthyl)ethyl)-N-methylhex-2-enoic acid, or a pharmaceutically acceptable salt thereof or all possible optical isomers, as separated, pure or partially purified optical isomers or racemic mixtures thereof.

9. A compound of formula I

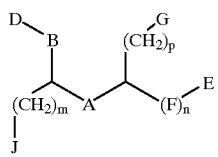

Wherein n is 0 or 1;

m is 1 or 2;

p is 0, 1 or 2;

A is

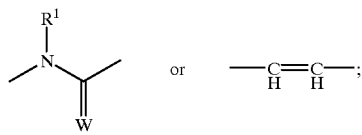

wherein $R^1$ is hydrogen $C_{1-6}$-alkyl,

W is =O or =S;

with the proviso that when A contains a secondary or tertiary amide, either B or F does not contain a secondary or tertiary amide;

B is

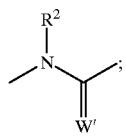

wherein $R^2$ is hydrogen or $C_{1-6}$-alkyl,

W' is =O or =S;

D is

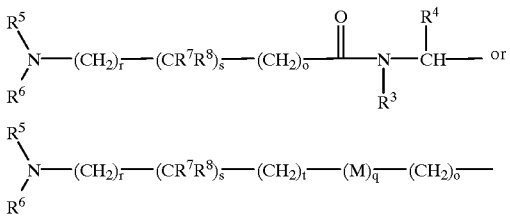

wherein $R^3$, $R^4$, $R^5$, $R^6$, $R^7$ and $R^8$ independently are hydrogen or $C_{1-6}$-alkyl optionally substituted with halogen, amino, hydroxy or aryl; or $R^5$ and $R^6$, $R^6$ and $R^7$, $R^5$ and $R^8$ or $R^7$ and $R^8$ form —(CH$_2$)$_i$—U—(CH$_2$)$_j$—, wherein i and j independently are 1 or 2, and U is —O—, —S— or a valence bond;

M is —O—, —S—, —CH=CH—,

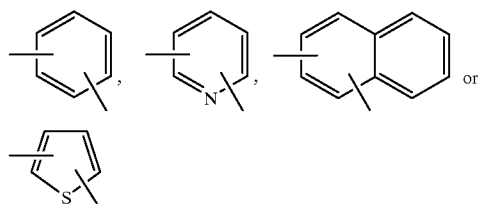

optionally substituted with halogen, amino, hydroxy, $C_{1-6}$-alkyl or $C_{1-6}$-alkoxy;

o, r and t are independently 0, 1, 2, 3 or 4;

q and s are independently 0 or 1;

and r+s+t is 1, 2, 3 or 4;

E is hydrogen,

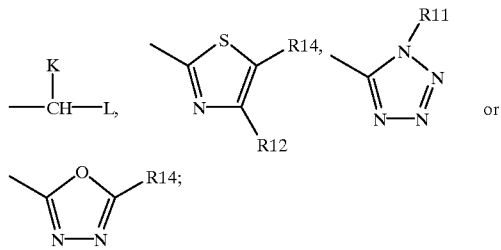

wherein L is hydrogen, —OR$^9$, —CONR$^9$R$^{10}$, $C_{1-6}$-alkyl optionally substituted with hydroxy or $C_{1-6}$-alkoxy, or L is wherein $R^9$ and $R^{10}$ are independently hydrogen, $C_{1-6}$-alkyl or together form —(CH$_2$)$_k$—U'—(CH$_2$)$_l$—, wherein k and l independently are 1, 2 or 3, and k+l is 3, 4, 5 or 6, U' is —O—, —S— or a valence bond;

X is —N(R$^{11}$)—, —O— or —S—,

V is —C(R$^{12}$)= or —N=,
Y is —C(R$^{13}$)= or —N=,
Z is —C(R$^{14}$)= or —N=,
R$^{12}$, R$^{13}$ and R$^{14}$ independently are hydrogen, —COOR$^{15}$, —CONR$^{16}$R$^{17}$, —(CH$_2$)$_v$NR$^{1617}$, —(CH$_2$)$_u$OR$^{15}$, halogen, hydroxy, C$_{1-6}$-alkyl, phenyl, oxazol-5-yl, 5-methyl-[1,2,4]oxadiazol-3-yl,
R$^{11}$, R$^{15}$, R$^{16}$ and R$^{17}$ independently are hydrogen or C$_{1-6}$-alkyl optionally substituted with aryl, and
u and v are independently 0 or 1, 2, 3, 4, 5 or 6;
K is hydrogen or

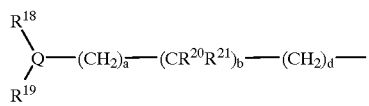

wherein R$^{18}$, R$^{19}$, R$^{20}$ and R$^{21}$ are independently hydrogen, C$_{1-6}$-alkyl optionally substituted with halogen, amino, C$_{1-6}$-alkylamino, hydroxy or aryl; or R$^{18}$ and R$^{19}$, R$^{18}$ and R$^{21}$, R$^{19}$ and R$^{20}$ or R$^{20}$ and R$^{21}$ form —(CH$_2$)$_{k'}$—Z—(CH$_2$)$_{l'}$— where k' and l' independently are 1, 2 or 3, and k'+l' are 3, 4, 5 or 6;
Z is —O—, —S— or a valence bond;
b is 0 or 1;
a and d are independently 0, 1, 2, 3 or 4;
and a+b is 1 to 4;
Q is >CR$^{22}$— or >N—,
wherein R$^{22}$ is hydrogen or C$_{1-6}$-alkyl,
F is

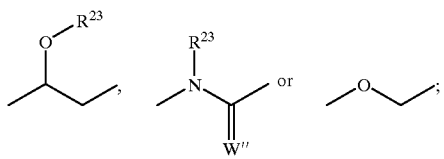

wherein R$^{23}$ is hydrogen or C$_{1-6}$-alkyl,
W" is =O or =S;
G is hydrogen,

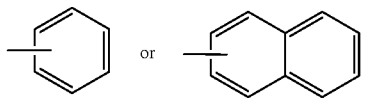

optionally substituted with halogen, amino, hydroxy, C$_{1-6}$-alkyl or C$_{1-6}$-alkoxy;
J is

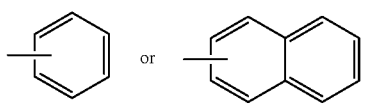

optionally substituted with halogen, amino, hydroxy, C$_{1-6}$-alkyl or C$_{1-6}$-alkoxy;

or a pharmaceutically acceptable salt thereof, or optical isomers thereof, in the form of separated, pure or partially purified optical isomers or racemic mixtures thereof.

10. A pharmaceutical composition comprising, as an active ingredient, an effective amount of a compound of claim 1 together with a pharmaceutically acceptable carrier or diluent.

11. A method of stimulating the release of growth hormone from the pituitary, the method comprising administering to a subject in need thereof an effective amount of a compound of claim 1.

* * * * *

UNITED STATES PATENT AND TRADEMARK OFFICE
CERTIFICATE OF CORRECTION

PATENT NO.    : 6,350,767 B1  
DATED         : February 26, 2002  
INVENTOR(S)   : Lau et al.

It is certified that error appears in the above-identified patent and that said Letters Patent is hereby corrected as shown below:

Column 125,
Line 6, delete "$NR^{1617}$" and insert -- $NR^{16}R^{17}$ --.

Signed and Sealed this

Ninth Day of December, 2003

JAMES E. ROGAN
*Director of the United States Patent and Trademark Office*